US012697320B2

(12) United States Patent
Fathallah et al.

(10) Patent No.: US 12,697,320 B2
(45) Date of Patent: Aug. 4, 2026

(54) TARTARIC ACID ANALOGS AND USES THEREOF

(71) Applicant: Lapix Therapeutics, Inc., Boston, MA (US)

(72) Inventors: Anas M. Fathallah, Wakefield, MA (US); Scott D. Larsen, Gobles, MI (US); Abdulraouf Ramadan, Malden, MA (US)

(73) Assignee: TIM Therapeutics, Inc., Cambridge, MA (US)

( * ) Notice: Subject to any disclaimer, the term of this patent is extended or adjusted under 35 U.S.C. 154(b) by 327 days.

(21) Appl. No.: 18/262,267

(22) PCT Filed: Jan. 28, 2022

(86) PCT No.: PCT/US2022/070407
§ 371 (c)(1),
(2) Date: Jul. 20, 2023

(87) PCT Pub. No.: WO2022/165511
PCT Pub. Date: Aug. 4, 2022

(65) Prior Publication Data

US 2025/0177340 A1 Jun. 5, 2025

Related U.S. Application Data

(60) Provisional application No. 63/248,075, filed on Sep. 24, 2021, provisional application No. 63/215,059, filed on Jun. 25, 2021, provisional application No. 63/143,275, filed on Jan. 29, 2021.

(51) Int. Cl.

| | |
|---|---|
| ***A61K 31/225*** | (2006.01) |
| ***A61K 31/197*** | (2006.01) |
| ***A61P 35/00*** | (2006.01) |
| ***C07C 69/70*** | (2006.01) |
| ***C07C 235/74*** | (2006.01) |

(52) U.S. Cl.
CPC .......... *A61K 31/225* (2013.01); *A61K 31/197* (2013.01); *A61P 35/00* (2018.01); *C07C 69/70* (2013.01); *C07C 235/74* (2013.01)

(58) Field of Classification Search
CPC ..... A61K 31/225; A61K 31/197; A61P 35/00; C07C 69/70; C07C 235/74
See application file for complete search history.

(56) References Cited

U.S. PATENT DOCUMENTS

| | | | | |
|---|---|---|---|---|
| 2,393,820 | A * | 1/1946 | Schnider | C07C 215/76 564/220 |
| 6,004,955 | A | 12/1999 | Jin et al. | |
| 7,943,531 | B2 | 5/2011 | Nemani et al. | |
| 11,648,225 | B2 | 5/2023 | Fathallah et al. | |
| 12,016,836 | B2 | 6/2024 | Fathallah et al. | |
| 2004/0072802 | A1 | 4/2004 | Duan et al. | |
| 2006/0110415 | A1* | 5/2006 | Gupta | A61K 8/0212 424/59 |
| 2007/0099982 | A1 | 5/2007 | Salama | |
| 2013/0129627 | A1 | 5/2013 | Delehanty et al. | |
| 2016/0243220 | A1 | 8/2016 | Balu-Iyer et al. | |
| 2019/0151426 | A1 | 5/2019 | Balu-Iyer et al. | |
| 2023/0089267 | A1 | 3/2023 | Fathallah et al. | |
| 2024/0299327 | A1 | 9/2024 | Fathallah et al. | |

FOREIGN PATENT DOCUMENTS

| | | | |
|---|---|---|---|
| JP | 2016017037 | A | 2/2016 |
| WO | 9638426 | A1 | 12/1996 |
| WO | 2018009507 | A1 | 1/2018 |
| WO | WO 2019/033010 | * | 2/2019 |
| WO | 2019046321 | A1 | 3/2019 |
| WO | 2022192899 | A9 | 9/2022 |
| WO | 2023019242 | A1 | 2/2023 |
| WO | 2023019244 | A1 | 2/2023 |

OTHER PUBLICATIONS

International Search Report and Written Opinion issued in International Application No. PCT/US2023/081345, mailed Apr. 10, 2024, 14 pages.
Albacker LA, Karisola P, Chang YJ, et al. TIM-4, a receptor for phosphatidylserine, controls adaptive immunity by regulating the removal of antigen-specific T cells. J Immunol. 2010;185(11):6839-6849. doi:10.4049/jimmunol.1001360.
Freeman GJ, Casasnovas JM, Umetsu DT, DeKruyff RH. TIM genes: a family of cell surface phosphatidylserine receptors that regulate innate and adaptive immunity. Immunol Rev. 2010;235(1):172-189.
Glassman et al., "Subcutaneous administration of Lyso-phosphatidylserine nanoparticles induces immunological tolerance towards Factor VIII in a Hemophilia A mouse model", International Journal of Pharmaceutics 548(1):642-648 (2018).
(Continued)

*Primary Examiner* — Shirley V Gembeh
(74) *Attorney, Agent, or Firm* — McNeill PLLC

(57) ABSTRACT

Provided herein are tartaric acid analogs represented by the following structural formula: or a pharmaceutically acceptable salt thereof, wherein values for the variables (e.g., A, R) are as described herein. Compounds of structural formula I and pharmaceutically acceptable salts thereof are believed to be useful in overcoming tumor resistance and promoting an immune response. Accordingly, also provided herein are various methods involving compounds of structural formula I, e.g., methods of treating a cancer in a subject in need thereof.

(I)

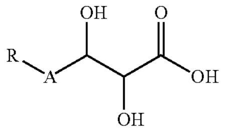

16 Claims, 52 Drawing Sheets

(56) References Cited

OTHER PUBLICATIONS

International Search Report and Written Opinion issued in International Application No. PCT/US2022/070407, mailed May 18, 2022, 16 pages.
International Search Report and Written Opinion issued in International Application No. PCT/US2022/074903, mailed Nov. 30, 2022, 13 pages.
International Search Report and Written Opinion issued in International Application No. PCT/US2022/074908, mailed Oct. 19, 2022, 15 pages.
International Search Report and Written Opinion issued in International Application No. PCT/US2022/071082, mailed Jun. 28, 2022, 15 pages.
Kelleher RJ Jr, Balu-lyer S, Loyall J, et al. Extracellular Vesicles Present in Human Ovarian Tumor Microenvironments Induce a Phosphatidylserine-Dependent Arrest in the T-cell Signaling Cascade. Cancer Immunol Res. 2015;3(11):1269-1278. doi:10.1158/2326-6066.CIR-15-0086.
Kent, S. J., Karlik, S. J., Cannon, C., Hines, D. K., Yednock, T. A., Fritz, L. C., & Horner, H. C. (1995). A monoclonal antibody to α4 integrin suppresses and reverses active experimental allergic encephalomyelitis. Journal of neuroimmunology, 58(1), 1-10.
Ramadan A, Lucca LE, Carrié N, Desbois S, Axisa PP, Hayder M, Bauer J, Liblau RS, Mars LT. In situ expansion of T cells that recognize distinct self-antigens sustains autoimmunity in the CNS. Brain. May 2016;139(Pt 5):1433-46. doi: 10.1093/brain/aww032. Epub Mar. 21, 2016. PMID: 27000832.
Sabatos-Peyton, C. A. et al. Blockade of Tim-3 binding to phosphatidylserine and CEACAM1 is a shared feature of anti-Tim-3 antibodies that have functional efficacy. Oncoimmunology 7, e1385690 (2018).
Santiago C, Ballesteros A, Martínez-Muñoz L, et al. Structures of T cell immunoglobulin mucin protein 4 show a metal-Ion-dependent ligand binding site where phosphatidylserine binds. Immunity. 2007;27(6):941-951. doi:10.1016/j.immuni.2007.11.008.
Serrano et al., "Parallel synthesis and yeast growth inhibition screening of succinamic acid libraries," Journal of Combinatorial Chemistry 9(4):635-643 (2007).
Serre L, Girard M, Ramadan A, Menut P, Rouquié N, Lucca LE, Mahiddine K, Leobon B, Mars LT, Guerder S. Thymic-Specific Serine Protease Limits Central Tolerance and Exacerbates Experimental Autoimmune Encephalomyelitis. J Immunol. Dec. 1, 2017;199(11):3748-3756. doi: 10.4049/jimmunol.1700667. Epub Oct. 23, 2017. PMID: 29061767.
Urwyler, S., et al., "Drug Design, in Vitro Pharmacology, and Structure-Activity Relationships of 3-Acylamino-2-aminopropionic Acid Derivatives, a Novel Class of Partial Agonists at the Glycine Site on the N-Methyl-D-aspartate (NMDA) Receptor Complex", Journal of Medicinal Chemistry, vol. 52, No. 16, Aug. 27, 2009.
Wolf, Y., Anderson, A.C. & Kuchroo, V.K. TIM3 comes of age as an inhibitory receptor. Nat Rev Immunol 20, 173-185 (2020). https://doi.org/10.1038/s41577-019-0224-6.

* cited by examiner

TARTARIC ACID ANALOGS AND USES THEREOF

RELATED APPLICATIONS

This application is the U.S. National Stage of International Application No. PCT/US2022/070407, filed on Jan. 28, 2022, which designates the U.S., published in English, and claims the benefit of U.S. Provisional Application No. 63/248,075, filed on Sep. 24, 2021, U.S. Provisional Application No. 63/215,059, filed on Jun. 25, 2021, and U.S. Provisional Application No. 63/143,275, filed on Jan. 29, 2021. The entire teachings of the above applications are incorporated herein by reference.

BACKGROUND

The loss of anti-tumor T-cell activity and low T-cell infiltration into solid tumors are among the documented tumor microenvironment related factors that confer tumor resistance to therapy and promote tumor evasion of the body's innate immune response. Published reports have shown that phosphatidylserine (PS) present in human ovarian tumor microenvironments can induce T-cell signaling arrest. T cell immunoglobulin and mucin domain (TIM) receptors, including TIM1, TIM3 and TIM4, have been established as PS receptors, and the PS-TIM interaction has been shown to play a role in innate and adaptive immunity.

TIM4 expression has been shown to be upregulated after chemotherapy-induced cell death, and stress release of damage-associated molecular patterns (DAMPs). Recent data suggest that DAMPs can also play a role in promoting carcinogenicity. For example, high mobility group box 1 (HMGB1) can suppress the efficacy of chemotherapeutics and DNA-based vaccines by reducing the immunogenicity of antigen released from dying tumor cells. This is mainly mediated via TIM3 receptors on the surface of dendritic cells.

Checkpoint inhibitors were initially expected to be very promising therapies for overcoming tumor resistance to therapy and the ability of tumors to evade the body's innate immune response. However, published data and clinical observations suggest limitations to currently marketed checkpoint inhibitors.

Accordingly, there is a need for therapies that overcome tumor resistance and promote the immune response.

SUMMARY

Provided herein is a compound represented by the following structural formula:

(I)

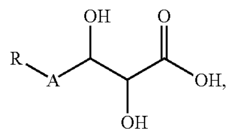

or a pharmaceutically acceptable salt thereof, wherein values for the variables (e.g., A, R) are as described herein.

Also provided herein is a pharmaceutical composition comprising a compound of the disclosure (e.g., a compound of any of the structural formulas depicted herein, such as structural formula I, Ia or Ia'), or a pharmaceutically acceptable salt thereof, and a pharmaceutically acceptable carrier.

Also provided herein is a liposome comprising a compound of the disclosure (e.g., a compound of any of the structural formulas depicted herein, such as structural formula I, Ia or Ia'), or a pharmaceutically acceptable salt thereof.

Also provided herein are methods of promoting the survival, proliferation or activity of an immune cell; inhibiting immune cell anergy; inhibiting regulatory T cells or myeloid-derived suppressor cells; activating an immune cell; modulating the expression or activity of a T cell immunoglobulin and mucin domain (TIM) receptor; modulating the expression or activity of an immune checkpoint; modulating production of tumor necrosis factor alpha (TNFα); promoting the expression or activity of a cytolytic molecule; inducing or maintaining central memory phenotype of an immune cell (e.g., a T-cell, such as a $CD8^+$ T-cell); inhibiting the expression or activity of an exhaustion marker; and enhancing cytotoxicity of a cytotoxic agent, comprising contacting a cell (e.g., immune cell) with a compound of the disclosure (e.g., a compound of any of the structural formulas depicted herein, such as structural formula I, Ia or Ia'), or a pharmaceutically acceptable salt thereof.

Also provided herein is a method of treating a cancer in a subject in need thereof, comprising administering to the subject a therapeutically effective amount of a compound of the disclosure (e.g., a compound of any of the structural formulas depicted herein, such as structural formula I, Ia or Ia'), or a pharmaceutically acceptable salt thereof.

Also provided herein is a compound for a use described herein (e.g., treatment of a cancer), wherein the compound is a compound of the disclosure (e.g., a compound of any of the structural formulas depicted herein, such as structural formula I, Ia or Ia'), or a pharmaceutically acceptable salt thereof. Also provided herein is use of a compound of the disclosure (e.g., a compound of any of the structural formulas depicted herein, such as structural formula I, Ia or Ia'), or a pharmaceutically acceptable salt thereof, for the manufacture of a medicament for a use described herein (e.g., treatment of a cancer).

BRIEF DESCRIPTION OF THE DRAWINGS

The foregoing will be apparent from the following more particular description of example embodiments.

DETAILED DESCRIPTION

Figure 1A:
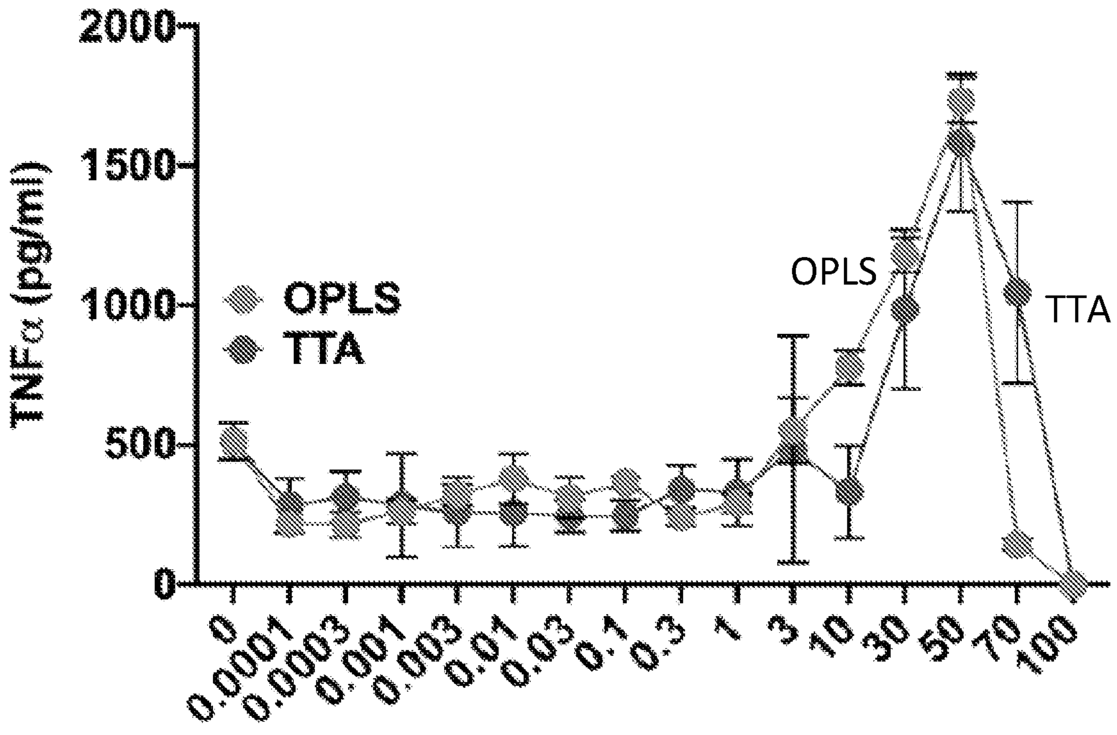
FIG. 1A shows dose-response of TNF-α after exposure to different doses of O-phospho-L-serine (OPLS) or L-(+)-tartaric acid (TTA).

A description of example embodiments follows.

Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the relevant contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version 17.0.0.206, PerkinElmer Informatics, Inc.).

When introducing elements disclosed herein, the articles "a," "an," "the," and "said" are intended to mean that there are one or more of the elements. Further, the one or more elements may be the same or different.

"Alkyl" refers to a branched or straight-chain, monovalent, hydrocarbon radical having the specified number of carbon atoms. Thus, "($C_2$-$C_8$)alkyl" refers to a radical having from 2-8 carbon atoms in a branched or linear arrangement. Typically, alkyl is ($C_1$-$C_{25}$)alkyl, e.g., ($C_1$-$C_{15}$)alkyl, ($C_1$-$C_{10}$)alkyl, ($C_1$-$C_8$)alkyl, ($C_2$-$C_8$)alkyl, ($C_1$-$C_6$)alkyl, ($C_2$-$C_6$)alkyl, ($C_1$-$C_5$)alkyl, ($C_2$-$C_5$)alkyl or ($C_2$-$C_3$)alkyl. Examples of alkyl groups include methyl, ethyl, n-propyl, isopropyl, n-butyl, isobutyl, sec-butyl, t-butyl, n-pentyl, isopentyl, neopentyl, 2-methylpentyl, n-hexyl, and the like. In some aspects, alkyl is optionally substituted, e.g., with one or more substituents described herein.

"Alkenyl" refers to a branched or straight-chain, monovalent, hydrocarbon radical having at least one carbon-carbon double bond and the specified number of carbon atoms. Thus, "($C_2$-$C_8$)alkenyl" refers to a radical having at least one carbon-carbon double bond and from 2-8 carbon atoms in a branched or linear arrangement. Typically, alkenyl is ($C_1$-$C_{25}$)alkenyl, e.g., ($C_1$-$C_{15}$)alkenyl, ($C_1$-$C_{10}$)alkenyl, ($C_1$-$C_5$)alkenyl, ($C_2$-$C_5$)alkenyl, ($C_1$-$C_6$)alkenyl, ($C_2$-$C_6$)alkenyl, ($C_1$-$C_5$)alkenyl or ($C_2$-$C_5$)alkenyl. Examples of alkenyl groups include ethenyl, 2-propenyl, 1-propenyl, 2-methyl-1-propenyl, 1-butenyl, 2-butenyl, 1-pentenyl, 2-pentenyl, 3-pentenyl, allyl, 1, 3-butadienyl, 1, 3-dipentenyl, 1,4-dipentenyl, 1-hexenyl, 1,3-hexenyl, 1,4-hexenyl, 1,3,5-trihexenyl, 2,4-dihexenyl, and the like. In some aspects, alkenyl is optionally substituted, e.g., with one or more substituents described herein.

"Aryl" refers to a monocyclic or polycyclic (e.g., bicyclic, tricyclic), aromatic, hydrocarbon ring system having the specified number of ring atoms, and includes aromatic rings fused to non-aromatic rings, as long as one of the fused rings is an aromatic hydrocarbon. Thus, "($C_6$-$C_{15}$)aryl" refers to a ring system having from 6-15 ring atoms. Examples of aryl include phenyl, naphthyl and fluorenyl. In some aspects, aryl (e.g., ($C_6$-$C_{15}$)aryl) is phenyl, naphthyl or fluorenyl. In some aspects, aryl is optionally substituted, e.g., with one or more substituents described herein.

"Heteroaryl" refers to a monocyclic or polycyclic (e.g., bicyclic, tricyclic), aromatic, hydrocarbon ring system having the specified number of ring atoms, wherein at least one carbon atom in the ring system has been replaced with a heteroatom selected from nitrogen, sulfur and oxygen. Thus, "($C_5$-$C_{15}$)heteroaryl" refers to a heteroaromatic ring system having from 5-15 ring atoms consisting of carbon, nitrogen, sulfur and oxygen. "Heteroaryl" includes heteroaromatic rings fused to non-aromatic rings, as long as one of the fused rings is a heteroaromatic hydrocarbon. A heteroaryl can contain 1, 2, 3 or 4 (e.g., 1, 2 or 3) heteroatoms independently selected from nitrogen, sulfur and oxygen. In some aspects, a heteroaryl contains 1, 2 or 3 heteroatoms, each of which is nitrogen. Typically, heteroaryl is ($C_5$-$C_{20}$)heteroaryl, e.g., ($C_5$-$C_{11}$)heteroaryl, ($C_5$-$C_{12}$)heteroaryl, $C_5$ heteroaryl or $C_6$ heteroaryl. Monocyclic heteroaryls include, but are not limited to, furan, oxazole, thiophene, triazole, triazene, thiadiazole, oxadiazole, imidazole, isothiazole, isoxazole, pyrazole, pyridazine, pyridine, pyrazine, pyrimidine, pyrrole, tetrazole and thiazole. Bicyclic heteroaryls include, but are not limited to, indolizine, indole, isoindole, indazole, benzimidazole, benzofuran, benzothiazole, purine, quinoline, isoquinoline, cinnoline, phthalazine, quinazoline, quinoxaline, naphthyridine and pteridine. In some aspects, heteroaryl (e.g., ($C_5$-$C_{15}$)heteroaryl) is pyridinyl, pyrimidinyl or carbazolyl. In some aspects, heteroaryl is optionally substituted, e.g., with one or more substituents described herein.

"Alkoxy" refers to an alkyl radical attached through an oxygen linking atom, wherein alkyl is as described herein. Examples of alkoxy include, but are not limited to, methoxy, ethoxy, propoxy, isopropoxy, and the like.

"Halogen" and "halo" are used interchangeably herein and each refers to fluorine, chlorine, bromine, or iodine. In some aspects, halo is fluoro, chloro or bromo. In some aspects, halo is fluoro.

"Haloalkyl" includes mono, poly, and perhaloalkyl groups, wherein each halogen is independently selected from fluorine, chlorine, bromine and iodine (e.g., fluorine, chlorine and bromine), and alkyl is as described herein. In one aspect, haloalkyl is perhaloalkyl (e.g., perfluoroalkyl). In some aspects, haloalkyl is fluoroalkyl. Examples of haloalkyl include, but are not limited to, trifluoromethyl and pentafluoroethyl.

"Haloalkoxy" refers to a haloalkyl radical attached through an oxygen linking atom, wherein haloalkyl is as described herein. Examples of haloalkoxy include, but are not limited to, trifluoromethoxy.

The term "substituted" refers to replacement of a hydrogen atom with a suitable substituent. Typically, the suitable substituent replaces a hydrogen atom bound to a carbon atom, but a substituent may also replace a hydrogen bound to a heteroatom, such as a nitrogen atom. It will be understood that "substitution" or "substituted with" includes the implicit proviso that such substitution is in accordance with permitted valence of the substituted atom. It is also preferred that the substituent, and the substitution, result in a stable compound, e.g., which does not spontaneously undergo transformation such as by rearrangement, cyclization, elimination, etc. Suitable substituents for use herein include acyclic and cyclic, branched and unbranched, carbocyclic and heterocyclic, aromatic and non-aromatic substituents of organic compounds. For example, suitable substituents can include halogen, hydroxyl, carbonyl (such as carboxyl, alkoxycarbonyl, formyl, or acyl), thiocarbonyl (such as thioester, thioacetate, or thioformate), alkyl, alkoxy, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, cycloalkyl, heterocyclyl, aralkyl, aryl or heteroaryl. It will be understood by those skilled in the art that substituents can themselves be substituted, if appropriate. Accordingly, substituents can further include an acetamide, for example.

The permissible substituents can be one or more and the same or different for appropriate organic compounds. Thus, an "optionally substituted" group is, in some aspects, substituted with 0-5 (e.g., 0-3, 0, 1, 2, 3, 4, 5) substituents independently selected from halo, $(C_1-C_6)$alkoxy, $(C_1-C_6)$haloalkoxy, $(C_1-C_6)$alkyl, $(C_1-C_6)$haloalkyl, $(C_6-C_{15})$aryl or $(C_5-C_{15})$heteroaryl. In some aspects, an optionally substituted aryl or heteroaryl is substituted with 0-5 (e.g., 0-3, 0, 1, 2, 3, 4, 5) substituents independently selected from halo, $(C_1-C_6)$alkoxy, $(C_1-C_6)$haloalkoxy, $(C_1-C_6)$alkyl or $(C_1-C_6)$haloalkyl. In some aspects, an optionally substituted" aryl or heteroaryl is substituted with 0-5 (e.g., 0-3, 0, 1, 2, 3, 4, 5) substituents independently selected from halo, $(C_1-C_3)$alkoxy, $(C_1-C_3)$haloalkoxy, $(C_1-C_3)$alkyl or $(C_1-C_3)$haloalkyl. In some aspects, an optionally substituted alkyl or alkenyl is substituted with 0-5 (e.g., 0-3, 0, 1, 2, 3, 4, 5) substituents independently selected from halo (e.g., fluoro), $(C_1-C_6)$alkoxy, $(C_1-C_6)$haloalkoxy (e.g., $(C_1-C_6)$fluoroalkoxy), $(C_6-C_{15})$aryl or $(C_5-C_{15})$heteroaryl.

The term "optionally substituted", as used herein, means that substitution is optional and, therefore, it is possible for the atom or moiety designated as "optionally substituted" to be unsubstituted or substituted. Unless otherwise indicated, e.g., as with the terms "substituted" or "optionally substituted," a group designated herein is unsubstituted.

As used herein, the term "compound of the disclosure" refers to a compound of any structural formula depicted herein (e.g., a compound of structural formula I or a sub-formula thereof, such as a compound of structural formula Ia or Ia'), as well as isomers, such as stereoisomers (including diastereoisomers, enantiomers and racemates) and tautomers thereof, isotopically labeled variants thereof (including those with deuterium substitutions), and inherently formed moieties (e.g., polymorphs and/or solvates, such as hydrates) thereof. When a moiety is present that is capable of forming a salt, then salts are included as well, in particular, pharmaceutically acceptable salts thereof.

Compounds of the disclosure may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemic mixtures, individual isomers (e.g., diastereomers, enantiomers, geometrical isomers (including cis and trans double bond isomers), conformational isomers (including rotamers and atropisomers), tautomers) and intermediate mixtures, with all possible isomers and mixtures thereof being included, unless otherwise indicated.

When a disclosed compound is depicted by structure without indicating the stereochemistry, and the compound has one or more chiral centers, it is to be understood that the structure encompasses one enantiomer or diastereomer of the compound separated or substantially separated from the corresponding optical isomer(s), a racemic mixture of the compound and mixtures enriched in one enantiomer or diastereomer relative to its corresponding optical isomer(s). When a disclosed compound is depicted by a structure indicating stereochemistry, and the compound has more than one chiral center, the stereochemistry indicates relative stereochemistry, rather than the absolute configuration of the substituents around the one or more chiral carbon atoms. "R" and "S" can be used to indicate the absolute configuration of substituents around one or more chiral carbon atoms. D- and L- can also be used to designate stereochemistry. Thus, the tartaric acid residue present in a compound of structural formula I can be in the D-configuration or, preferably, the L-configuration. In some aspects, the tartaric acid residue present in a compound of structural formula I or Ia is in the (2R,3R) configuration. The (2R,3R) enantiomer or diastereomer of a compound of formulas I and Ia can be denoted in structural formulas I and Ia, for example, as follows:

(I')

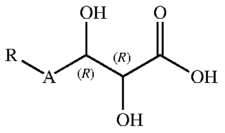

and (Ia')

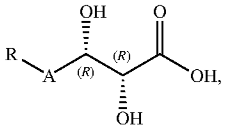

respectively, wherein (R) indicates the absolute configuration of the substituents around the carbon atom to which it pertains.

"Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms.

"Racemate" or "racemic mixture," as used herein, refer to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left|\frac{R-S}{R+S}\right| \times 100\%,$$

where R and S represent the respective fractions of each enantiomer in a mixture, such that R+S=1. An enantiomer may be present in an ee of at least or about 50%, at least or about 60%, at least or about 70%, at least or about 80%, at least or about 90%, at least or about 95%, at least or about 98%, at least or about 99% or at least or about 99.9%.

Percent diastereomeric excess (de) is defined as the absolute difference between the mole fraction of each diastereomer multiplied by 100% and can be represented by the following equation:

$$de = \left|\frac{D1-(D2+D3+D4\ \ldots)}{D1+(D2+D3+D4\ \ldots)}\right| \times 100\%,$$

where D1 and (D2+D3+D4 . . . ) represent the respective fractions of each diastereomer in a mixture, such that D1+(D2+D3+D4 . . . )=1. A diastereomer may be present in a de of at least or about 50%, at least or about 60%, at least or about 70%, at least or about 80%, at least or about 90%, at least or about 95%, at least or about 98%, at least or about 99% or at least or about 99.9%.

Unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this disclosure. In all provided structures, any hydrogen atom can also be independently selected from deuterium ($^{2}H$), tritium ($^{3}H$) and/or fluorine ($^{18}F$). Such compounds are useful, for example, as analytical tools, as probes in biological assays, or as therapeutic agents in accordance with the present disclosure.

The phrase "pharmaceutically acceptable" means that the substance or composition the phrase modifies is, within the scope of sound medical judgment, suitable for use in contact with the tissues of humans and lower animals without undue toxicity, irritation, allergic response and the like, and are commensurate with a reasonable benefit/risk ratio.

As used herein, the term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids, and suitable inorganic and organic bases.

Examples of pharmaceutically acceptable acid addition salts are salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like.

Either the mono-, di- or tri-acid salts can be formed, and such salts can exist in either a hydrated, solvated or substantially anhydrous form.

Salts derived from appropriate bases include salts derived from inorganic bases, such as alkali metal, alkaline earth metal, and ammonium bases, and salts derived from aliphatic, alicyclic or aromatic organic amines, such as methylamine, trimethylamine and picoline, or $N^{+}((C_1\text{-}C_4)alkyl)_4$ salts. Representative alkali or alkaline earth metal salts include sodium, lithium, potassium, calcium, magnesium, barium and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Compounds described herein can also exist as "solvates" or "hydrates." A "hydrate" is a compound that exists in a composition with one or more water molecules. A hydrate can include water in stoichiometric quantities, such as a monohydrate or a dihydrate, or can include water in random amounts. A "solvate" is similar to a hydrate, except that a solvent other than water, such as methanol, ethanol, dimethylformamide, diethyl ether, or the like replaces water. Mixtures of such solvates or hydrates can also be prepared. The source of such solvate or hydrate can be from the solvent of crystallization, inherent in the solvent of preparation or crystallization, or adventitious to such solvent.

"Pharmaceutically acceptable carrier" refers to a nontoxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Treating," as used herein, refers to taking steps to deliver a therapy to a subject, such as a mammal, in need thereof (e.g., as by administering to a mammal one or more therapeutic agents). "Treating" includes inhibiting the disease or condition (e.g., as by slowing or stopping its progression or causing regression of the disease or condition), and relieving the symptoms resulting from the disease or condition.

"A therapeutically effective amount" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual.

An effective amount of an agent to be administered can be determined by a clinician of ordinary skill using the guidance provided herein and other methods known in the art. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects.

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some aspects, a subject is a human.

Compounds

A first embodiment is a compound represented by the following structural formula:

(I)

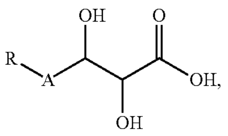

or a pharmaceutically acceptable salt thereof, wherein:

A is *—OC(O)—, *—N($R^1$)C(O)— or *—O($CH_2$)—;

* indicates the point of attachment of A to R;

R is hydrogen, or ($C_1$-$C_8$)alkyl or ($C_1$-$C_8$)alkenyl substituted with one or more independently selected ($C_6$-$C_{15}$) aryl or ($C_5$-$C_{15}$)heteroaryl; and $R^1$ is hydrogen, or ($C_1$-$C_8$)alkyl or ($C_1$-$C_8$)alkenyl optionally substituted with one or more independently selected ($C_6$-$C_{15}$)aryl or ($C_5$-$C_{15}$)heteroaryl, wherein each alkyl and alkenyl is optionally and independently further substituted with one or more fluoro, and each aryl and heteroaryl is optionally and independently substituted with one or more $R^2$ independently selected from halo, ($C_1$-$C_3$)alkoxy, ($C_1$-$C_3$)haloalkoxy, ($C_1$-$C_3$)alkyl or ($C_1$-$C_3$)haloalkyl.

In a first aspect of the first embodiment, R is ($C_2$-$C_8$)alkyl or ($C_2$-$C_8$)alkenyl substituted with one or more independently selected ($C_6$-$C_{15}$)aryl or ($C_5$-$C_{15}$)heteroaryl; and $R^1$ is hydrogen, or ($C_2$-$C_8$)alkyl or ($C_2$-$C_8$)alkenyl substituted with one or more independently selected ($C_6$-$C_{15}$)aryl or ($C_5$-$C_{15}$)heteroaryl. Values for the remaining variables are as described in the first embodiment.

In a second aspect of the first embodiment, A is *—OC (O)—. Values for the remaining variables are as described in the first embodiment, or first aspect thereof.

In a third aspect of the first embodiment, A is *—N($R^1$) C(O)—. Values for the remaining variables are as described in the first embodiment, or first or second aspect thereof.

In a fourth aspect of the first embodiment, A is *—O ($CH_2$)—. Values for the remaining variables are as described in the first embodiment, or first through third aspects thereof.

In a fifth aspect of the first embodiment, R is ($C_2$-$C_5$)alkyl or ($C_2$-$C_5$)alkenyl substituted with one or more independently selected ($C_6$-$C_{15}$)aryl or ($C_5$-$C_{15}$)heteroaryl. Values for the remaining variables are as described in the first embodiment, or first through fourth aspects thereof.

In a sixth aspect of the first embodiment, R is ($C_2$-$C_5$) alkyl substituted with one or two independently selected ($C_6$-$C_{15}$)aryl. Values for the remaining variables are as described in the first embodiment, or first through fifth aspects thereof.

In a seventh aspect of the first embodiment, $R^1$ is hydrogen. Values for the remaining variables are as described in the first embodiment, or first through sixth aspects thereof.

In an eighth aspect of the first embodiment, each alkyl and alkenyl is further unsubstituted. Values for the variables are as described in the first embodiment, or first through seventh aspects thereof.

In a ninth aspect of the first embodiment, each aryl and heteroaryl is optionally and independently substituted with one or more $R^2$ independently selected from halo, ($C_1$-$C_3$) alkoxy, ($C_1$-$C_3$)haloalkoxy, ($C_1$-$C_3$)alkyl or ($C_1$-$C_3$)haloalkyl. Values for the remaining variables are as described in the first embodiment, or first through eighth aspects thereof.

In a tenth aspect of the first embodiment, R is ($C_2$-$C_8$) alkyl or ($C_2$-$C_8$)alkenyl substituted with one or more independently selected ($C_6$-$C_{15}$)aryl. Values for the remaining variables are as described in the first embodiment, or first through ninth aspects thereof.

In an eleventh aspect of the first embodiment, each ($C_6$-$C_{15}$)aryl is independently selected from phenyl or fluorenyl. Values for the remaining variables are as described in the first embodiment, or first through tenth aspects thereof.

In a twelfth aspect of the first embodiment, R and $R^1$ are the same. Values for the remaining variables are as described in the first embodiment, or first through eleventh aspects thereof.

In a thirteenth aspect of the first embodiment, each aryl and heteroaryl is optionally and independently substituted with one or more $R^2$ independently selected from halo, ($C_1$-$C_3$)alkoxy, ($C_1$-$C_3$)fluoroalkoxy, ($C_1$-$C_3$)alkyl or ($C_1$-$C_3$)fluoroalkyl. Values for the remaining variables are as described in the first embodiment, or first through twelfth aspects thereof.

In a fourteenth aspect of the first embodiment, R is ($C_2$-$C_5$)alkyl substituted with one or two independently selected ($C_6$-$C_{15}$)aryl or ($C_5$-$C_{15}$)heteroaryl. Values for the remaining variables are as described in the first embodiment, or first through thirteenth aspects thereof.

In a fifteenth aspect of the first embodiment, each ($C_5$-$C_{15}$)heteroaryl is independently selected from pyridinyl, pyrimidinyl or carbazolyl. Values for the remaining variables are as described in the first embodiment, or first through fourteenth aspects thereof.

In a sixteenth aspect of the first embodiment, A is *—OC (O)— or *—N($R^1$)C(O)—. Values for the remaining variables are as described in the first embodiment, or first through fifteenth aspects thereof.

In a seventeenth aspect of the first embodiment, R is ($C_2$-$C_3$)alkyl substituted with one or two independently selected ($C_6$-$C_{15}$)aryl or ($C_5$-$C_{15}$)heteroaryl. Values for the remaining variables are as described in the first embodiment, or first through sixteenth aspects thereof.

In an eighteenth aspect of the first embodiment, R is hydrogen, or ($C_2$-$C_8$)alkyl or ($C_2$-$C_8$)alkenyl substituted with one or more independently selected ($C_6$-$C_{15}$)aryl or ($C_5$-$C_{15}$)heteroaryl; and $R^1$ is hydrogen, or ($C_2$-$C_8$)alkyl or ($C_2$-$C_8$)alkenyl substituted with one or more independently selected ($C_6$-$C_{15}$)aryl or ($C_5$-$C_{15}$)heteroaryl. Values for the remaining variables are as described in the first embodiment, or first through seventeenth aspects thereof.

A second embodiment is a compound represented by the following structural formula:

(Ia)

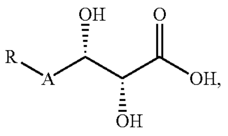

or a pharmaceutically acceptable salt thereof, wherein values for the variables (e.g., A, R) are as described in the first embodiment, or any aspect thereof.

A third embodiment is a compound represented by the following structural formula:

(Ia')

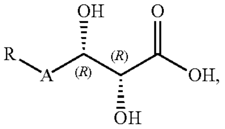

or a pharmaceutically acceptable salt thereof, wherein values for the variables (e.g., A, R) are as described in the first embodiment, or any aspect thereof.

In some aspects of any of the aforementioned embodiments or aspects thereof, the compound is not tartaric acid, or a salt (e.g., pharmaceutically acceptable salt) thereof. In some aspects of any of the aforementioned embodiments or aspects thereof, the compound is not (2R,3R)-2,3-dihydroxy-4-oxo-4-((1-phenylethyl)amino)butanoic acid, (2R,3R)-4-((1-(4-fluorophenyl)ethyl)amino)-2,3-dihydroxy-4-oxobutanoic acid, (2R,3R)-2,3-dihydroxy-4-oxo-4-((4-phenylbutyl)amino)butanoic acid, (2R,3R)-2,3-dihydroxy-4-oxo-4-(((S)-1-phenylpropyl)amino)butanoic acid or (2R,3R)-2,3-dihydroxy-4-(((R)-1-(naphthalen-1-yl)ethyl)amino)-4-oxobutanoic acid, or a salt (e.g., pharmaceutically acceptable salt) of any of the foregoing. In some aspects of any of the aforementioned embodiments or aspects thereof, the compound is not tartaric acid, (2R,3R)-2,3-dihydroxy-4-oxo-4-((1-phenylethyl)amino)butanoic acid, (2R,3R)-4-((1-(4-fluorophenyl)ethyl)amino)-2,3-dihydroxy-4-oxobutanoic acid, (2R,3R)-2,3-dihydroxy-4-oxo-4-((4-phenylbutyl)amino)butanoic acid, (2R,3R)-2,3-dihydroxy-4-oxo-4-(((S)-1-phenylpropyl)amino)butanoic acid or (2R,3R)-2,3-dihydroxy-4-(((R)-1-(naphthalen-1-yl)ethyl)amino)-4-oxobutanoic acid, or a salt (e.g., pharmaceutically acceptable salt) of any of the foregoing.

Examples of compounds of the structural formulas depicted herein include compounds A-F, depicted in Table 1. One embodiment provides compound A, B or C, or a pharmaceutically acceptable salt of any of the foregoing. One embodiment provides compound A, B, C, D or E, or a pharmaceutically acceptable salt of any of the foregoing. One embodiment provides compound A, B, C, D, E, F or G, or a pharmaceutically acceptable salt of any of the foregoing.

TABLE 1

| Compound Identifier | Compound Structure | Compound Name |
|---|---|---|
| A | 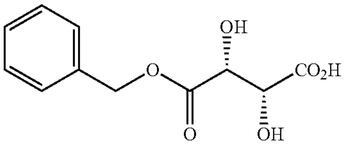 [SMILES: O=C(O)[C@H](O)[C@@H](O)C(=O)OCc1ccccc1] | (2R,3R)-4-(benzyloxy)-2,3-dihydroxy-4-oxobutanoic acid |
| B | 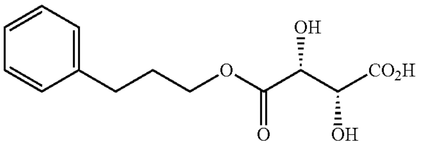 [SMILES: O=C(O)[C@H](O)[C@@H](O)C(=O)OCCCc1ccccc1] | (2R,3R)-2,3-dihydroxy-4-oxo-4-(3-phenylpropoxy)butanoic acid |
| C | 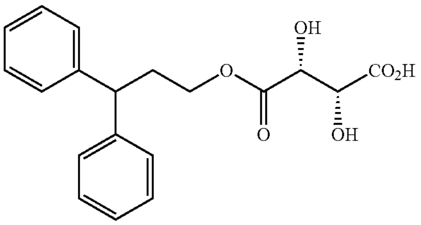 [SMILES: O=C(O)[C@H](O)[C@@H](O)C(=O)OCCC(c1ccccc1)c1ccccc1] | (2R,3R)-4-(3,3-diphenylpropoxy)-2,3-dihydroxy-4-oxobutanoic acid |
| D | 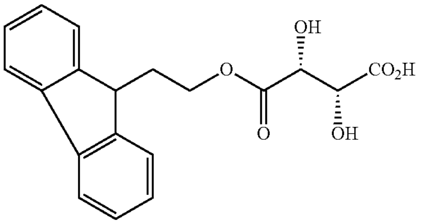 [SMILES: O=C(O)[C@H](O)[C@@H](O)C(=O)OCCC1c2ccccc2-c2ccccc21] | (2R,3R)-4-(2-(9H-fluoren-9-yl)ethoxy)-2,3-dihydroxy-4-oxobutanoic acid |
| E | 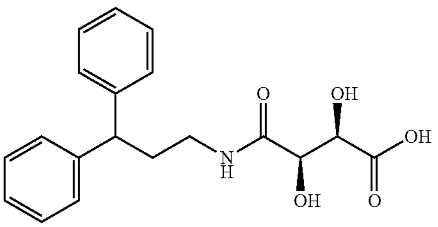 [SMILES: O=C(O)[C@H](O)[C@@H](O)C(=O)NCCC(c1ccccc1)c1ccccc1] | (2R,3R)-4-((3,3-diphenylpropyl)amino)-2,3-dihydroxy-4-oxobutanoic acid |

TABLE 1-continued

| Compound Identifier | Compound Structure | Compound Name |
|---|---|---|
| F | 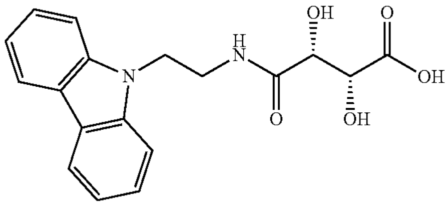 [SMILES: O=C(O)[C@H](O)[C@@H](O)C(=O)NCCn1c2ccccc2c2ccccc21] | (2R,3R)-4-((2-(9H-carbazol-9-yl)ethyl)amino)-2,3-dihydroxy-4-oxobutanoic acid |
| G | 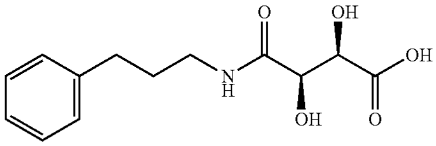 [SMILES: O=C(O)[C@H](O)[C@@H](O)C(=O)NCCCc1ccccc1] | (2R,3R)-2,3-dihydroxy-4-oxo-4-((3-phenylpropyl)amino)butanoic acid |

Compositions and Kits

Typically, for administration to a subject, a compound of the disclosure is formulated with one or more pharmaceutically acceptable carriers. The disclosure provides such compositions, including pharmaceutical compositions. Thus, one embodiment is a composition (e.g., pharmaceutical composition) comprising a compound of the disclosure and a pharmaceutically acceptable carrier. The compositions described herein can be used in the methods described herein, e.g., to supply a compound of the disclosure.

Compounds and compositions described herein can also be in the form of formulations of lipid particles, such as liposomal formulations. Thus, one embodiment is a lipid particle (e.g., a liposome) comprising a compound of the disclosure. One embodiment is a composition comprising a plurality of lipid particles (e.g., a plurality of lipid particles comprising a compound of the disclosure) in a pharmaceutically acceptable carrier.

As used herein, "lipid particle" refers to a particle comprising at least one lipid, e.g., a phospholipid. Examples of lipid particles include, liposomes, micelles and lipid nanoparticles. Lipid particles, such as liposomes, can be unilamellar or multilamellar. In some aspects, a lipid particle is a liposome. In some aspects, a lipid particle is a lipid nanoparticle.

Examples of phospholipids include dimyristoylphosphatidylcholine (DMPC), phosphatidylserine (PS), phosphatidylcholine (PC), phosphatidylethanolamine, phosphatidyl inositol, bisphosphatidyl glycerol, phosphatidic acid, phosphatidyl alcohol and/or phosphatidyl glycerol. Phospholipids can be obtained from various sources, both natural and synthetic. For example, PS can be obtained from porcine brain PS or plant-based soy (soya bean) PS. Egg PC and PS and synthetic PC are available commercially.

Typically, the molar percentage of a compound of the disclosure in a lipid particle (e.g., liposome) comprising a compound of the disclosure will be from about 1% to about 50%, e.g., from about 5% to about 50%, from about 15% to about 40%, from about 25% to about 35%, about 25%, about 30% or about 35%.

A compound of the disclosure can be encapsulated within a lipid particle, such as a liposome, described herein, bound (covalently or non-covalently) to a lipid head group or, preferably, embedded, in whole or in part, covalently or non-covalently, in a lipid bilayer (e.g., of a liposome). Without wishing to be bound by any particular theory, it is believed that compounds of the disclosure wherein R and/or $R^1$ is substituted with an aryl may embed in a lipid bilayer of a liposome. Further, it is believed that the aryl may embed so as to leave the tartaric acid residue of the compound of the disclosure exposed to the exterior of the liposome, thereby mimicking the natural surface presentation of, for example, PS.

Compositions described herein and, hence, compounds of the disclosure, may be administered orally, parenterally (including subcutaneously, intramuscularly, intravenously and intradermally), by inhalation spray, topically, rectally, nasally, buccally, vaginally or via an implanted reservoir. The terms "parenteral" and "parenterally," as used herein, include subcutaneous, intracutaneous, intravenous, intramuscular, intraocular, intravitreal, intra-articular, intra-arterial, intra-synovial, intrasternal, intrathecal, intralesional, intrahepatic, intraperitoneal, intralesional and intracranial injection or infusion techniques. In some aspects, a composition described herein is administrable intravenously and/or intraperitoneally. In some aspects, a composition described herein is administrable orally. In some aspects, a composition described herein is administrable intravenously. Preferably, a composition described herein is administered orally, subcutaneously, intraperitoneally or intravenously.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some aspects, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a)

fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Liquid dosage forms for oral administration include pharmaceutically acceptable emulsions, microemulsions, solutions, suspensions, syrups, and elixirs. In addition to the compound of the disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the disclosure can also be in micro-encapsulated form with one or more excipients, as noted above. In such solid dosage forms, the compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another aspect, a compound of the disclosure can be provided in an extended (or "delayed" or "sustained") release composition. This delayed-release composition comprises the compound of the disclosure and a delayed-release component. Such a composition allows targeted release of the compound, for example, into the lower gastrointestinal tract, for example, into the small intestine, the large intestine, the colon and/or the rectum. In certain aspects, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition can provide controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered subcutaneously, intraperitoneally or intravenously. Compositions described herein for intravenous, subcutaneous, or intraperitoneal injection may contain an isotonic vehicle such as sodium chloride injection, Ringer's injection, dextrose injection, dextrose and sodium chloride injection, lactated Ringer's injection, or other vehicles known in the art.

Compositions described herein can also be administered in the form of suppositories for rectal administration. These can be prepared by mixing a compound of the disclosure with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration of a compound described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. Suitable carriers also include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents. Without wishing to be bound by any particular theory, it is believed that local delivery of a composition described herein, as can be achieved by nasal aerosol or inhalation, for example, can reduce the risk of systemic consequences of the composition, for example, consequences for red blood cells.

The amount of a compound of the disclosure that can be combined with the carrier materials to produce a composition in a single dosage form will vary depending, for example, upon the subject treated, the particular mode of administration and the activity of the agent employed. Preferably, compositions should be formulated so that a dosage (e.g., an IV dosage) of from about 0.01 mg/kg to about 1,000 mg/kg body weight/day, e.g., from about 0.01 mg/kg to about 100 mg/kg body weight/day or from about 0.02 mg/kg to about 200 mg/kg of the compound, or pharmaceutically acceptable salt thereof, can be administered to a subject receiving the composition. These dosages can be adjusted to account for bioavailability of the compound or pharmaceutically acceptable salt thereof via other routes of administration, such as the oral route.

The desired dose may conveniently be administered in a single dose or as multiple doses administered at appropriate intervals such that, for example, the agent is administered 1, 2, 3, 4, 5, 6 or more times per day. The daily dose can be divided, especially when relatively large amounts are administered, or as deemed appropriate, into several, for example 2, 3, 4, 5, 6 or more, administrations. In some aspects, a compound of the disclosure or composition described herein is administered once per day (QD), twice per day (BID), three times per day, four times per day or five times per day (e.g., QD or BID). In some aspects, a compound of the disclosure or composition described herein is administered daily, for example, once per day (QD), twice per day (BID), three times per day, four times per day, five times per day (e.g., QD, BID).

It should also be understood that a specific dosage and treatment regimen for any particular subject will depend upon a variety of factors, including the activity of the specific agent employed, the age, body weight, general health, sex, diet, time of administration, rate of excretion, drug combination, the judgment of the treating physician and the severity of the particular disease or disorder being treated. The amount of a compound of the disclosure in the composition will also depend upon the particular compound in the composition.

Other pharmaceutically acceptable carriers that can be used in the compositions described herein include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

In some aspects, a composition described herein further includes one or more additional therapeutic agents, e.g., for use in combination with a compound of the disclosure. When a composition comprises a compound of the disclosure and one or more additional therapeutic agents, each agent should be present at a dosage level of between about 1% and about 100% and, more preferably, between about 5% and about 95% of the dosage normally administered in a monotherapy regimen. Additional therapeutic agents for inclusion in a composition described herein include any of those described herein in connection with combination therapy.

In some aspects, the concentration of one or more therapeutic agents provided in a pharmaceutical composition is less than 100%, 90%, 80%, 70%, 60%, 50%, 40%, 30%, 20%, 19%, 18%, 17%, 16%, 15%, 14, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v; and/or greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some aspects, the concentration of one or more therapeutic agents provided in a pharmaceutical composition is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% w/w, w/v or v/v. In some embodiments, the concentration of one or more therapeutic agents provided in a pharmaceutical composition is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v.

The compositions described herein can, for example, be administered in a dosage ranging from about 0.5 mg/kg to about 100 mg/kg of body weight or, alternatively, in a dosage ranging from about 1 mg/dose to about 1000 mg/dose, every 4 to 120 hours, or according to the requirements of the particular drug. Doses lower or higher than those recited above may be required. Specific dosage and treatment regimens for any particular patient will depend, for example, upon a variety of factors, including the activity of the specific agent employed, the age, body weight, general health status, sex, diet, time of administration, rate of excretion, drug combination, the severity and course of the disease, condition or symptoms, the subject's disposition to the disease, condition or symptoms, and the judgment of the treating physician. Typically, the compositions will be administered from about 1 to about 6 (e.g., 1, 2, 3, 4, 5 or 6) times per day or, alternatively, as an infusion (e.g., a continuous infusion).

The compositions described herein can be provided in unit dosage form. The amount of active ingredient that can be combined with a carrier to produce a unit dosage form will vary depending, for example, upon the subject being treated and the particular mode of administration. Typically, a unit dosage form will contain from about 1 to about 2,500 mg of active ingredient(s) (e.g., compound of the disclosure), e.g., from about 1 to about 2,000 mg, from about 1 to about 1,000 mg, from about 1 to about 500 mg, from about 1 to about 250 mg, from about 1 to about 150 mg, from about 0.5 to about 100 mg, or from about 1 to about 50 mg of active ingredient(s).

One embodiment is a combination (e.g., pharmaceutical combination) comprising a compound of the disclosure and one or more additional therapeutic agents, e.g., for use in combination with a compound of the disclosure. Additional therapeutic agents for a combination described herein include any of those described herein in connection with combination therapy.

One embodiment is a kit comprising a compound of the disclosure (e.g., a composition described herein comprising a compound of the disclosure) and an additional therapeutic agent(s) (e.g., a composition comprising an additional therapeutic agent(s)). In one aspect, the kit comprises a therapeutically effective amount of the compound of the disclosure to treat a disease, disorder or condition described herein, and a therapeutically effective amount of the additional therapeutic agent(s) to treat the disease, disorder or condition. In some aspects, the kit further comprises written instructions for administering the compound of the disclosure and/or the additional agent(s) to a subject to treat a disease, disorder or condition described herein. Additional therapeutic agents for a kit described herein include any of those described herein in connection with combination therapy.

Methods of Use

It has now been found that various tartaric acid analogs disclosed herein have the capacity to reduce and/or reverse the tolerogenic effect of PS on the antitumor activity of T-cells and restore T-cell proliferation in cells treated with PS, suggesting that the analogs act as antagonists/partial-antagonists for at least the tolerogenic effect of PS on TIM4 and TIM3. Various tartaric acid analogs disclosed herein have now also been found to reverse the inhibitory effects of PS on Granzyme B and IFN-γ, which are primarily secreted by activated T-cells. Finally, various tartaric acid analogs disclosed herein have been found to reduce immune checkpoints and exhaustion markers, including TIM3, PD-1, CTLA4, KLRG-1, Lag-3 and TIGIT.

Accordingly, one embodiment is a method of promoting the survival, proliferation or activity of an immune cell, comprising contacting the immune cell with a compound of the disclosure (e.g., a therapeutically effective amount of a compound of the disclosure).

Another embodiment is a method of inhibiting immune cell anergy, comprising contacting an immune cell with a compound of the disclosure (e.g., a therapeutically effective amount of a compound of the disclosure).

Yet another embodiment is a method of inhibiting regulatory T cells or myeloid-derived suppressor cells, comprising contacting a regulatory T cell or myeloid-derived suppressor cell with a compound of the disclosure (e.g., a therapeutically effective amount of a compound of the disclosure).

Another embodiment is a method of activating an immune cell, comprising contacting the immune cell with a compound of the disclosure (e.g., a therapeutically effective amount of a compound of the disclosure).

Another embodiment is a method of modulating (e.g., inhibiting) the activity of phosphatidyl serine (PS, e.g., as by binding to a T cell immunoglobulin and mucin domain (TIM) receptor, and thereby inhibiting and/or outcompeting binding of PS to the TIM receptor), comprising contacting a cell with a compound of the disclosure (e.g., a therapeutically effective amount of a compound of the disclosure).

Another embodiment is a method of modulating (e.g., inhibiting) the expression or activity of a T cell immunoglobulin and mucin domain (TIM) receptor (e.g., antagonizing, e.g., wholly or partially, the tolerogenic effect of PS on a TIM receptor), comprising contacting a cell (e.g., a cell expressing a TIM receptor, such as an immune cell) with a compound of the disclosure (e.g., a therapeutically effective amount of a compound of the disclosure). TIM receptors are type 1 cell-surface glycoproteins, and TIM1, TIM3 and TIM4, TIM receptors expressed in humans, have been identified as phosphatidylserine receptors. TIM1 is preferentially expressed on T-helper 2 cells, and operates as a potent costimulatory molecule for T-cell activation. TIM3 is preferentially expressed on T-helper 1 cells, type 1 T-cells and dendritic cells, and generates an inhibitory signal resulting in apoptosis of T-helper 1 cells and type 1 T-cells. TIM3 is also expressed on cytotoxic T-cells (e.g., CD8+), and generates an inhibitory signal resulting in apoptosis of cytotoxic T-cells (e.g., CD8+). TIM4 is expressed on antigen-presenting cells, and mediates phagocytosis of apoptotic cells, thereby promoting tolerance. In some aspects, the TIM receptor is a TIM3 receptor. In some aspects, the TIM receptor is a TIM4 receptor. In some aspects, the TIM receptor is a TIM1 receptor. "TIM" is also referred to, for example, in the literature, as "Tim".

Another embodiment is a method of modulating (e.g., inhibiting) the expression or activity of an immune checkpoint, comprising contacting an immune cell with a compound of the disclosure (e.g., a therapeutically effective amount of a compound of the disclosure). Examples of immune checkpoints include PD-1, PD-L1, LAG-3, TIM3, TIM4, TIGIT, VISTA, KLRG-1 and CTLA4. In some aspects, an immune checkpoint is a TIM receptor, such as TIM3 or TIM4. In some aspects, an immune checkpoint is PD-1, PD-L1 or CTLA4.

Another embodiment is a method of modulating (e.g., promoting, inducing, stimulating) production of tumor necrosis factor alpha (TNFα), comprising contacting a cell with a compound of the disclosure (e.g., a therapeutically effective amount of a compound of the disclosure). In some aspects, production of TNFα is modulated (e.g., promoted, induced, stimulated) without promoting production of tumor growth factor beta (TGFβ).

Another embodiment is a method of promoting the expression or activity of a cytolytic molecule, comprising contacting the immune cell with a compound of the disclosure (e.g., a therapeutically effective amount of a compound of the disclosure). Examples of cytolytic molecules include interferon gamma, granzyme A, granzyme B, granzyme K and perforin. In some aspects, the cytolytic molecule is interferon gamma, granzyme A, granzyme B, granzyme K or perforin.

Another embodiment is a method of inducing or maintaining central memory phenotype of an immune cell, comprising contacting the immune cell with a compound of the disclosure (e.g., a therapeutically effective amount of a compound of the disclosure).

Another embodiment is a method of inhibiting the expression or activity of an exhaustion marker, comprising contacting an immune cell with a compound of the disclosure (e.g., a therapeutically effective amount of a compound of the disclosure). Examples of exhaustion markers include TIM3, TIM4, PD-1, CTLA4, Lag-3 and KLRG1. In some aspects, the exhaustion marker is TIM3, TIM4, PD-1, CTLA4, Lag-3 or KLRG1.

Another embodiment is a method of enhancing cytotoxicity of a cytotoxic agent, comprising contacting a cell (e.g., immune cell) with a compound of the disclosure (e.g., a therapeutically effective amount of a compound of the disclosure). In some aspects, the cell is exposed to the cytotoxic agent in combination with the compound of the disclosure. In some aspects, the method further comprises contacting the cell with the cytotoxic agent, e.g., such that the cell is exposed to the cytotoxic agent in combination with the compound of the disclosure.

In some aspects of the methods described herein, the cell is an immune cell, e.g., a T-cell, a natural killer (NK) cell, a macrophage, a neutrophil, a myeloid-derived suppressor cell or a dendritic cell. In some aspects, an immune cell is $CD8^+$, such as a $CD8^+$ T-cell.

In some aspects of the methods described herein, the method is conducted in vitro. In other aspects of the methods described herein, the method is conducted in vivo. In some aspects, therefore, the cell (e.g., immune cell) is in a subject (e.g., a subject having a disease, disorder or condition described herein). Thus, in some aspects, the method comprises administering to a subject in need thereof a therapeutically effective amount of a compound of the disclosure.

Another embodiment is a method of treating a cancer in a subject in need thereof, comprising administering to the subject a therapeutically effective amount of a compound of the disclosure. In some aspects, the cancer is a hematological malignancy, e.g., a leukemia, such as acute lymphocytic leukemia (ALL), chronic lymphocytic leukemia (CLL), acute myeloid leukemia (AML) or chronic myeloid leukemia (CML), a myeloma, a lymphoma. In some aspects, the cancer comprises (e.g., is) a solid tumor.

Specific examples of cancer treatable according to the methods described herein include Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some embodiments, the cancer is a metastatic cancer.

In some embodiments, the cancer is resistant.

In some embodiments, the cancer is melanoma, non-small cell lung cancer, malignant pleural mesothelioma, renal cell carcinoma, Hodgkin's lymphoma, squamous cell carcinoma of the head and neck, urothelial carcinoma, colorectal cancer, hepatocellular carcinoma (e.g., cutaneous squamous cell carcinoma), esophageal cancer, gastric cancer, gastroesophageal junction cancer, esophageal adenocarcinoma, primary mediastinal large B-cell lymphoma, microsatellite instability-high (MSI-H) or mismatch repair deficient (dMMR) cancer (e.g., MSI-H or dMMR solid tumors, such as colorectal cancer), cervical cancer, Merkel cell carcinoma, endometrial carcinoma, tumor mutational burden-high (TMB-H) cancer (e.g., TMB-H solid tumors) or triple negative breast cancer. In some embodiments, the cancer is melanoma (e.g., metastatic melanoma). Tumor mutational burden-high cancers typically have ≥10 mutations/megabase (mut/Mb), as determined by an FDA-approved test.

A compound of the disclosure can also be administered in combination with one or more other therapies (e.g., radiation therapy, a chemotherapy, such as a chemotherapeutic or cytotoxic agent; an immunotherapy, such as an immunotherapeutic agent) to treat a disease, disorder or condition. When administered "in combination," the compound of the disclosure can be administered before, after or concurrently with the other therapy(ies) (e.g., radiation therapy, an additional therapeutic agent(s)). When co-administered simultaneously (e.g., concurrently), the compound of the disclosure and another therapeutic agent can be in separate formulations (as, for example, in a pharmaceutical combination comprising a compound of the disclosure and an additional therapeutic agent(s)) or the same formulation (as, for example, in a pharmaceutical composition comprising a compound of the disclosure and an additional therapeutic agent(s)). Alternatively, the compound of the disclosure and another therapeutic agent can be administered sequentially, either at approximately the same time or at different times, as separate compositions. When the compound of the disclosure and the other therapy (e.g., therapeutic agent) are administered as separate formulations or compositions, the compound of the disclosure and the other therapy can be administered by the same route of administration or by different routes of administration. A skilled clinician can determine appropriate timing for administration of each therapy being used in combination (e.g., timing sufficient to allow an overlap of the pharmaceutical effects of the therapies). Typically, a combination therapy will provide beneficial effects of the drug combination in treating the diseases, conditions or disorders described herein.

In some aspects, a method described herein further comprises administering to the subject (e.g., a therapeutically effective amount of) an additional therapy(ies) (e.g., radiation therapy, an additional therapeutic agent, such as a chemotherapeutic or cytotoxic agent, an immunotherapeutic agent, an antibody, such as a monoclonal antibody), e.g., in combination with the compound of the disclosure. In some aspects, the compound of the disclosure is administered before the additional therapy(ies). In some aspects, the compound of the disclosure is administered after the additional therapy(ies). In some aspects, the compound of the disclosure is administered concurrently with the additional therapy(ies).

In some aspects, a method further comprises administering to a subject an immune checkpoint inhibitor (e.g., a therapeutically effective amount of an immune checkpoint inhibitor). Examples of immune checkpoint inhibitors include PD-1 inhibitors, such as pembrolizumab, nivolumab and cemiplimab; PD-L1 inhibitors, such as atezolizumab, avelumab and durvalumab; and CTLA-4 inhibitors, such as ipilimumab. In some aspects, an immune checkpoint inhibitor is a PD-1 inhibitor, PD-L1 inhibitor or CTLA-4 inhibitor. In some aspects, an immune checkpoint inhibitor is pembrolizumab, nivolumab or ipilimumab. In some aspects, an immune checkpoint inhibitor is nivolumab or ipilimumab.

For example, a compound of the disclosure can be administered in combination with nivolumab (e.g., to treat melanoma, renal cell carcinoma, hepatocellular carcinoma, NSCLC, malignant pleural mesothelioma, colorectal cancer); nivolumab and platinum-doublet chemotherapy (e.g., to treat NSCLC); ipilimumab (e.g., to treat melanoma, renal cell carcinoma, hepatocellular carcinoma, NSCLC, malignant pleural mesothelioma, colorectal cancer); ipilimumab and platinum-doublet chemotherapy (e.g., to treat NSCLC).

In some aspects, a method further comprises administering to a subject a cytotoxic agent (e.g., a therapeutically effective amount of a cytotoxic agent). Examples of cytotoxic agents include alkylating agents (e.g., cyclophosphamide, mechlorethamine, chlorambucil, melphalan, dacarbazine, nitrosoureas, temozolomide, altretamine, bendamustine, busulfan, platinum-based agents, ifosfamide, thiotepa, trabectedin); anthracyclines (e.g., daunorubicin, doxorubicin, epirubicin, idarubicin, valrubicin); taxanes (e.g., paclitaxel, nab-paclitaxel, docetaxel, cabazitaxel, abraxane, taxotere); epothilones; histone deacetylase inhibitors (e.g., vorinostat, romidepsin); topoisomerase inhibitors (e.g., topoisomerase type I inhibitors, such as irinotecan, topotecan; topoisomerase type II inhibitors, such as etoposide, mitoxantrone, teniposide, tafluposide); kinase inhibitors (e.g., axitinib, bortezomib, cabozantinib, erlotinib, gefitinib, imatinib, lenvatinib, vemurafenib, vismodegib); nucleotide analogs (e.g., azacitidine, azathioprine, capecitabine, cytarabine, doxifluridine, floxuridine, fluorouracil, gemcitabine, hydroxyurea, mercaptopurine, methotrexate, tioguanine); peptide antibiotics (e.g., bleomycin, actinomycin); platinum-based agents (e.g., carboplatin, cisplatin, oxaliplatin); retinoids (e.g., tretinoin, alitretinoin, bexarotene); and *vinca* alkaloids (e.g., vinblastine, vincristine, vindesine, vinorelbine). Further examples of cytotoxic agents include anti-metabolites (e.g., azacitidine, 5-FU, 6-mercaptopurine, capecitabine, cladribine, clofarabine, cytarabine (e.g., Ara-C), decitabine, floxuridine, fludarabine, gemcitabine, hydroxyurea, methotrexate, nelarabine, pemetrexed, pentostatin, pralatrexate, thioguanine, trifluridine and tipiracil); anti-tumor antibiotics (e.g., anthracyclines, mitoxantrone, bleomycin, dactinomycin, mitomycin C); corticosteroids (e.g., prednisone, methylprednisolone, dexamethasone); and nitrosoureas (e.g., carmustine, lomustine, streptozocin). Yet further examples of cytotoxic agents include all-trans retinoic acid, arsenic trioxide, asparaginase, eribulin, hydroxyurea, ixabepilone, mitotane, omacetaxine, pegaspargase, procarbazine, romidepsin and vorinostat. In some aspects, a cytotoxic agent is a platinum-based agent (e.g., carboplatin), an anti-metabolite (e.g., pemetrexed), a taxane (e.g., paclitaxel, paclitaxel protein-bound), a nucleotide analog (e.g., a fluoropyrimidine, such as capecitabine, floxuridine, fluorouracil) or a kinase inhibitor (e.g., axitinib, cabozantinib, lenvatinib).

In some aspects, a method further comprises administering to a subject platinum-doublet chemotherapy (e.g., a therapeutically effective amount of platinum-doublet chemotherapy). Platinum-doublet chemotherapy typically refers to chemotherapy comprising a platinum-based agent (e.g., cisplatin, carboplatin) and an additional cytotoxic agent (e.g., vinorelbine, gemcitabine or a taxane).

In some aspects, the one or more additional therapeutic agents (e.g., cytotoxic agents) includes a platinum-based agent (e.g., carboplatin), an anti-metabolite (e.g., pemetrexed), a taxane (e.g., paclitaxel, paclitaxel protein-bound), a nucleotide analog (e.g., a fluoropyrimidine (e.g., capecitabine, floxuridine, fluorouracil)), trastuzumab, bevacizumab or a kinase inhibitor (e.g., axitinib, cabozantinib, lenvatinib), or a combination of the foregoing. For example, a compound of the disclosure can be administered in combination with pemetrexed and a platinum-based agent (e.g., to treat NSCLC); carboplatin and paclitaxel or paclitaxel protein-bound (e.g., to treat NSCLC); platinum and fluorouracil (e.g., to treat head and neck squamous cell cancer); trastuzumab, a fluoropyrimidine and a platinum-based agent (e.g., to treat gastric cancer); a fluoropyrimidine and a platinum-based agent (e.g., to treat gastric cancer, gastroesophageal junction cancer, esophageal adenocarcinoma); a cytotoxic agent, with or without bevacizumab (e.g., to treat cervical cancer, TNBC); axitinib (e.g., to treat renal cell carcinoma); lenvatinib (e.g., to treat renal cell carcinoma, endometrial carcinoma); cabozantinib (e.g., to treat renal cell carcinoma); a platinum-based agent (e.g., to treat urothelial carcinoma).

Another embodiment is a method of enhancing cytotoxicity of a cytotoxic agent (e.g., a cytotoxic agent described herein) in a subject in need thereof (e.g., a subject having a cancer, such as a cancer described herein, a subject being treated with the cytotoxic agent), comprising administering to the subject a therapeutically effective amount of a compound of the disclosure. In some aspects, the subject is receiving the cytotoxic agent in combination with the compound of the disclosure. In some aspects, the compound of the disclosure is administered before the subject receives the cytotoxic agent. In some aspects, the compound of the disclosure is administered after the subject receives the cytotoxic agent. In some aspects, the compound of the disclosure is administered concurrently with the subject receiving the cytotoxic agent. In some aspects, the method further comprises administering the cytotoxic agent to the subject, e.g., after, before or concurrently with the compound of the disclosure.

Cytotoxic agent(s) useful in methods of enhancing cytotoxicity of a cytotoxic agent (e.g., in a subject in need thereof) include those cytotoxic agents described herein in connection with combination therapy.

Another embodiment is a method of inhibiting metastasis of a cancer (e.g., a cancer described herein) in a subject in need thereof, comprising administering to the subject a therapeutically effective amount of a compound of the disclosure.

Another embodiment is a method of reducing metastases in a subject having a metastatic cancer (e.g., a cancer described herein), comprising administering to the subject a therapeutically effective amount of a compound of the disclosure.

Another embodiment is a method of promoting tumor regression in a subject in need thereof (e.g., a subject having a cancer, such as a cancer described herein), comprising administering to the subject a therapeutically effective amount of a compound of the disclosure.

A compound of the disclosure or other therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound or agent.

In some embodiments, administration (e.g., of a compound of the disclosure) is oral. In some embodiments, administration (e.g., of a compound of the disclosure) is intravenous.

EXEMPLIFICATION

Example 1. Structure-Activity Relationship: L-(+)-Tartaric Acid

It is shown that L-(+)-tartaric acid (TTA) can mimic the effects of O-phospho-L-serine (OPLS) on TNF-α production, but not TGF-β production.

RAW 264.7 cells were prepared, cultured, and dosed as described herein. The RAW 264.7 cell line is an immortalized mouse monocyte macrophage that is very close to primary cells, easy to maintain with minimum manipulation, and known to express TIM4. Briefly, cells were seeded at $4\times10^5$ cells/well. OPLS and TTA were dosed at 100, 70, 50, 30, 10, 3, 1, 0.3, 0.1, 0.03, 0.01, 0.003, 0.001, 0.0003 and 0.0001 mM. Finally, 100 μl of 40 μg/ml of human FVIII as a sample antigen was added to each well. LPS and free protein were used as positive and baseline controls, respectively. OPLS and TTA were formulated in RPMI media in aseptic conditions. The pH was adjusted to approximately 7.5 before dosing cells.

Figure 1B:
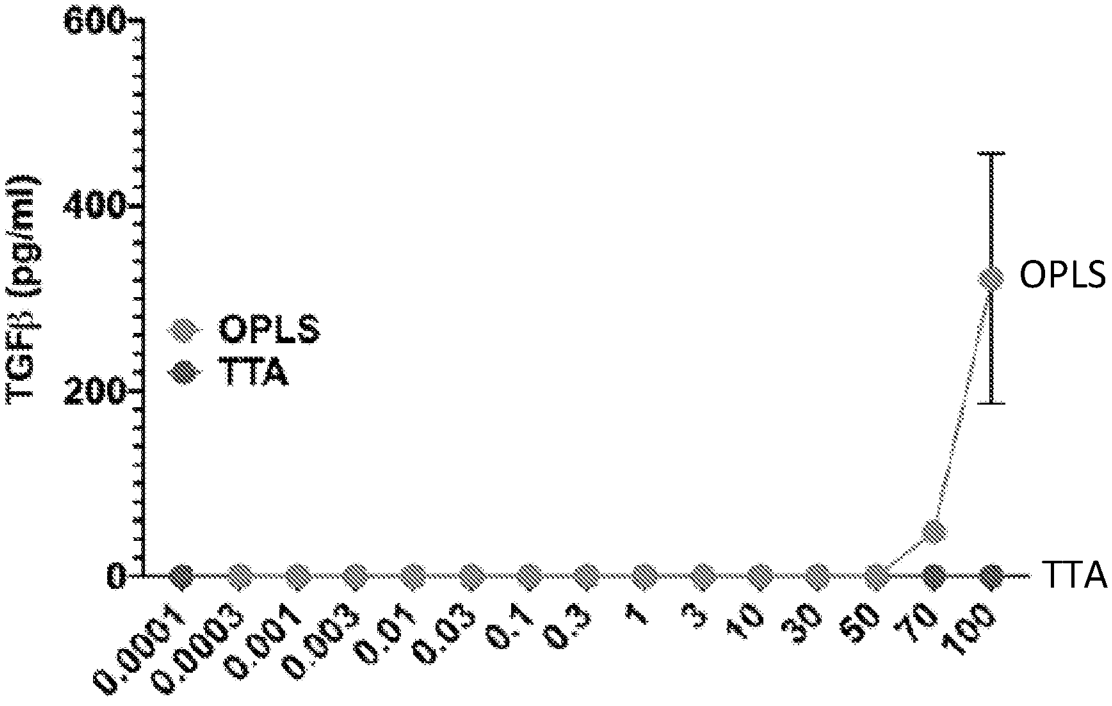
FIG. 1B shows dose-response of TGF-β after exposure to different doses of OPLS or TTA.

TNF-α and TGF-β ELISAs were conducted as per the manufacturer's instructions (TNF-α ELISA kit: R&D systems DY410; TGF-β ELISA kit: R&D systems DY1679). FIGS. 1A and 1B show that TTA can stimulate TNF-α production without stimulating TGF-β production. These data suggest that TTA may be a partial antagonist of the same receptor that binds OPLS (TIM).

Example 2. Survival, Proliferation and PD-1/TIM Expression in Phosphatidyl Serine (PS)-Treated Human CD8+ T-Cells in the Presence and Absence of L-(+)-Tartaric Acid The presence of phosphatidylserine (PS) in ovarian tumor ascites fluids has been shown to arrest the T-cell signaling cascade and inhibit T-cell activation. T-cell arrest was determined to be causally linked to PS, a naturally occurring phospholipid that is present on the outer leaflet of extracellular vesicles secreted by tumors. T-cell immunoglobulin- and mucin-domain-containing molecule (TIM) family of receptors have been identified as phosphatidylserine receptors. TIM receptors are expressed on macrophages and other antigen-presenting cells.

PS released by tumors into the tumor microenvironment can engage TIM receptors, which has been shown to attenuate the antitumor effect of CD8+ T-cells in tumor microenvironments and accelerate subsequent tumor growth. PS may also be responsible for the increased expression of TIM3 and TIM4 on tumor-infiltrating cells. Furthermore, some danger-associated molecular patterns (DAMPs) released from chemotherapy-damaged tumor cells can induce TIM4 expression.

PS/TIM4 binding has been confirmed by structural studies showing the hydrophilic head of PS penetrating the metal-ion-dependent ligand binding site formed between the characteristic CC loop and FG loop of the Ig domain of TIM4. L-(+)-Tartaric acid has also been shown to bind TIM4 and TIM3 receptors, and to compete with PS binding at the same site.

The effect of L-(+)-tartaric acid on proliferation and the antitumor cytotoxic effects of human CD8+ T cells in the presence of PS, a known inhibitor of CD8+ T cell proliferation and the antitumor cytotoxic effect, was studied.

30:70 PS:DMPC liposomes were synthesized in PBS. L-(+)-Tartaric acid was dissolved in RPMI media to the desired concentration, and pH was adjusted as needed to pH approximately 7.5. CD8+ T-cells were stained with CFSE (ThermoFisher Catalog No. 50-169-50), and prepared, cultured, and dosed as described herein. Briefly, cells were seeded at $4\times10^5$ cells/well. IL-2 (10 ng/ml) was used as a negative control, and ConA (20 μg/ml) in conjunction with IL-2 (10 ng/ml) was used as a positive control. After ConA stimulation (10 μg/ml) in the presence of 10 ng/ml IL-2, cells were dosed in duplicate with PS:DMPC liposomes to give a total of 100, 10, 1, or 0.1 mM of PS. For each dose of PS, L-(+)-tartaric acid was dosed at 70 or 100 mM. Flow cytometer analysis was performed to assess cell survival by viability dye and proliferation by CFSE (gated on survived CD8+ T-cells). Expression of PD-1 and TIM3 were also assessed by flow cytometry.

Cells were observed via a microscope at the end of the incubation period. It was observed that cells dosed with 100, 10, and 1 mM of PS-containing liposomes did not look healthy. Accordingly, cells dosed with 100, 10, and 1 mM of PS-containing liposomes were excluded from further analysis. Similarly, cells dosed with 100 mM of L-(+)-tartaric acid did not look healthy and were excluded from further analysis. Cells dosed with 0.1 mM PS and 70 mM L-(+)-tartaric acid looked healthy and were selected for flow cytometry analysis. Both controls (negative and ConA) looked healthy and were selected for flow analysis as well.

Figure 2A:
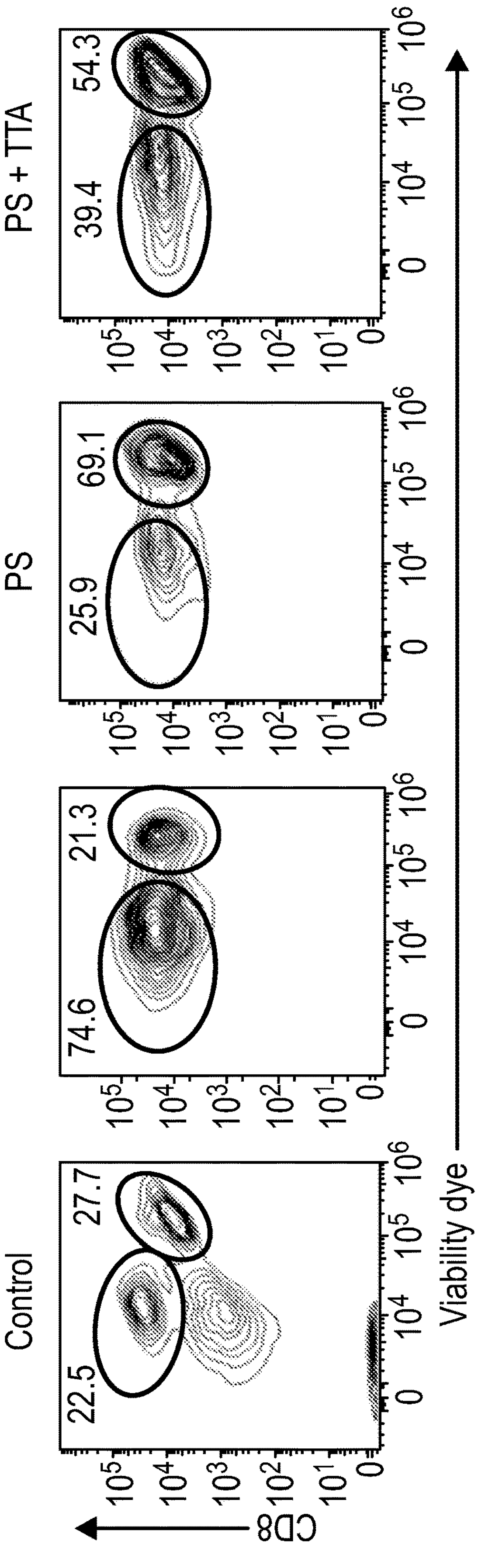
FIG. 2A shows cell survival by viability dye in phosphatidyl serine (PS)-treated CD8 T-cells in the presence or absence of TTA.

FIG. 2A shows that ConA enhanced CD8+ T-cells survival in comparison to the negative control (74.6% versus 22.5%). The addition of PS drastically decreased the survival of CD8+ T-cells. CD8+ T-cell survival dropped from 74.6% in ConA-treated cells to 25.9 in PS-treated cells. 70 mM L-(+)-Tartaric acid largely reduced the effects of 0.1 mM PS, increasing the frequency of viable CD8+ T cells to 39.4 from 25.9, a 65% increase compared to PS-treated cells alone.

Figure 2B:
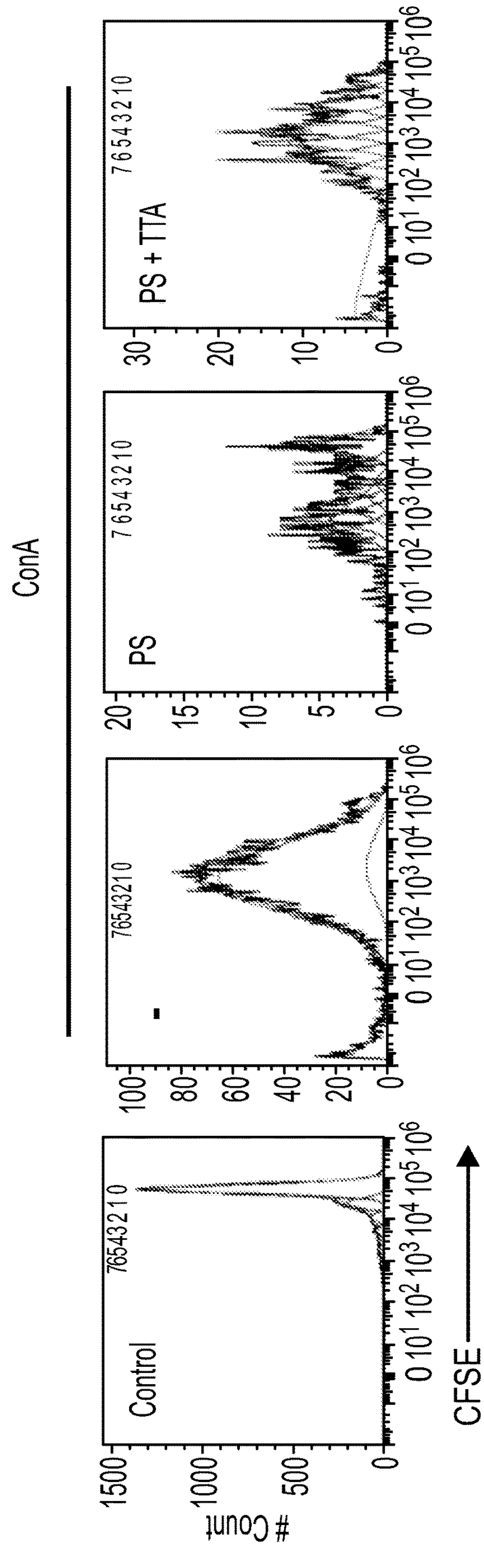
FIG. 2B shows CD8 T-cell proliferation as measured by carboxyfluorescein succinimidyl ester (CFSE) staining in PS-treated CD8 T-cells in the presence or absence of TTA.

FIG. 2B shows increased proliferation and accumulation of CD8+ T-cells upon stimulation with ConA, as evident from the single peak centered at $10^3$, compared to the negative control, where a single peak was right-shifted and centered between $10^4$ and $10^5$. Treatment with 0.1 mM PS negatively impacted the accumulation of CD8+ T-cells. Cells did expand for at least 7 generations, but CD8+ T-cells did not persist in the presence of PS. The double peaks observed in PS-treated group represent the population that proliferated similarly to ConA treated cells (left peak) and those that did not (right peak). 70 mM L-(+)-Tartaric acid partially reversed the effect of PS, and increased the survival and accumulation of CD8+ T cells, as evident from the single, left-shifted peak centered around $10^3$, which is similar to the peak observed in the ConA control.

Figure 2C:
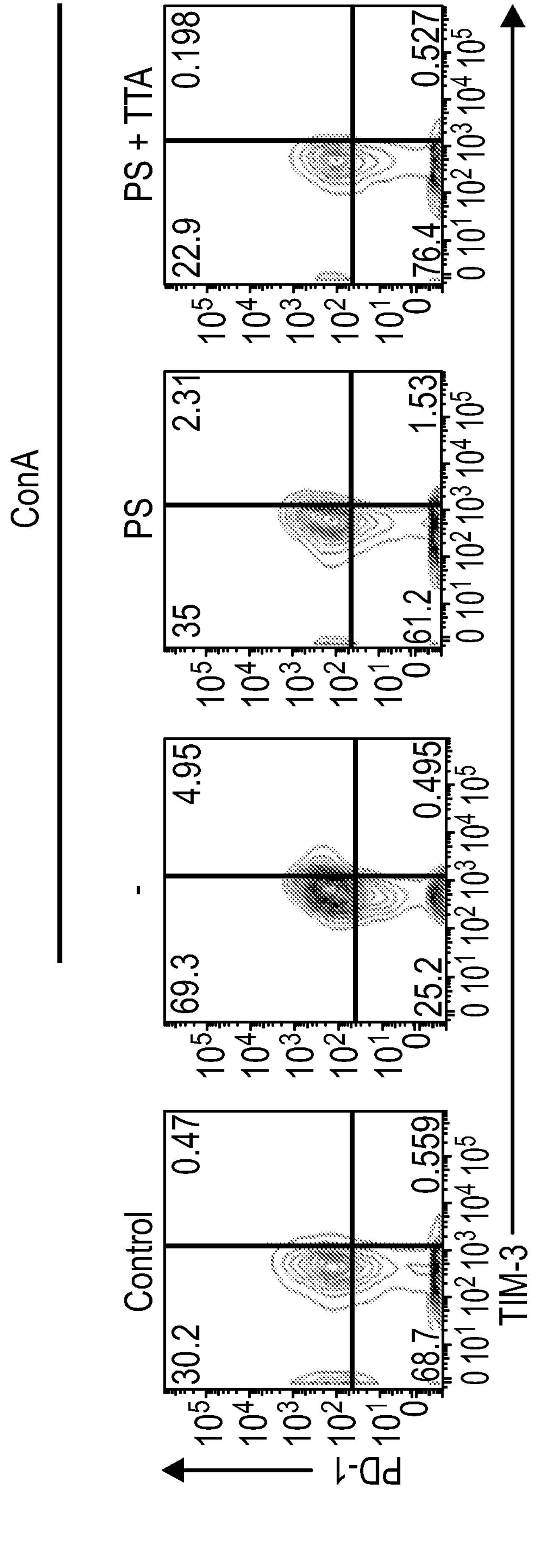
FIG. 2C shows PD-1 and TIM3 expression in PS-treated CD8 T-cells in the presence or absence of TTA.

FIG. 2C shows that when compared to the negative control, PD-1, but not TIM3, expression increased in the presence of the super T-cell activator ConA (upper left quadrant of Control and ConA panels, and lower right quadrant of Control and ConA panels). However, PD-1 and TIM3 co-expression did increase in ConA-treated CD8+ T-cells compared to control CD8+ T-cells (upper right quadrant). Compared to control-treated cells, treatment with 0.1 mM PS increased the frequency of cells expressing PD-1 and TIM3 individually (upper left and lower right quadrants of PS panel), as well as the frequency of cells co-expressing PD-1 and TIM3 (upper right quadrant of PS panel). PD-1 and TIM3 expression levels in PS-treated cells were lower than PD-1 and TIM3 expression levels in ConA-treated cells. This is explained by the low persistence and accumulation of CD8+ T-cells. Treatment with 70 mM L-(+)-tartaric acid reduced the expression of PD-1 by about 35% when compared to PS only-treated group (from 35% to 23%).

Similarly, TIM3 expression was decreased by about 66% when compared to PS only group (from 1.53% to 0.527%), and the frequency of cells co-expressing PD-1 and TIM3 was reduced by 91.4% (from 2.31% to 0.198%).

Overall, the data show that 70 mM L-(+)-tartaric acid has the capacity to reduce the negative effect of antitumor activity of PS on CD8+ T-cells, suggesting that L-(+)-tartaric acid acts as an antagonist/partial-antagonist for TIM4/TIM3. TTA reduced the expression of exhaustion markers (PD-1 and TIM3) on CD8+ T-cells. It is possible that L-(+)-tartaric acid's effects could expand beyond T-cells, such that L-(+)-tartaric acid could counteract the effects of PS on antigen-presenting cells in the tumor microenvironment allowing for increased infiltration of effective antitumor immune cells into the tumor site.

The data also suggest that TIM3 on T-cells and TIM4 on macrophages may be interesting targets for negative checkpoint inhibitors, such as TTA and analogs thereof. Targeting TIM receptors is expected to be a useful therapeutic approach for augmenting antitumor immunity and enhancing the effects of chemotherapy and/or other checkpoint inhibitors.

Example 3. Design of L-(+)-Tartaric Acid Analogs

Analogs of TTA were designed and investigated to identify mimics of PS, an endogenous ligand of the TIM4 receptor that induces an agonistic effect.

A co-crystal structure of dicaproyl PS bound to TIM4 has been published in 2007, as has been an "apo" structure of TIM4 in the presence of a high concentration of tartaric acid as precipitant. Santiago C., et al., Immunity 2007; 27(6): 941-951. The co-crystal structure of dicaproyl PS bound to TIM4 defines the "active" 3D conformation of the metal-ion-dependent ligand-binding site (MILIBS) and key interactions between the ligand and the site. The "apo" structure of TIM4 in the presence of a high concentration of tartaric acid as precipitant reveals that tartrate binds the MILIBS, and induces a roughly similar binding site conformation to PS, suggesting that tartrate could be a good mimic for the head group of PS. The tartrate structure further reveals that one of the carboxyl groups and both of the hydroxyl groups of tartrate make hydrogen bonding interactions with the MILIBS, and that the remaining carboxyl group is close to where the terminal lipid group of dicaproyl PS is bound to the OLPS head group. Taken together, this information suggested that lipid derivatives of tartrate should be simple monoesters of the non-binding carboxyl group that leaves the key hydrogen bonding functionality free for binding.

Table 2 shows selected TTA analogs.

TABLE 2

| Identifier | Compound Structure | Binding Affinity (kcal/mol) Docking to TIM4 of PDB ID: 3BIA | Docking to TIM4 of PDB ID: 3BIB | Flexible Docking to TIM4 |
|---|---|---|---|---|
| PS | | -5.4 | -6 | -5.9 |
| Tartaric Acid | 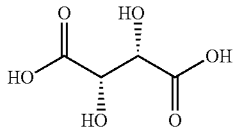 | -5.1 | -5 | -5 |
| A | 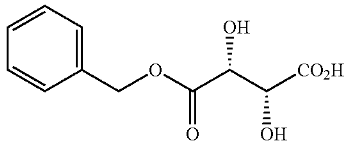 [SMILES: O=C(O)[C@H](O)[C@@H](O)C(=O)OCc1ccccc1] | -6.2 | -6.6 | -7.3 |
| B | 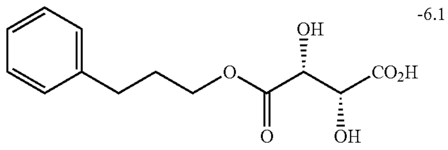 | -6.1 | -6.2 | -7.3 |
| C | 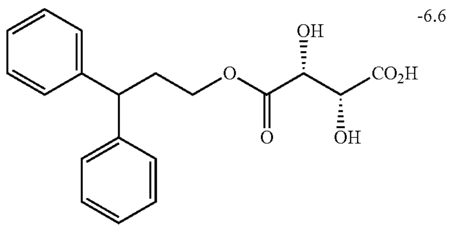 | -6.6 | -6.7 | -7.7 |

TABLE 2-continued

| Identifier | Compound Structure | Binding Affinity (kcal/mol) Docking to TIM4 of PDB ID: 3BIA | Docking to TIM4 of PDB ID: 3BIB | Flexible Docking to TIM4 |
|---|---|---|---|---|
| D | 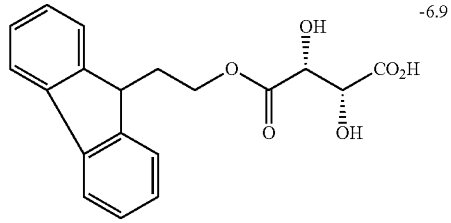 | -6.9 | -7.7 | -9.6 |

A modeling method was used to evaluate the TTA analogs in Table 2. First, the two co-crystal structures of TIM4 discussed above (PDB TD 3BIA and 3BIB) were overlaid. The root-mean-square distance (RMSD) for overlaying the two protein structures discussed above (PDB ID 3BIA and 3BIB) was 0.182 Å (or 0.134 Å using Cα only). About 50% of the polar contacts (hydrogen bonds) between the ligands and the receptor were overlapping in the two structures.

In order to validate the modeling method, ligands PS and tartrate were removed from the overlaid crystal structure and docked using docking software to validate the modeling method. For PS, the pose that was closest to the correct pose has an RMSD of 2.213 Å, and was identified among the top 11 poses. For tartrate, the pose that was closest to the correct pose had an RMSD of 1.234 Å, and was identified among the top six poses. The binding affinity of PS to its protein (PDB ID 3BIB) was 0.9 kcal/mol higher than the binding of tartrate to its protein (PDB ID 3BIA).

The TTA analogs in Table 2 were docked into each of the two protein structures of PDB TD: 3BIA and PDB TD: 3BIB. The same analogs were also docked using flexible docking to explore all possible binding modes. The binding affinity of the best pose for each of the TTA analogs was used to identify the compounds with the tightest expected binding. Compound D showed the highest binding affinity of the TTA analogs in Table 2 in the modelling method.

Example 4. Methods of Synthesis

Synthesis of the common precursor (3R,4R)-2,5-dioxotetrahydrofuran-3,4-diylbis(2,2,2-trifluoroacetate): L-(+)-tartaric acid (10 g, 67 mmol) and 2,2,2-trifluoroacetic anhydride (70 g, 330 mmol) were placed in a sealed tube and heated to 75° C., and stirred overnight. The reaction was cooled to room temperature and concentrated on a rotary evaporator. The title compound was isolated as a white solid (21 g, 97%), and was used in the next reaction without purification. $^1$H NMR (400 MHz, Chloroform-d) δ 6.16 (s, 2H).

Synthesis of (2R,3R)-4-(benzyloxy)-2,3-dihydroxy-4-oxobutanoic acid (compound A): To a solution of (3R,4R)-2,5-dioxotetrahydrofuran-3,4-diylbis(2,2,2-trifluoroacetate) (5.0 g, 15 mmol) in tetrahydrofuran (10 mL) was added benzyl alcohol (5.0 g, 4.8 mL, 46 mmol). The reaction was stirred at room temperature for 4 hours, then concentrated to remove tetrahydrofuran. 2 mL of water was added, and the reaction was stirred overnight. The reaction was concentrated, and the crude residue was purified by column chromatography eluting with 0-30% methanol in dichloromethane. The solid was triturated with ether then filtered and dried to give the title compound as a white solid (1.3 g, 38%). HRMS (ESI) m/z: Calcd for [M-H]239.0556; Found: 239.0551. $^1$H NMR (400 MHz, d2o) δ 7.40-6.91 (m, 5H), 4.97 (s, 2H), 4.49 (d, J=2.3 Hz, 1H), 4.42 (d, J=2.3 Hz, 1H).

Synthesis of (2R,3R)-2,3-dihydroxy-4-oxo-4-(3-phenylpropoxy)butanoic acid (compound B): To a solution of (3R,4R)-2,5-dioxotetrahydrofuran-3,4-diylbis(2,2,2-trifluoroacetate) (7.0 g, 22 mmol) in tetrahydrofuran (15 mL) was added 3-phenylpropan-1-ol (8.8 g, 8.8 mL, 65 mmol). The reaction was stirred at room temperature for 5 hours. The reaction was concentrated, 4 mL of water was added and the reaction was stirred overnight. The reaction was concentrated, and the crude residue was purified by column chromatography eluting first with 20-30% ethyl acetate in hexanes then with 10-30% methanol in dichloromethane to give the title compound as a clear colorless oil (1.7 g, 29%). $^1$H NMR (400 MHz, cdcl3) δ 7.32-7.22 (m, 2H), 7.22-7.13 (m, 3H), 5.78 (brs, 1H), 4.65 (d, J=1.9 Hz, 1H), 4.63 (d, J=1.9 Hz, 1H), 4.33-4.17 (m, 2H), 2.68 (t, 2H), 2.00 (dt, J=8.5, 6.6 Hz, 2H).

Sodium (2R,3R)-2,3-dihydroxy-4-oxo-4-(3-phenylpropoxy)butanoate: To a solution of the crude oil of compound B in ether was added 1N sodium hydroxide solution (6.3 mL, 6.3 mmol), and the reaction was concentrated. The solid was triturated with ether, filtered, and dried on vacuum pump to give the title compound as a sodium salt. (1.36 g, 74%) HRMS (ESI) m/z: Calcd for [M-H]267.0869; Found: 267.0868. 1H NMR (400 MHz, dmso) δ 7.37-7.01 (m, 5H), 5.45 (brs, 1H), 4.29 (d, J=2.9 Hz, 1H), 4.12-3.91 (m, 2H), 3.81 (d, J=2.9 Hz, 1H), 2.62 (dd, J=8.7, 6.7 Hz, 2H), 1.96-1.75 (m, 2H).

Synthesis of (2R,3R)-4-(3,3-diphenylpropoxy)-2,3-dihydroxy-4-oxobutanoic acid (compound C): To a solution of (3R,4R)-2,5-dioxotetrahydrofuran-3,4-diylbis(2,2,2-trifluoroacetate) (2.5 g, 7.9 mmol) in tetrahydrofuran (10 mL) was added 3,3-diphenylpropan-1-ol (5.0 g, 4.6 mL, 24 mmol). The reaction was stirred at room temperature for 6 hours. The reaction was concentrated, 4 mL of water was added and the reaction was stirred overnight. The reaction was concentrated, and the crude residue was partitioned between dichloromethane and water. The organic layer was concentrated and the crude residue was purified by column chromatography eluting first with 20-30% ethyl acetate in hexanes then with 5-30% methanol in dichloromethane to give the title compound as clear colorless oil. (877 mg, 32%) 1H NMR (400 MHz, dmso) δ 7.38-7.20 (m, 8H), 7.20-7.09

(m, 2H), 4.40 (d, J=2.5 Hz, 1H), 4.35 (d, J=2.5 Hz, 1H), 4.11 (t, J=7.9 Hz, 1H), 3.94 (ddt, J=12.9, 10.9, 5.4 Hz, 2H), 2.35 (q, J=6.9 Hz, 2H).

Sodium (2R,3R)-4-(3,3-diphenylpropoxy)-2,3-dihydroxy-4-oxobutanoate: To a solution of 770 mg of the crude oil in ether was added 1N sodium hydroxide solution (2.2 mL, 2.2 mmol), and the reaction was concentrated to give the title compound as the sodium salt. (771 mg, 94%) HRMS (ESI) m/z: Calcd for [M-H]343.1182; Found: 343.1175. $^1$H NMR (499 MHz, acetic_acid) δ 7.38-7.22 (m, 8H), 7.22-7.11 (m, 2H), 4.70 (s, 2H), 4.33-4.00 (m, 3H), 2.47 (m, 2H).

Synthesis of (2R,3R)-4-((3,3-diphenylpropyl)amino)-2,3-dihydroxy-4-oxobutanoic acid (compound E): To a solution of (3R,4R)-2,5-dioxotetrahydrofuran-3,4-diyl bis(2,2,2-trifluoroacetate) (4.3 g, 13 mmol) in tetrahydrofuran (20 mL) was added 3,3-diphenylpropan-1-amine (8.4 g, 40 mmol). The reaction was stirred at room temperature for 3 hours. The reaction was concentrated, diluted with dichloromethane and washed with 10% citric acid and brine. The organic layer was concentrated and the crude residue was purified by column chromatography with 10-45% methanol in dichloromethane to give the title compound as clear colorless oil. (930 mg, 20%)$^1$H NMR (400 MHz, $CD_3OD$) δ 7.32-7.21 (m, 8H), 7.21-7.10 (m, 2H), 4.54 (d, J=1.9 Hz, 1H), 4.41 (d, J=1.9 Hz, 1H), 4.04 (t, J=7.5 Hz, 1H), 3.27-3.04 (m, 2H), 2.30 (q, J=7.5 Hz, 2H). HRMS (ESI) m/z: Calcd for [M-H] 342.1341; Found: 342.1438.

Synthesis of (2R,3R)-4-((2-(9H-carbazol-9-yl)ethyl)amino)-2,3-dihydroxy-4-oxobutanoic acid (compound F): To a solution of (3R,4R)-2,5-dioxotetrahydrofuran-3,4-diyl bis(2,2,2-trifluoroacetate) (1.55 g, 4.79 mmol) in THE (25 mL) was added 2-(9H-carbazol-9-yl)ethan-1-amine (3.02 g, 14.4 mmol). After stirring at room temperature for 1 hour, the reaction was concentrated to remove THF. The crude residue was purified by column chromatography eluting with 0-30% methanol in dichloromethane. White needles crashed out in some of the fractions and were filtered to give the title compound as a white solid (181 mg, 11%). $^1$H NMR (499 MHz, $CD_3OD$) δ 8.30-8.16 (m, 1H), 8.07 (d, J=7.8 Hz, 2H), 7.60 (d, J=8.2 Hz, 2H), 7.45 (t, J=7.5 Hz, 2H), 7.20 (t, J=7.5 Hz, 2H), 4.58 (d, J=2.0 Hz, 1H), 4.57-4.44 (m, 2H), 4.39 (d, J=2.0 Hz, 1H), 3.79-3.58 (m, 2H). HRMS (ESI) m/z: Calcd for [M-H]341.1139; Found: 341.1150.

Synthesis of (2R,3R)-2,3-dihydroxy-4-oxo-4-((3-phenylpropyl)amino)butanoic acid (compound G): To a solution of (3R,4R)-2,5-dioxotetrahydrofuran-3,4-diyl bis(2,2,2-trifluoroacetate) (2.64 g, 8.15 mmol) in THE (20 mL) was added 3-phenylpropan-1-amine (3.30 g, 3.47 mL, 24.4 mmol). After stirring at room temperature for 2 hours, the reaction was concentrated to remove THF. The crude mixture was dissolved in 100 mL of acetone, and 4 mL of 2N NaOH was added dropwise. The solution was concentrated until a white solid precipitated out. The solid was filtered, washed with acetone, and dried on vacuum pump. The solid was further purified by column chromatography eluting with 0-20% methanol with 1% acetic acid in dichloromethane. Precipitate in column fractions was filtered and dried to give the title compound as white solid (130 mg, 6%). $^1$H NMR (499 MHz, DMSO+1 drop $D_2O$) δ 7.24-7.14 (m, 5H), 4.13 (s, 1H), 3.81 (s, 1H), 3.07 (t, J=7.0 Hz, 2H), 2.54 (t, J=7.7 Hz, 2H), 1.68 (p, J=7.2 Hz, 2H). HRMS (ESI) m/z: Calcd for [M-H]266.1029; Found: 266.1026.

Example 5. General Protocol for Liposome Synthesis

If the active substance is not water-soluble, dissolve the active substance in chloroform (or appropriate organic solvent), and proceed with the synthesis described in Option A. The resulting solution can be stored in amber glass vials at −80° C. until use.

If the active substance is water-soluble at neutral pH, proceed with the synthesis described in Option B. If the active substance is not water-soluble at neutral pH, prepare a stock solution at the desired concentration, without adjusting the pH, and proceed with the synthesis described in Option C. If Option B or C is being used, the stock solution should be prepared the day of liposome preparation.

For liposome preparation, calculate the amount of base lipid (e.g., DMPC) and active ingredient needed as follows:

Option A: If the test material is dissolved in chloroform (or another organic solvent), calculate the volume needed to obtain the desired molar concentration of the test material. Calculate the amount of DMPC needed to make up the remaining molar ratio. (Example: if a 30:70 molar ratio of test material:DMPC is desired, then multiply the amount of test material by 70 and divide by 30 to obtain the amount of DMPC needed). Aliquot proper volumes of the test material and DMPC into a 5 or 15 ml round-bottomed flask, and add 1 to 2 ml of chloroform.

Options B and C: If the test material is water-soluble, the liposome will be made up of 100% base lipid (e.g., DMPC). The amount of DMPC will be determined based on the amount of test material that will be loaded on the fully synthesized liposome. (Example: if a 30:70 molar ratio of test material:DMPC is desired, then multiply the amount of test material by 100 and divide by 30 to obtain the amount of DMPC needed). Aliquot proper volumes of DMPC into a 5 or 15 ml round-bottomed flask, and add 1 ml to 2 ml of chloroform.

Attach the round-bottomed flask to a rotary evaporator (such as a Buchi R100 rotary evaporator with V100 and I100 vacuum pump and interface), lower the adjustable arm so that a portion of the round-bottomed flask is submerged in the water bath. Turn on the vacuum pump and hit "start" on the I-100 interface. Turn on the rotating shaft to start rotating the round-bottomed flask, and set speed to "3". Reduce the vacuum, if needed, to avoid bubbling/boiling of the chloroform. Once a uniform, dry film is formed, turn off the rotating shaft. Lift the adjustable arm, hold the flask then turn off the pump. Wait for the vacuum to release. Remove the round-bottomed flask.

For the rehydration step:

Option A: Add 1 ml of PBS.

Options B and C: Add 0.5 ml of PBS, leaving room for the volume of the stock solution containing the test material as well as possible volume needed to adjust pH.

Vortex the round-bottomed flask until the solution becomes milky/turbid. Attach the flask back to the rotary evaporator, lower the arm so that the bottom of the flask is submerged in the water bath, turn the rotating shaft on to "3". After 15 minutes, the lipid film is fully hydrated and liposomes are formed.

If Option A was used, liposomes are ready for sizing.

If Option B was used, add the appropriate amount of neutral pH solution containing test material to the round-bottomed flask, and incubate in 55° C. water bath for 15 minutes. Liposomes are now ready for sizing.

If Option C was used, add the appropriate amount of solution containing test material. Slowly adjust pH to neutral paying attention to any particulate formation. The hydrophobic region of the test material should incorporate into the liposome as the pH is adjusted to approximately 7.5. Liposomes are now ready for sizing.

To size the liposomes, assemble a manual extruder (such as an Avanti 610023). Aspirate the total volume (not to exceed 1 ml) into one of the two syringes supplied with the manual extruder. Extrude the liposomal preparation 20 times. Transfer the final extruded liposomal formulation and make up the volume if needed to obtain the final desired molar concentration of the test material.

Example 6. CD8+ T-Cell Proliferation

In this experiment, the effect of L-(+)-tartaric acid as well as compounds A through C on enhancing the proliferation of murine CD8+ T cells in the presence of PS, a known inhibitor of CD8+ T cells proliferation and antitumor cytotoxic effect, was studied.

Preparation of test materials: TTA, compound A and compound B were formulated in RPMI media under aseptic conditions. The pH was adjusted to approximately 7.5 before dosing cells. Compound C was dissolved in a small volume of DMSO before diluting in RPMI media; the total volume of DMSO did not exceed 15% of the total volume of stock solution. pH was adjusted to approximately 7.5 before dosing cells.

Tissue culture and dosing: Splenocytes of C57BL/6 mice were stained with CFSE and prepared, cultured, and dosed. Cells were seeded at $1\times10^5$ cells/well in a 96-well round-bottomed plate.

Controls: Two controls were used. A negative control dosed with 10 ng/ml IL2 was used, and a positive control dosed with 20 μg/ml ConA and 10 ng/ml IL2 was used.

Treatment: After ConA stimulation (10 μg/ml), cells were dosed with 30 mM compound A, B or C with or without 0.1 mM 30:70 PS:DMPC liposomes. All wells were dosed with 10 ng/ml of IL-2.

Flow cytometer: Flow cytometer analysis was performed to assess cell survival by viability dye; proliferation was assessed by CFSE staining.

Results

Microscopic observation: Cells were observed via a microscope at the end of the incubation period. It was observed that all treatment groups looked healthy and were selected for flow cytometry. Both controls (negative and ConA) looked healthy and were selected for flow analysis as well.

Results from controls: Gated on viable single CD8+ T-cells, CFSE staining showed increased proliferation and accumulation of CD8+ T-cells upon stimulation with 20 μg/ml ConA, as evident from the single peak centered at $10^3$. The percent of CD8+ T-cell proliferation in the ConA-stimulated group was 87.8%. In the negative control group, there was a single peak, right-shifted compared to the ConA-stimulated group that was centered between $10^4$ and $10^5$. The percent of CD8+ T-cell proliferation in the negative control was 0.778%. Treatment with 0.1 mM of PS negatively impacted the accumulation of CD8+ T-cells. The percent of CD8+ T-cell proliferation was 4.84%.

Results from treatment groups: Treatment with 30 mM of L-(+)-tartaric acid increased CD8+ T-cell proliferation to 41.74%, in absence of PS, and to 120.9% in the presence of PS. Treatment with 30 mM of compound A increased the percent of CD8+ T-cell proliferation to 64.4%, in absence of PS, and to 130.3% in the presence of PS. Treatment with 30 mM of compound B increased the percent of CD8+ T-cell proliferation to 78.3%, in absence of PS, and to 42.8% in the presence of PS. Treatment with 30 mM of compound C increased the percent of CD8+ T-cell proliferation to 84.5%, in absence of PS, and to 55.5% in the presence of PS.

Discussion: Overall, the data confirmed the observation that L-(+)-tartaric acid has capacity to reduce the negative effect of PS on the proliferation of CD8+ T-cells, and expanded the observation to compounds A-C. The efficacy of the tested compounds increased as the hydrophobicity increased. In the presence of PS, 30 mM L-(+)-tartaric acid and 30 mM of compound A had similar efficacy, both resulting in about 13% CD8+ T-cell proliferation. However, in the presence of PS, compounds B and C resulted in higher CD8+ T-cell proliferation of 42.8% and 55.5%, respectively.

Overall, these observations are also in line with the molecular modeling predictions described in Example 3. As shown in Table 2, molecular modeling showed compounds A-D scoring higher than L-(+)-tartaric acid. Tested compounds A, B and C also performed better than L-(+)-tartaric acid in absence of PS in the in vitro CD8+ T-cell proliferation assay, a trend that continued in the presence of PS. All tested compounds performed better than L-(+)-tartaric acid in reversing the effects of PS on CD8+ T-cell proliferation.

Despite a 2.3 kcal/mol difference in their ΔG, compound A's efficacy was only slightly better than that of L-(+)-tartaric acid in the presence of PS (13.3% versus 12.9% proliferation, respectively). Interestingly, while both compound A and compound B had similar flexible docking to TIM4 of 3.7 kcal/mol, compound B resulted in greater than twice as much CD8+ T-cell proliferation compared to compound A in the presence of PS (420.8% versus 13.3%, respectively). This observation suggests that beyond ΔG scores, the length of the molecule may play an important role. Compound B is two carbons longer than compound A.

Example 7. The Proliferation, Activation, and Checkpoint Modulation of Murine CD8+ T-Cells Treated with Compound B and Compound C in the Presence and Absence of Phosphatidylserine (PS)

In this study, the effects of increasing doses of compound B and compound C on proliferation (CFSE staining), activation (Granzyme B and IFN-γ), and checkpoint modulation (PD1 and TIM3) of murine CD8+ T-cells in the presence and absence of phosphatidylserine (PS) were explored.

Preparation of test materials: 30:70 PS:DMPC liposomes were synthesized in PBS. Compound B was dissolved in RPMI media to the desired concentration, and pH was adjusted as needed to pH approximately 7.5. Compound C was first dissolved in a small volume of DMSO before diluting to the final desired concentration. DMSO did not exceed 15% v/v. pH was adjusted as needed to approximately 7.5.

Tissue culture and dosing: Splenocytes of C57BL/6 mice were stained with CFSE and prepared, cultured, and dosed. Cells were seeded at $4\times10^5$ cells/well.

Controls: Two controls were used. A negative control dosed with 10 ng/ml IL-2 was used, and a positive control dosed with 20 μg/ml ConA and 10 ng/ml IL-2 was used.

Treatment: After ConA stimulation (10 μg/ml), cells were dosed with log 3 dilution of compound B or compound C to cover a range from $1\times10^{-3}$ to 30 mM in duplicates with or without 0.1 mM PS:DMPC liposomes. All wells were dosed with 10 ng/ml of IL-2.

Flow cytometer: Flow cytometer analysis was performed to assess cell proliferation by CFSE, activation by double staining for Granzyme B (GzmB) and IFN-γ, checkpoint modulation by double staining for PD-1 and TIM3.

Exposure-response analysis: Change from baseline was calculated for each marker as follows:

$$\text{Fold change} = \frac{\text{Response}_{treatment}}{\text{Response}_{control}} \quad (1)$$

Concentration versus change was fitted to an appropriate three-, four- or five-parameter log-logistic model using "dre" package in "R."

Results

Microscopic observation: Cells were observed via a microscope at the end of the incubation period. Both controls (negative and ConA) looked healthy and were selected for flow analysis as well. T cell clusters were observed throughout the incubation period. Cluster formation, a sign of proliferation, was observed in compound B- and compound C-treated groups to a greater extent than in PS only-treated cells. Furthermore, cells treated with compound C did not show any discernable differences in cluster formation under microscopic examination between compound C alone or in the presence of PS in comparison to PS alone, especially at higher doses. Generally, all cells looked healthy and suitable for flow cytometry analysis.

The Effects of Compounds B and C on the Proliferation of CD8+ T-Cells in the Presence and Absence of PS Results from controls: CFSE staining showed increased proliferation and accumulation of CD8+ T-cells in the high dose ConA positive control group (ConA) as compared to the negative control group dosed with IL-2 alone (CTL). This was evident from the single, right-shifted peak in the negative control group centered around $10^4$ versus the ConA-treated group. In the ConA-treated group, a left-shifted peak between 0 and $10^3$ was observed corresponding to proliferating cells. Treatment with 0.1 mM PS liposomes resulted in a right-shift similar to the negative control. PS treatment resulted in almost complete suppression of T-cell proliferation in response to the high dose ConA (4.24% proliferation compared to 80.6% in the ConA treatment group and 0.15% in the negative control group).

Figure 3A:
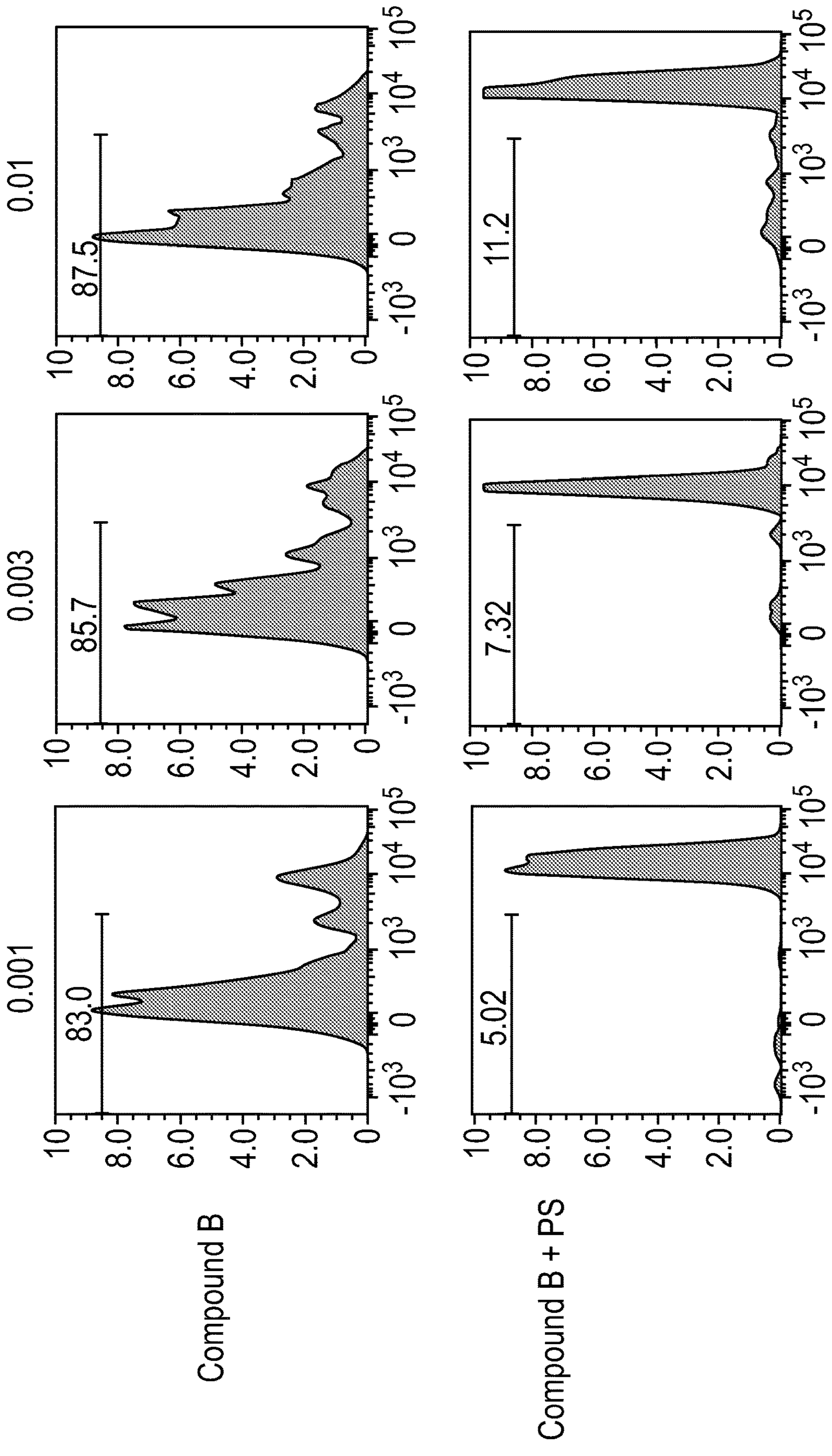
FIG. 3A shows CD8 T-cell proliferation as measured by CFSE staining in Compound B-treated cells in the presence and absence of PS.
Figure 3A:
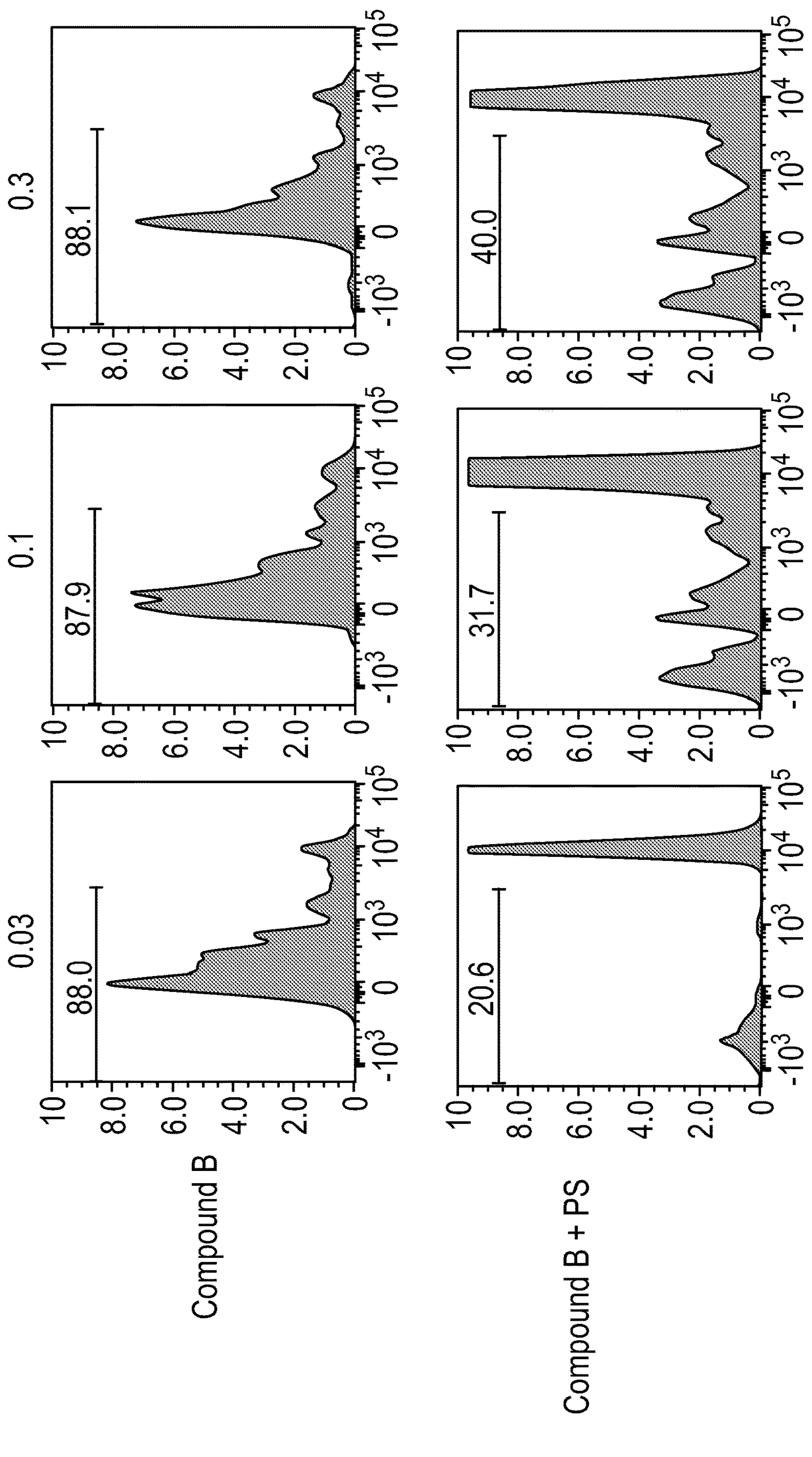
Figure 3A:
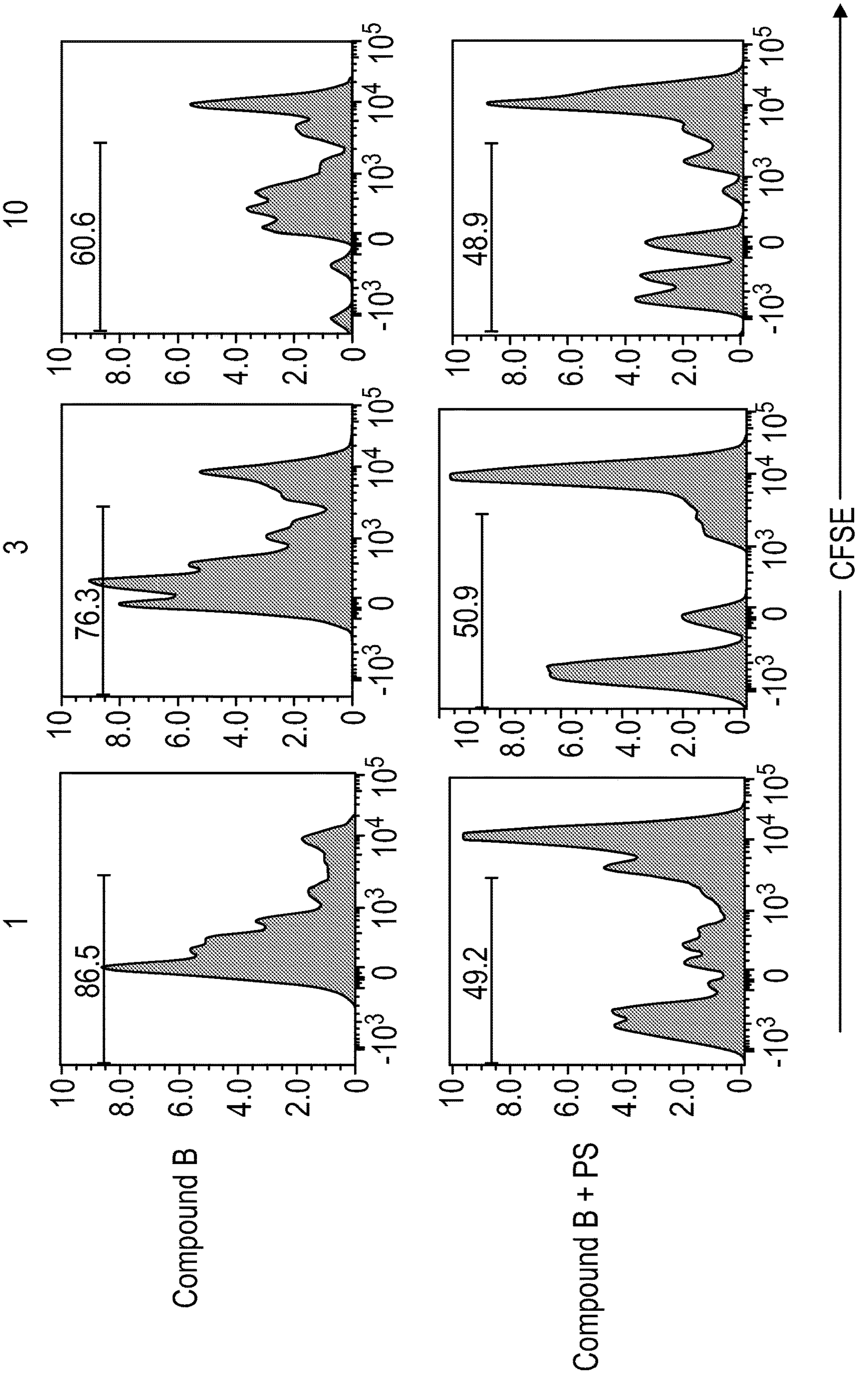

Results from treatment groups: Cells treated with low dose ConA (10 g/ml) and increasing doses of compound B in the absence of PS liposomes showed robust proliferation similar to the levels observed in the high dose ConA control. This robust proliferation was observed at all dose levels of compound B. The presence of 0.1 mM PS liposomes suppressed T-cell proliferation in cells treated with low dose ConA (10 μg/ml) and low dose compound B. The suppressive effects of PS on T-cell proliferation, however, were partially reversed as a function of increasing doses of compound B (FIG. 3A, lower panel).

The fold change from baseline of CD8+ T-cells proliferation as a function of increasing doses of compound B was calculated using equation 1, where ResponseControl was the proliferation of cells treated with IL-2 alone and Responsetreatment was the proliferation at each dose of compound B. The baseline PS response was calculated using the same equation where Responsetreatment was the proliferation of cells treated with 0.1 mM PS.

Figure 3B:
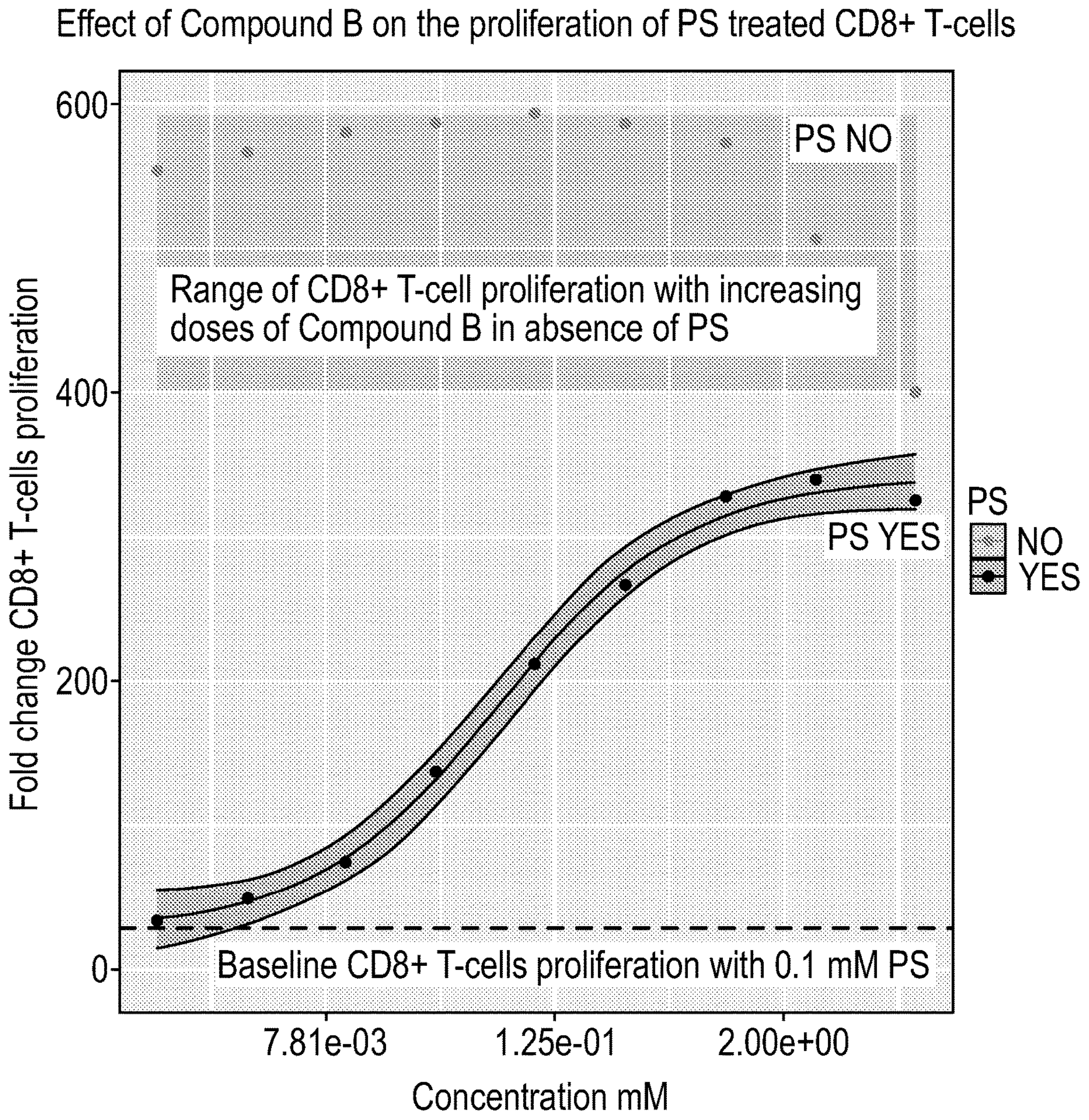
FIG. 3B shows concentration-response analysis of Compound B in the presence and absence of 0.1 mM PS.

As seen in FIG. 3B, compared to control cells, PS-treated cells had a 28-fold increase in CD8+ T-cell proliferation (dashed line in FIG. 3B). The fold increase in CD8+ T-cell proliferation in cells treated with increasing doses of compound B in the absence of PS is presented in the shaded rectangle in FIG. 3B. In the presence of 0.1 mM PS, compound B reversed the inhibitory effects of PS on CD8+ T-cell proliferation in a dose-dependent manner. The data were fitted to a four-parameter log-logistic model (curve in FIG. 3B). The 95$^{th}$ percent confidence interval about the mean fit line shows some overlap between compound B dose-response and the baseline PS effect at the lowest dose of compound B only. The model estimated $EC_{80}$ was 1.39e-01 mM.

Figure 3C:
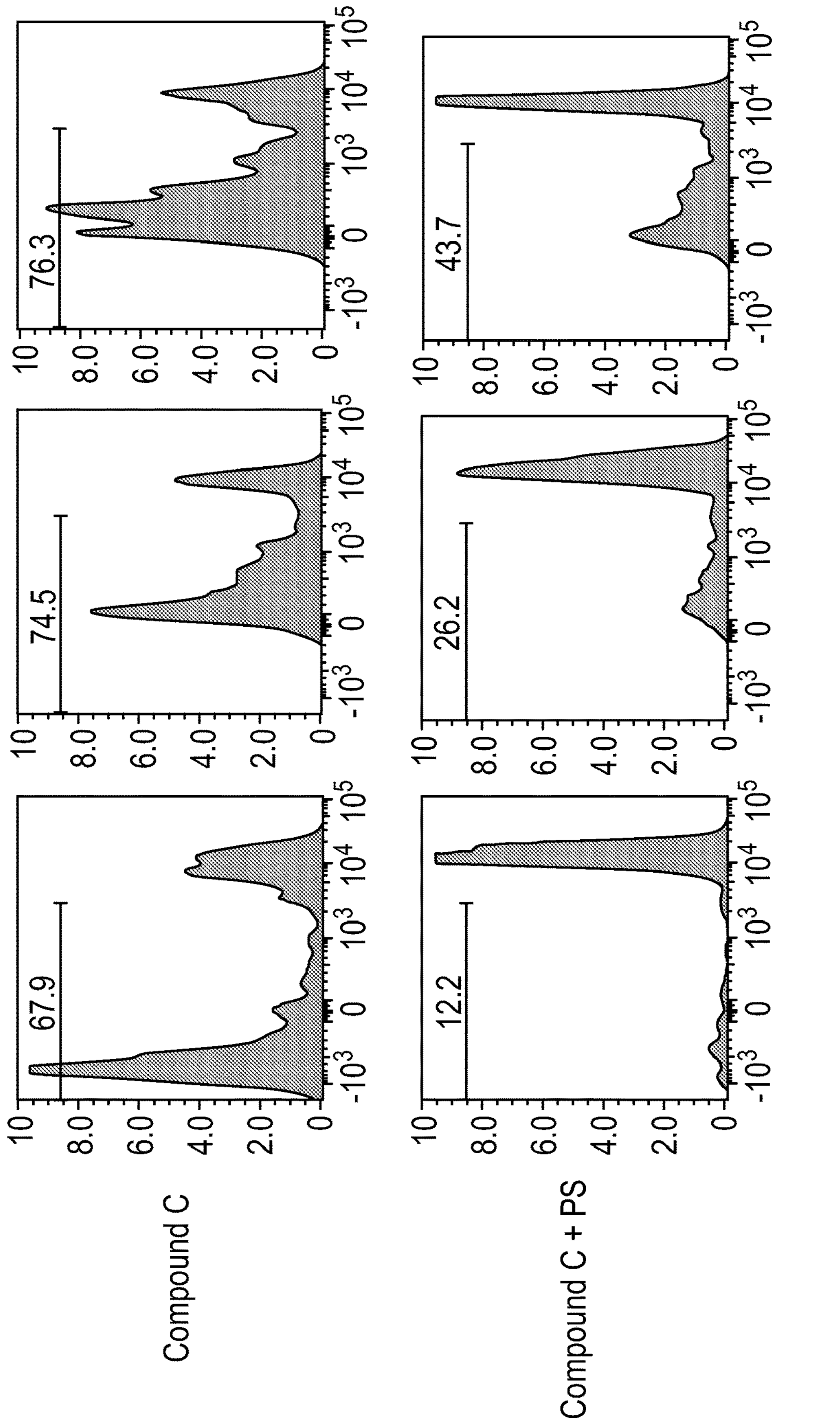
FIG. 3C shows CD8 T-cell proliferation as measured by CFSE staining in Compound C-treated cells in the presence and absence of PS.
Figure 3C:
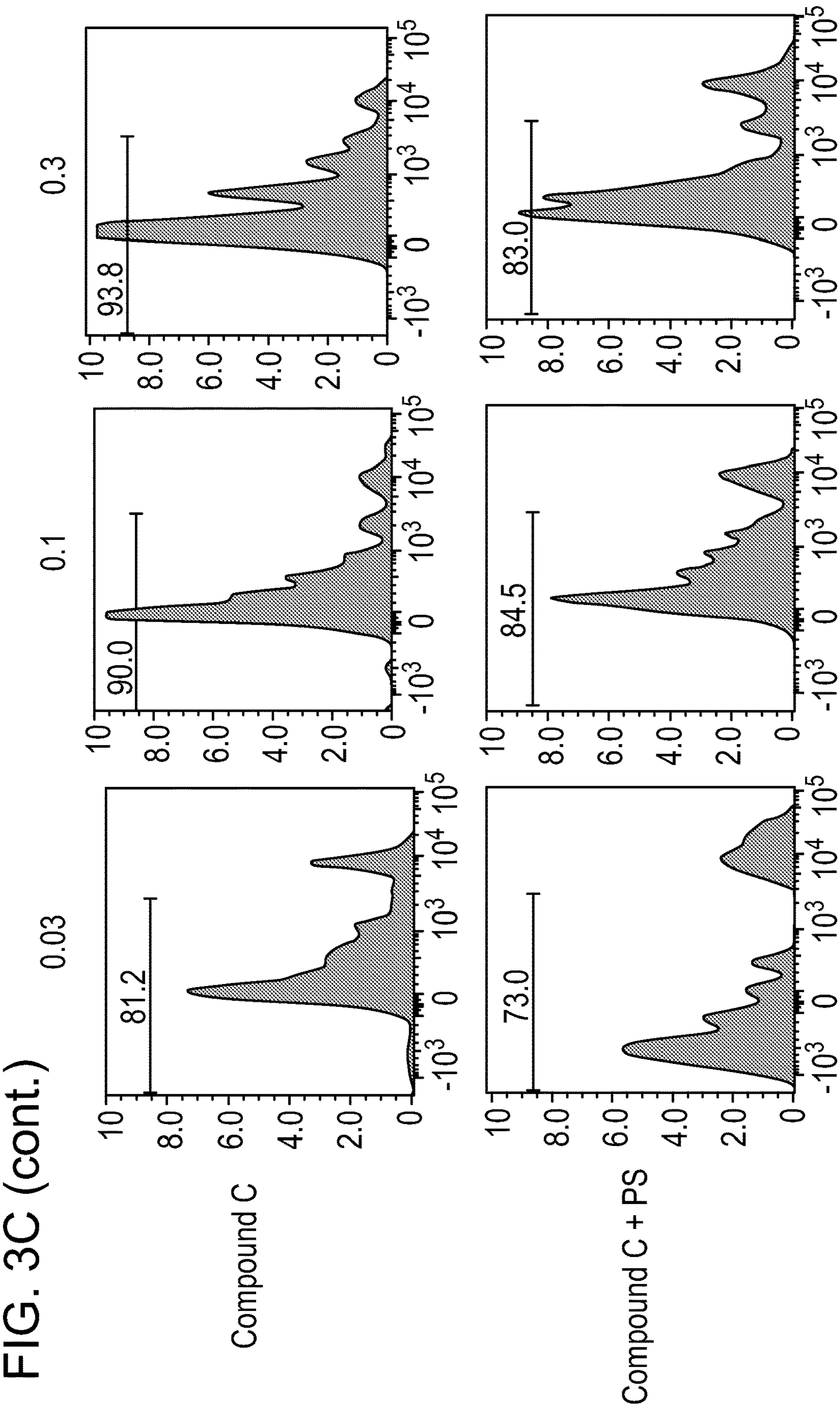
Figure 3C:
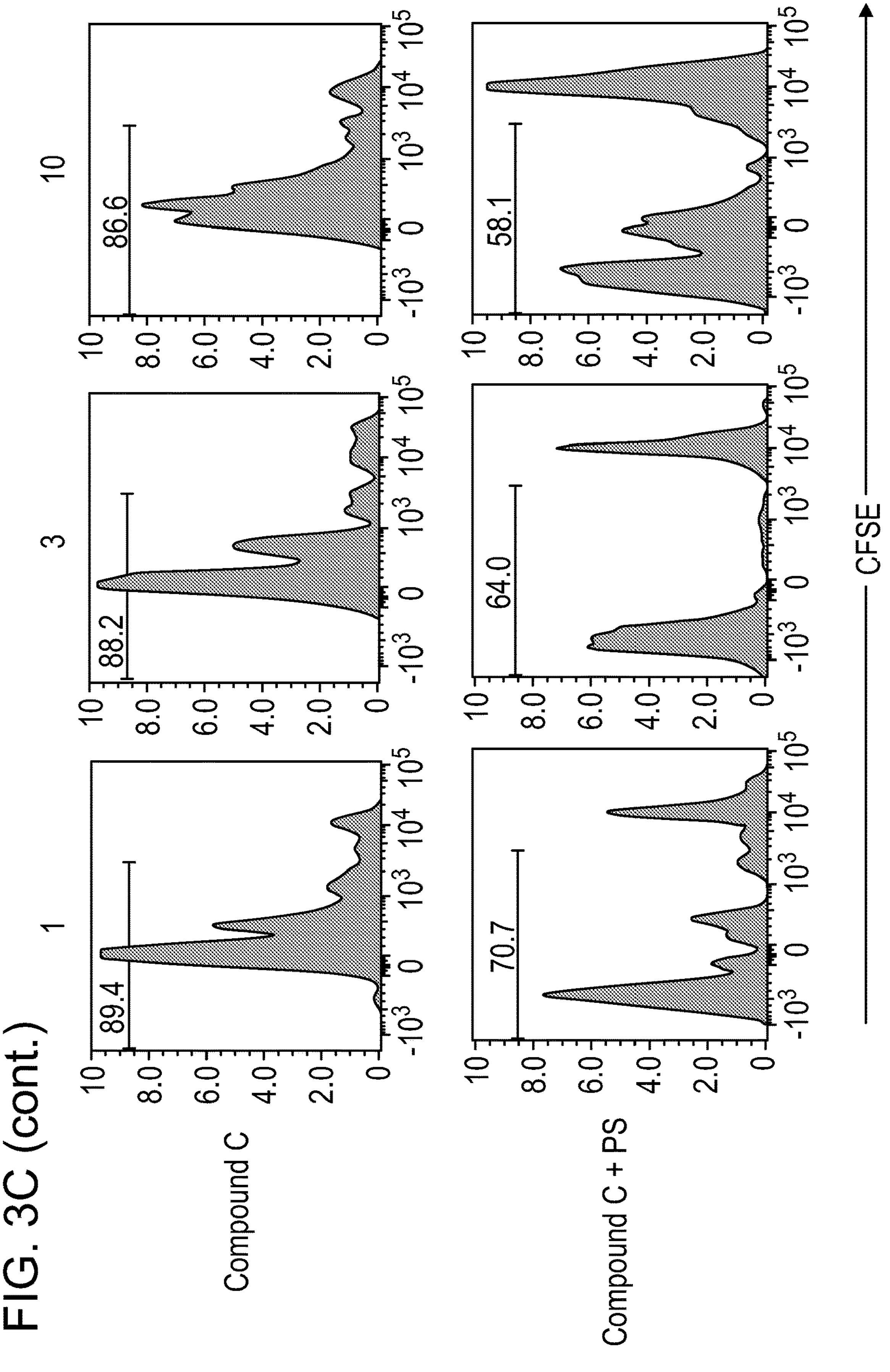

Cells treated with low dose ConA (10 μg/ml) and increasing doses of compound C in the absence of PS liposomes showed robust proliferation similar to the levels observed in the high dose ConA control (FIG. 3C, upper panel). This robust proliferation was observed at all dose levels of compound C.

The presence of 0.1 mM PS liposomes suppressed T-cell proliferation in cells treated with low dose ConA (10 μg/ml) and low dose compound C. The suppressive effects of PS on T-cell proliferation, however, were completely reversed (and T-cell proliferation at doses greater than 0.03 mM overlapped with the proliferation observed in absence of PS) as a function of increasing doses of compound C (FIG. 3C, lower panel).

Figure 3D:
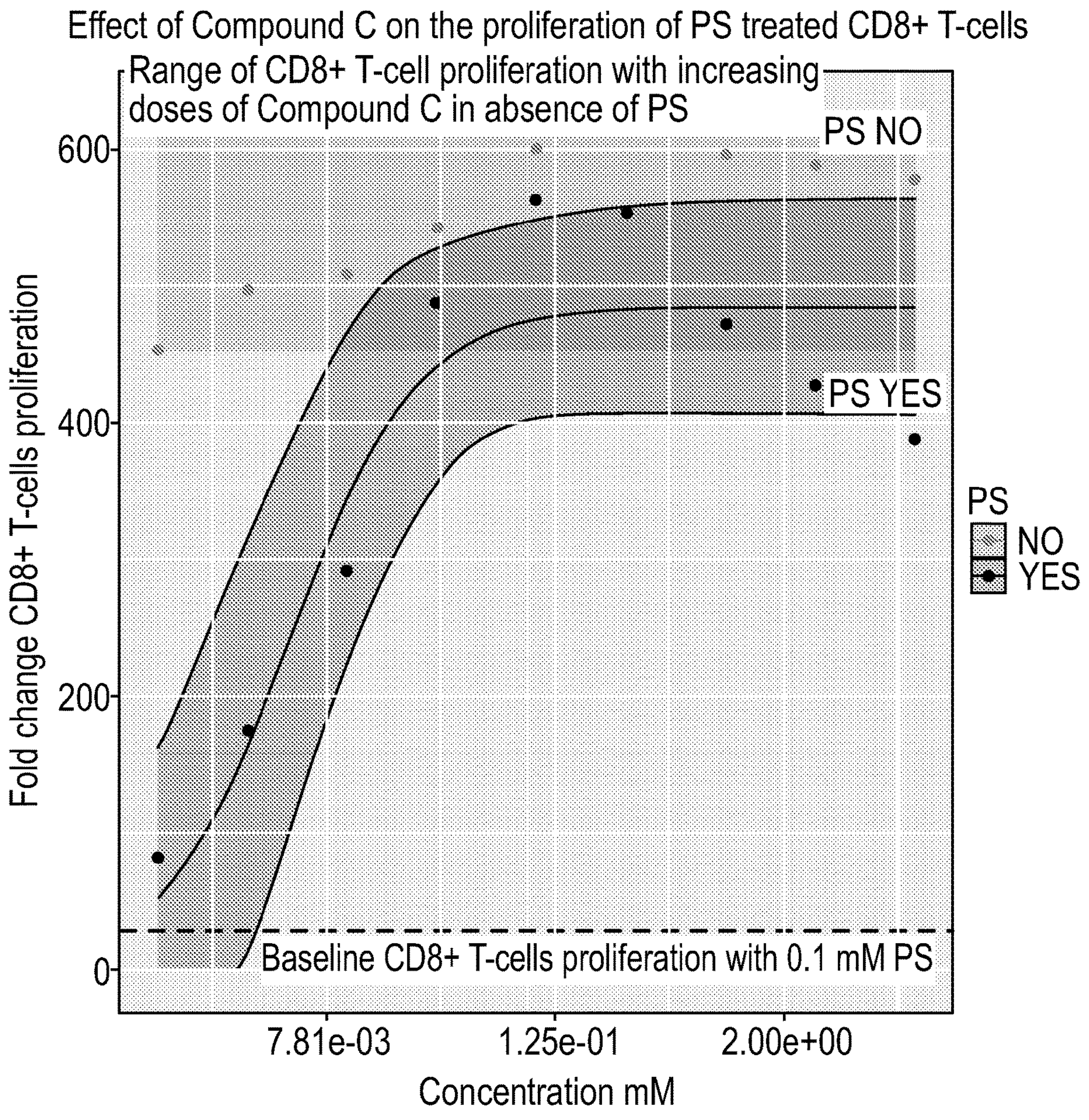
FIG. 3D shows concentration-response of Compound C in the presence and absence of 0.1 mM PS.

The fold change from baseline of CD8+ T-cell proliferation as a function of increasing doses of compound C was calculated as for compound B. As seen in FIG. 3D, compared to control cells, PS treated cells had a 28-fold increase in CD8+ T-cell proliferation (dashed line in FIG. 3D). The fold increase in CD8+ T-cell proliferation in cells treated with increasing doses of compound C in the absence of PS is presented in the shaded rectangle in FIG. 3D. In the presence of 0.1 mM PS, compound C reversed the inhibitory effects of PS on CD8+ T-cell proliferation in a dose-dependent manner. The data were fitted to a three-parameter log-logistic model (curve in FIG. 3D). The 95$^{th}$ percent confidence interval about the mean fit line shows some overlap between compound C dose-response and the baseline PS effect at the lowest doses of compound C only. At doses greater than 0.03 mM of compound C, the confidence interval about the fit line overlapped with the shaded area in FIG. 3D representing the compound C effects in absence of PS. These data suggest that compound C could completely reverse the inhibitory effect of PS on T-cell proliferation. The model estimated an $EC_{80}$ of 1.46e-02 mM.

Figure 3E:
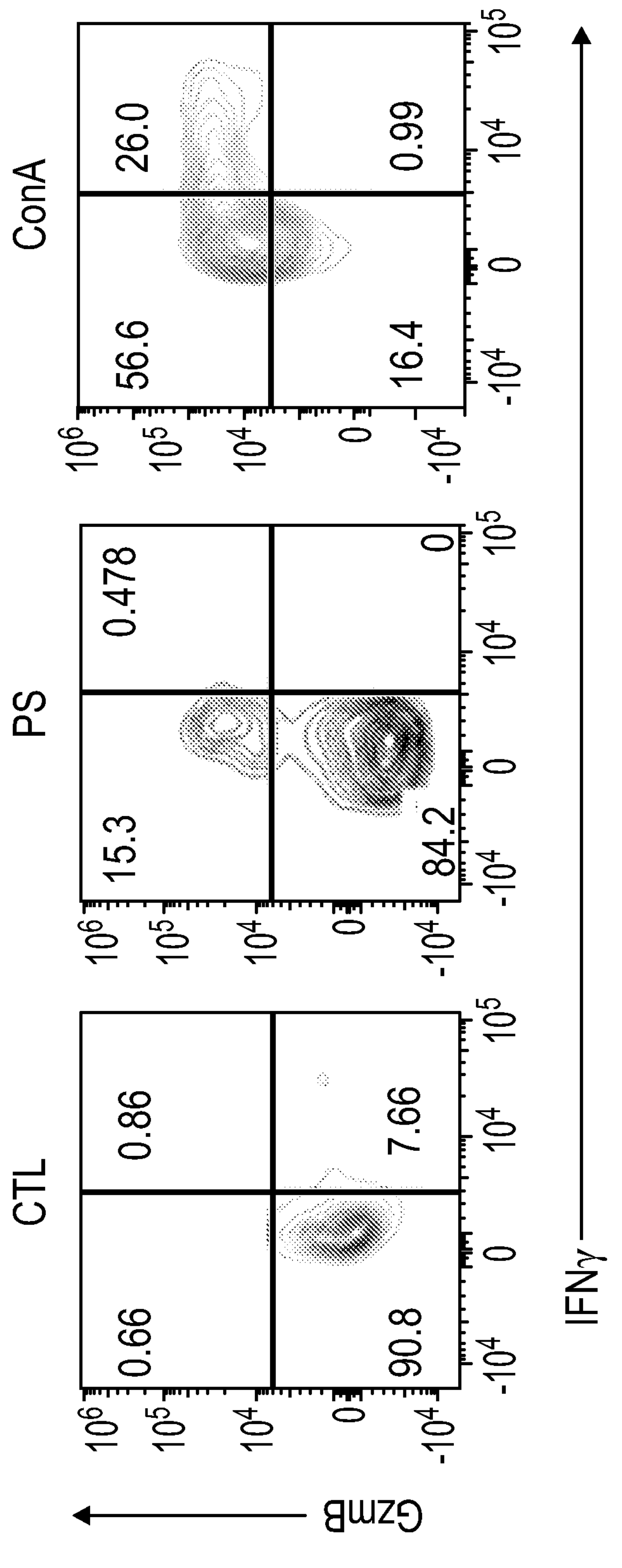
FIG. 3E shows GzmB+/IFN-γ+ double-positive in control groups.

The Effects of Compounds B and C on the GzmB+/IFN-γ+ on CD8+ T-Cells in the Presence and Absence of PS Results from controls: GzmB+/IFN-γ+ staining showed a 30-fold increased double-positive CD8+ T-cells when treated with high dose ConA (ConA) as compared to the negative control group dosed with IL-2 alone (CTL) (FIG. 3E). Treatment with 0.1 mM PS liposomes resulted in one half the double-positive CD8+ T-cells count as the negative control (FIG. 3E).

Figure 3F:
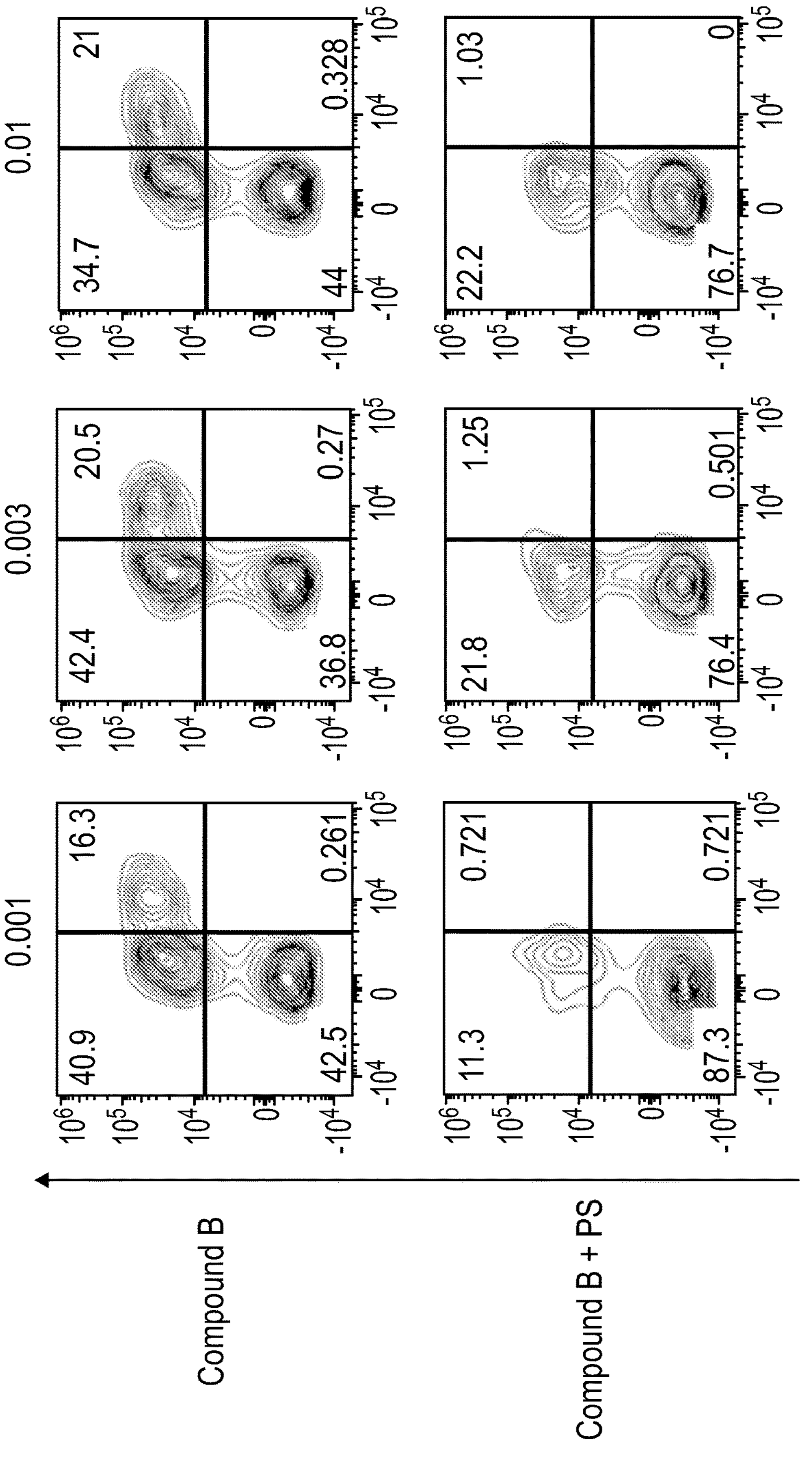
FIG. 3F shows GzmB+/IFN-γ+ in Compound B-treated cells in the presence and absence of 0.1 mM PS.
Figure 3F:
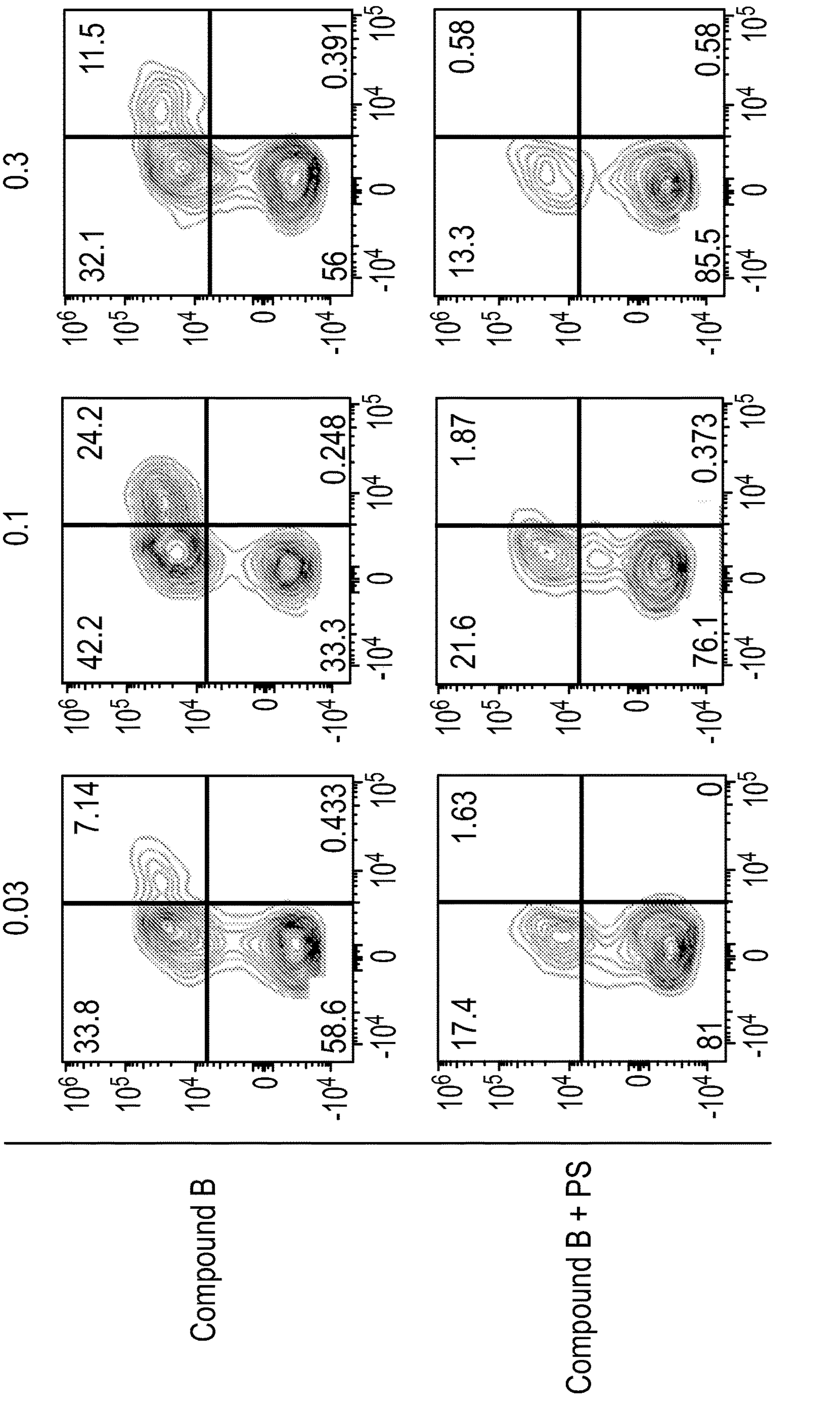
Figure 3F:
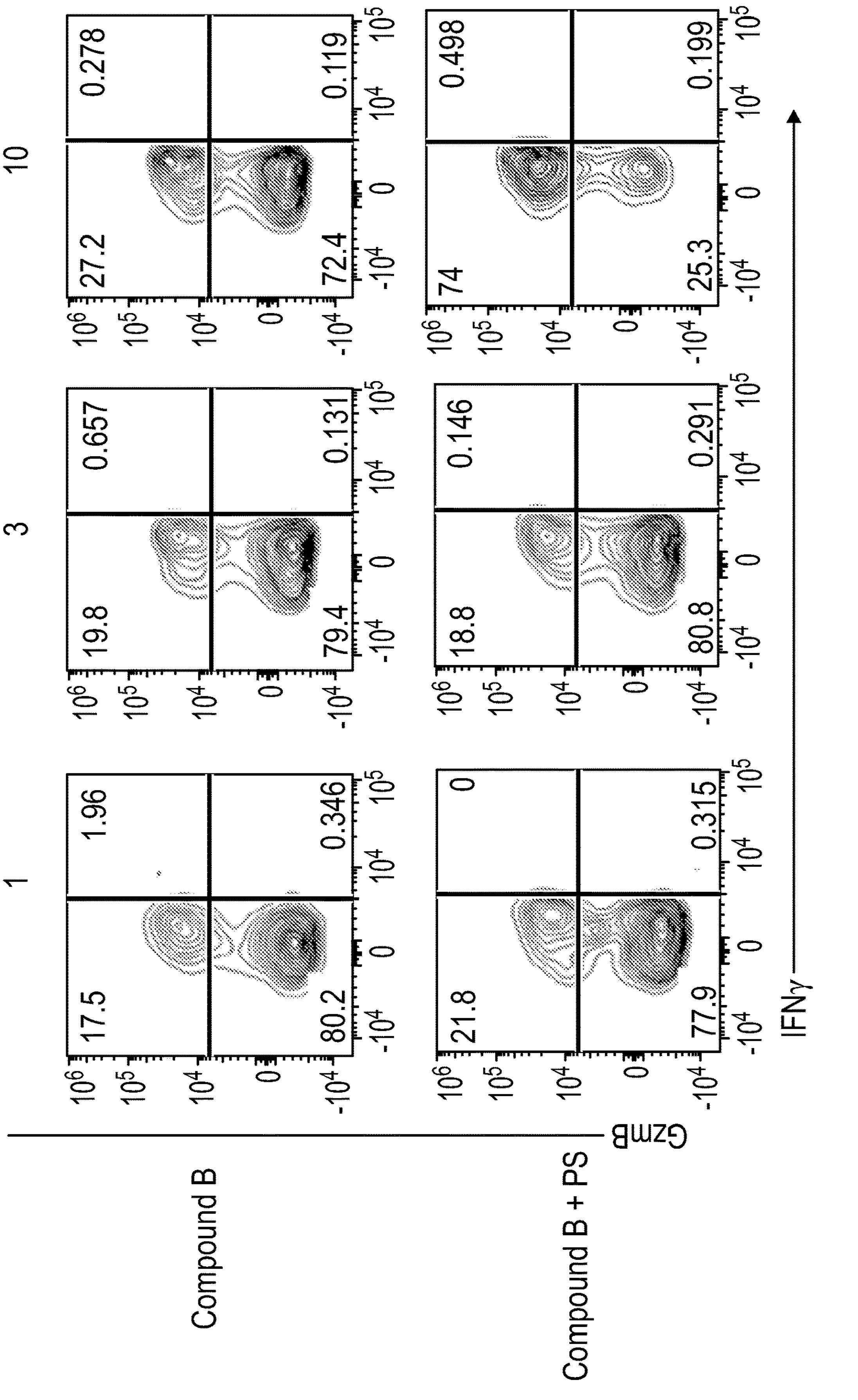

Results from treatment groups: Cells treated with low dose ConA (10 g/ml) and increasing doses of compound B in the absence of PS liposomes showed a robust increase in GzmB+/IFN-γ+ double-positive CD8+ T-cells similar to the levels observed in the high dose ConA control (FIG. 3F, upper panel). This robust proliferation was observed at all dose levels of compound C up to 0.1 mM after which GzmB+/IFN-γ+ double-positive CD8+ T-cells begins to drop. This could be a result of overstimulation of T-cells at those high doses.

The presence of 0.1 mM PS liposomes suppressed GzmB+/IFN-γ+ production in CD8+ T-cell treated with low dose ConA (10 g/ml). The inhibitory effect of PS was also observed at the low dose of compound B. The suppressive effects of PS on GzmB+/IFN-γ+ production in CD8+ T-cell, however, were partially reversed as a function of increasing doses of compound B (FIG. 3F, lower panel).

The fold change from baseline GzmB+/IFN-γ+ double-positive CD8+ T-cells as a function of increasing doses of compound B was calculated using equation 1, where Responsecontrol was GzmB+/IFN-γ+ double-positive CD8+ T-cells in cells treated with IL-2 alone and Responsetreatment was GzmB+/IFN-γ+ double-positive CD8+ T-cells at each dose of compound B. The baseline PS response was calculated using the same equation with Responsetreatment as the GzmB+/IFN-γ+ double-positive CD8+ T-cells treated with 0.1 mM PS.

Due to the observed reduction in GzmB+/IFN-γ+ at high doses of compound B, only data up to 0.1 mM was used for model fitting. Compared to control cells, PS reduced the GzmB+/IFN-γ+ double-positive CD8+ T-cells to one half the negative control (dashed line in FIG. 3G). Treatment with increasing doses of compound B in the absence of PS, resulted in a more than 16-fold increase in the GzmB+/IFN-γ+ double-positive CD8+ T-cells (top curve in FIG. 3G).

Figure 3G:
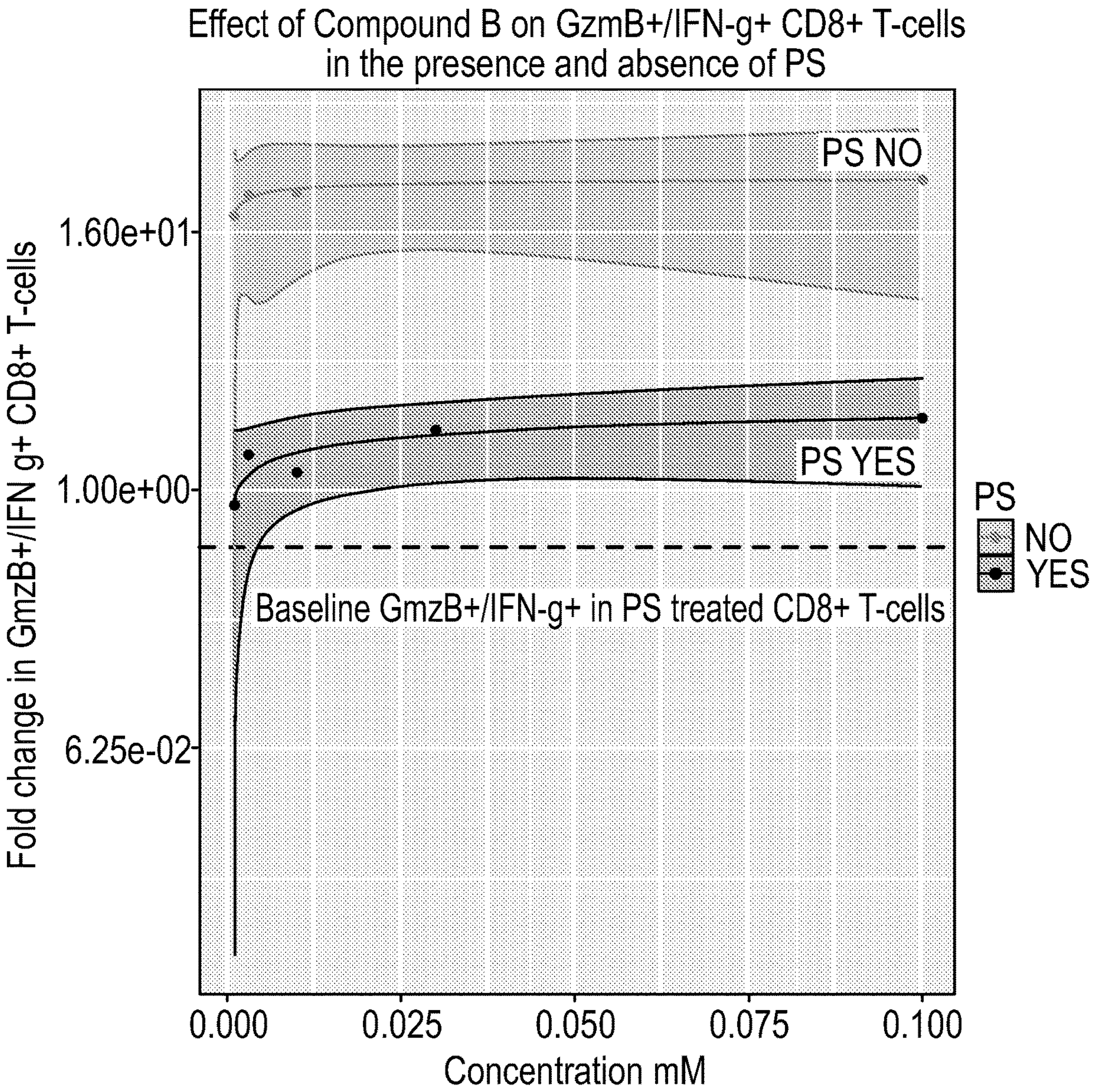
FIG. 3G shows concentration-response analysis of Compound B in the presence and absence of 0.1 mM PS (GzmB+/IFN-γ+).

In the presence of 0.1 mM PS, compound B reversed the inhibitory effects of PS on GzmB+/IFN-γ+ double-positive CD8+ T-cells in a dose-dependent manner (lower curve in FIG. 3G). The highest dose of compound B resulted in a 2-fold increase in GzmB+/IFN-γ+ double-positive CD8+ T-cells compared to the negative control, and 4.6-fold increase when compared to PS treated cell (FIG. 3G).

Figure 3H:
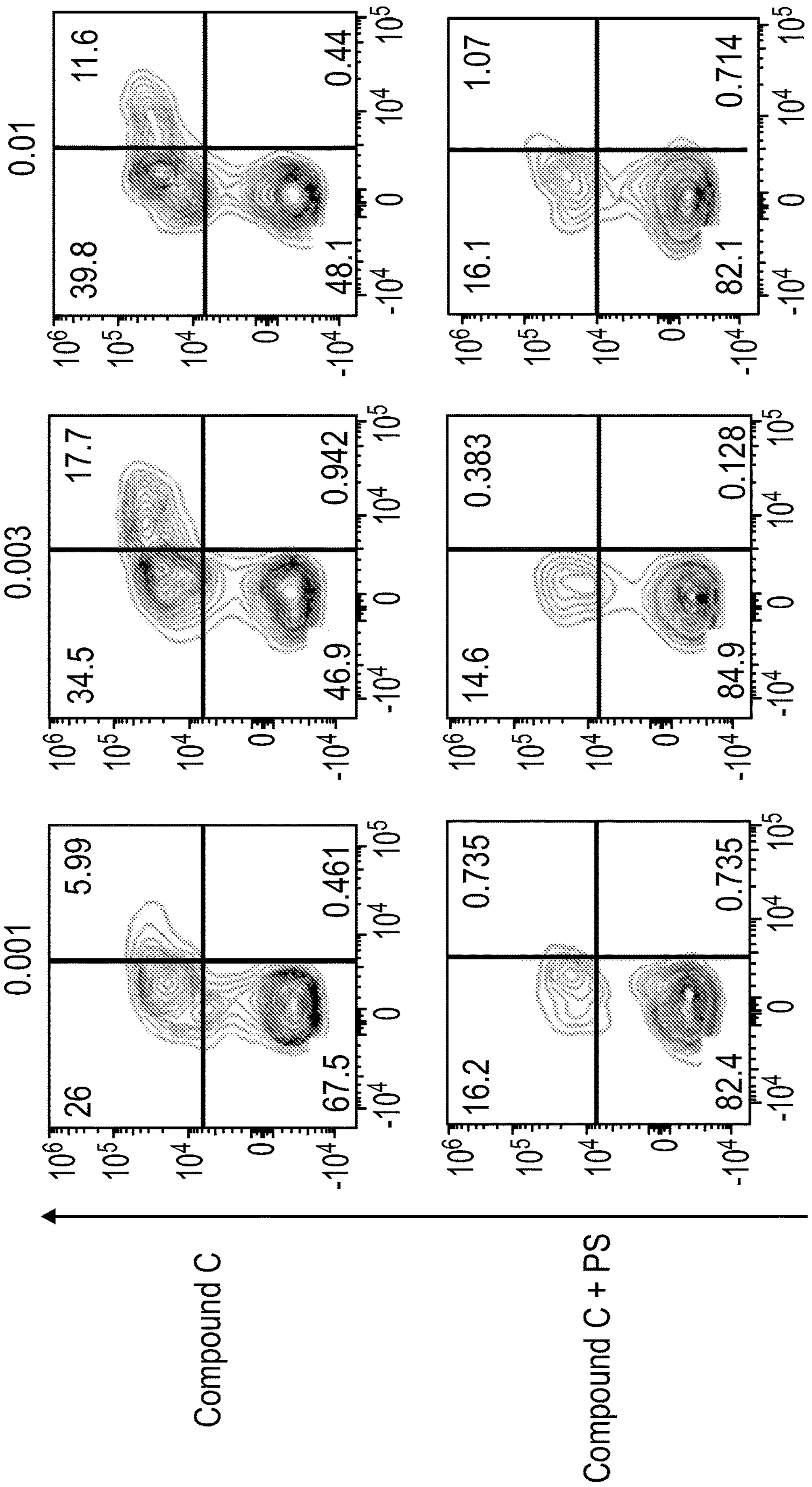
FIG. 3H shows GzmB+/IFN-γ+ in Compound C-treated cells in the presence and absence of PS.
Figure 3H:
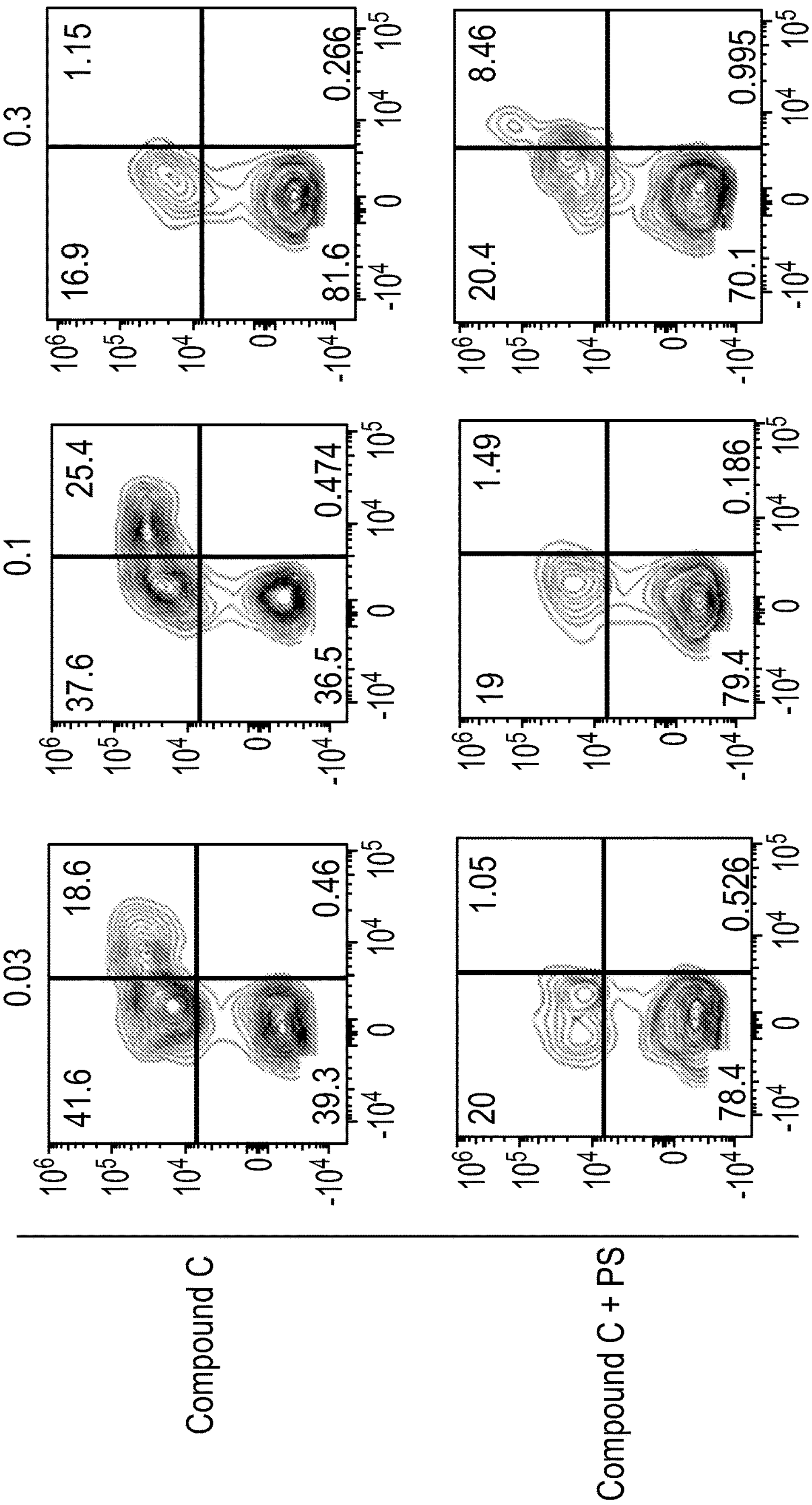
Figure 3H:
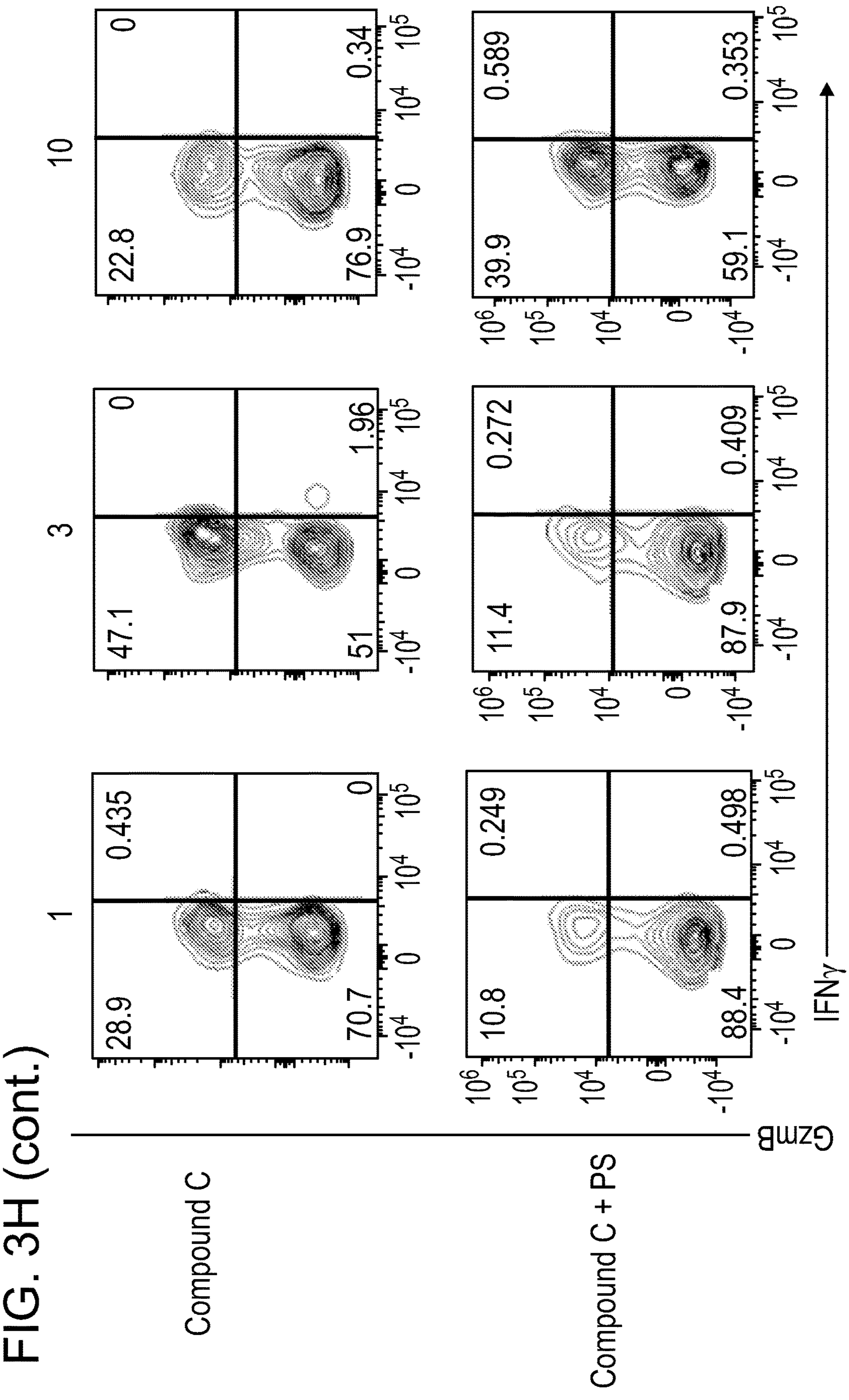

Cells treated with low dose ConA (10 g/ml) and increasing doses of compound C in the absence of PS liposomes showed a robust increase in GzmB+/IFN-γ+ double-positive CD8+ T-cells similar to the levels observed in the high dose ConA control (FIG. 3H, upper panel). This robust proliferation was observed at all dose levels of compound C up to 0.1 mM after which GzmB+/IFN-γ+ double-positive CD8+ T-cells began to drop.

The presence of 0.1 mM PS liposomes suppressed GzmB+/IFN-γ+ production in CD8+ T-cell treated with low dose ConA (10 g/ml). The inhibitory effect of PS was also observed at the low dose of compound C. The suppressive effects of PS on GzmB+/IFN-γ+ production in CD8+ T-cell, however, were partially reversed as a function of increasing doses of compound C (FIG. 3H, lower panel.

The fold change from baseline GzmB+/IFN-γ+ double-positive CD8+ T-cells as a function of increasing doses of compound C was calculated as for compound B. Due to the observed reduction in GzmB+/IFN-γ+ at high doses of compound C, only data up to 0.1 mM was used for model fitting. Compared to control cells, PS reduced the GzmB+/IFN-γ+ double-positive CD8+ T-cells to one half the negative control (dashed line in FIG. 3I). Treatment with increasing doses of compound C in the absence of PS, resulted in an about 30-fold increase in the GzmB+/IFN-γ+ double-positive CD8+ T-cells when compared to the negative control (top curve in FIG. 3I).

Figure 3I:
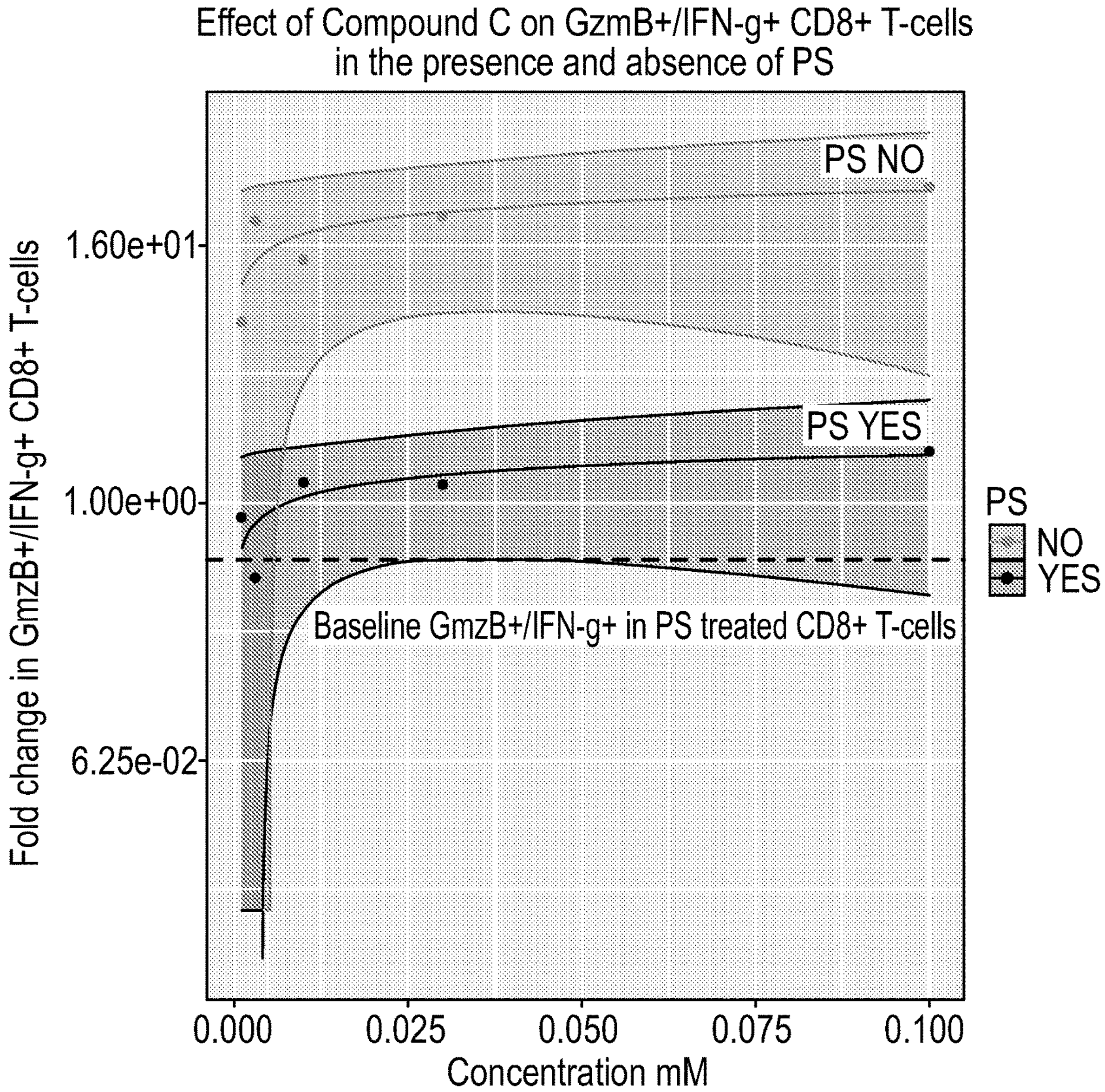
FIG. 3I shows concentration-response analysis of Compound C in the presence and absence of 0.1 mM PS (GzmB+/IFN-γ+).

In the presence of 0.1 mM PS, compound C seemed to reverse the inhibitory effects of PS on GzmB+/IFN-γ+ double-positive CD8+ T-cells in a dose-dependent manner (lower curve in FIG. 3I). Although the lower limit of the confidence interval in the Compound C dose-response curve crossed the dashed line representing the baseline GzmB+/IFN-γ+ double positive in PS only-treated cells, on average, compound C counteracted the effects of PS. The highest dose of compound C resulted in a 10-fold increase in GzmB+/IFN-γ+ double-positive CD8+ T-cells compared to the negative control, and 18-fold increase when compared to PS treated cell (FIG. 3I).

Figure 3J:
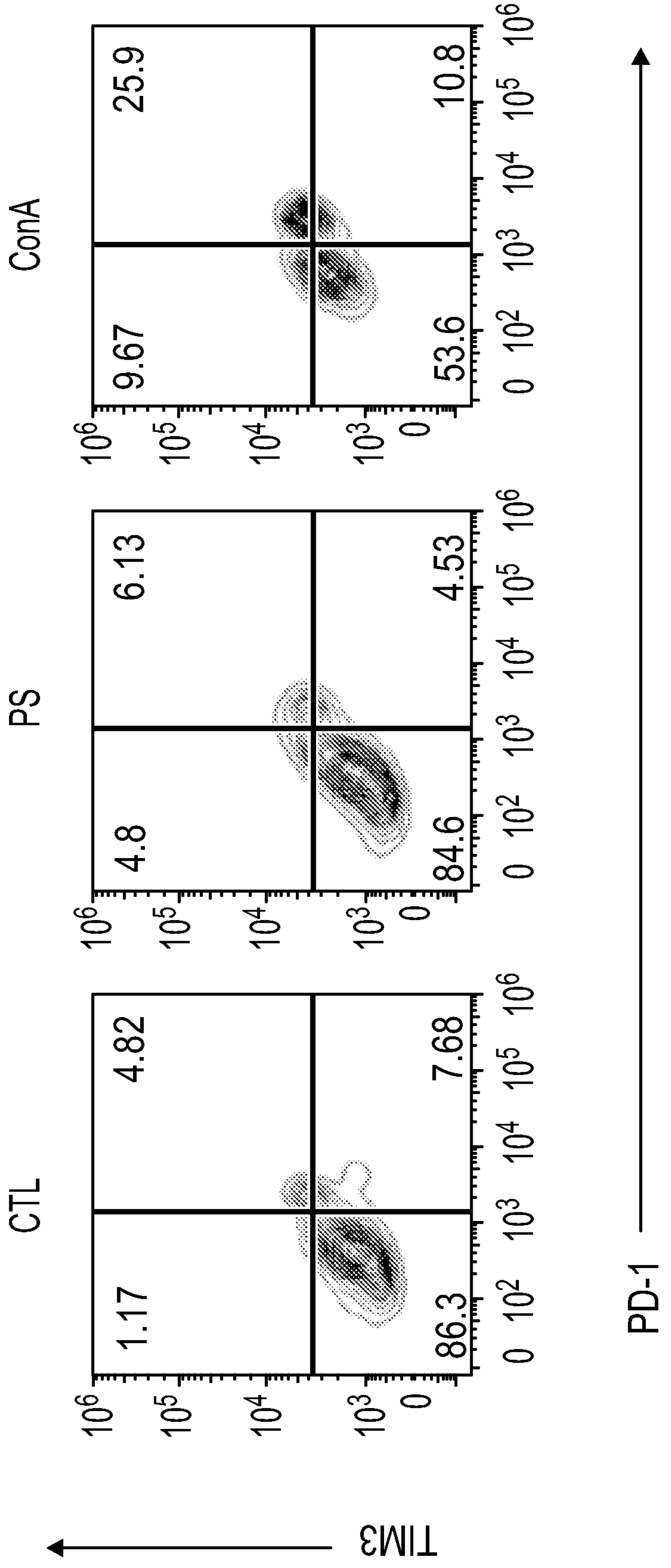
FIG. 3J shows TIM3+/PD-1+ double positive in control groups.

The Effects of Compounds B and C on the TIM3+/PD-1+ in CD8+ T-Cells in the Presence and Absence of PS Results of controls: TIM3+/PD-1+ staining of CD8+ T-cells showed a 5.4-fold increase in double-positive CD8+ T-cells when treated with high dose ConA (ConA) as compared to the negative control group dosed with IL-2 alone (CTL) (FIG. 3J). Treatment with 0.1 mM PS liposomes resulted in 1.27-fold increase in double-positive CD8+ T-cells count as the negative control (FIG. 3I).

Figure 3K:
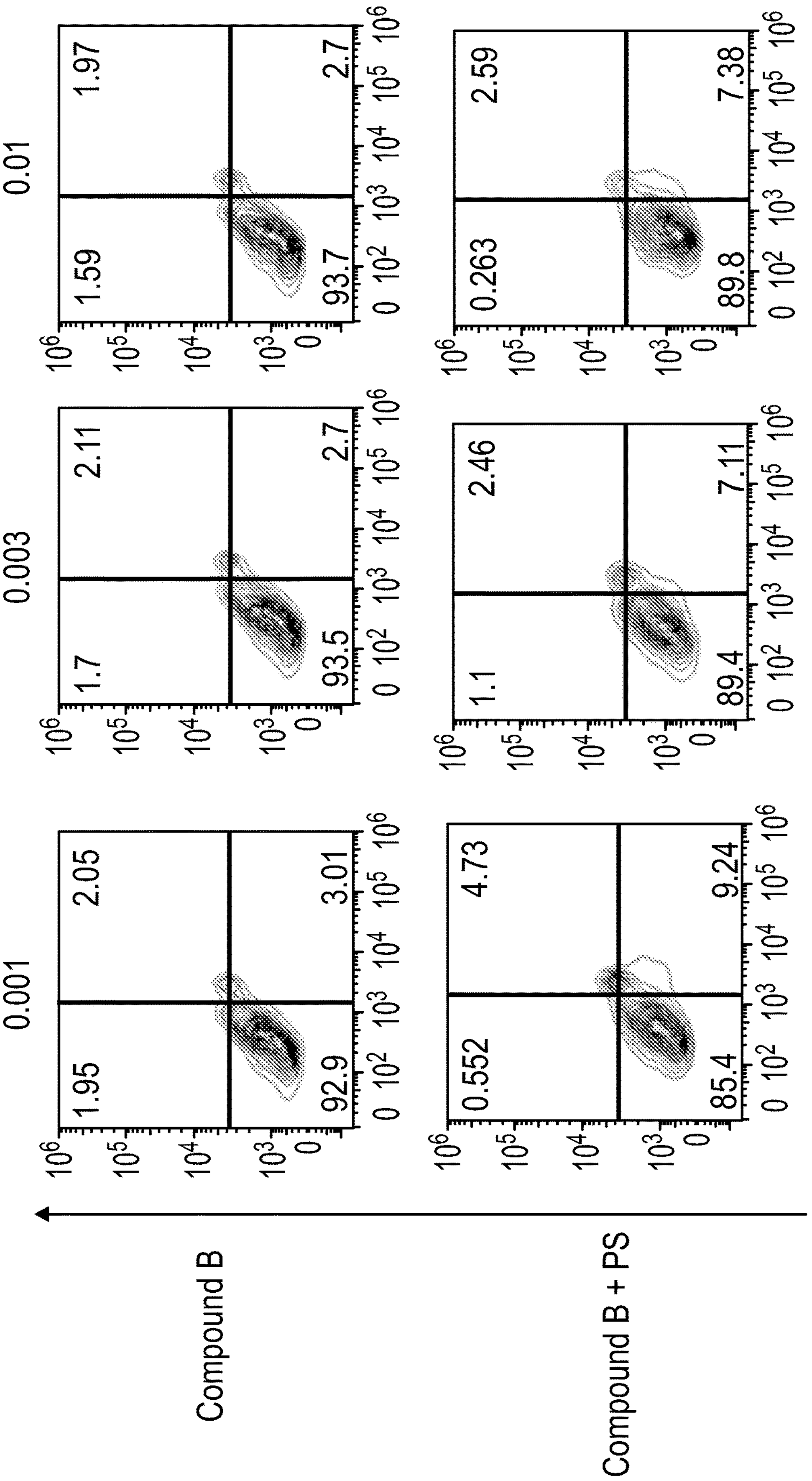
FIG. 3K shows TIM3+/PD-1+ in Compound B-treated cells in the presence and absence of PS.
Figure 3K:
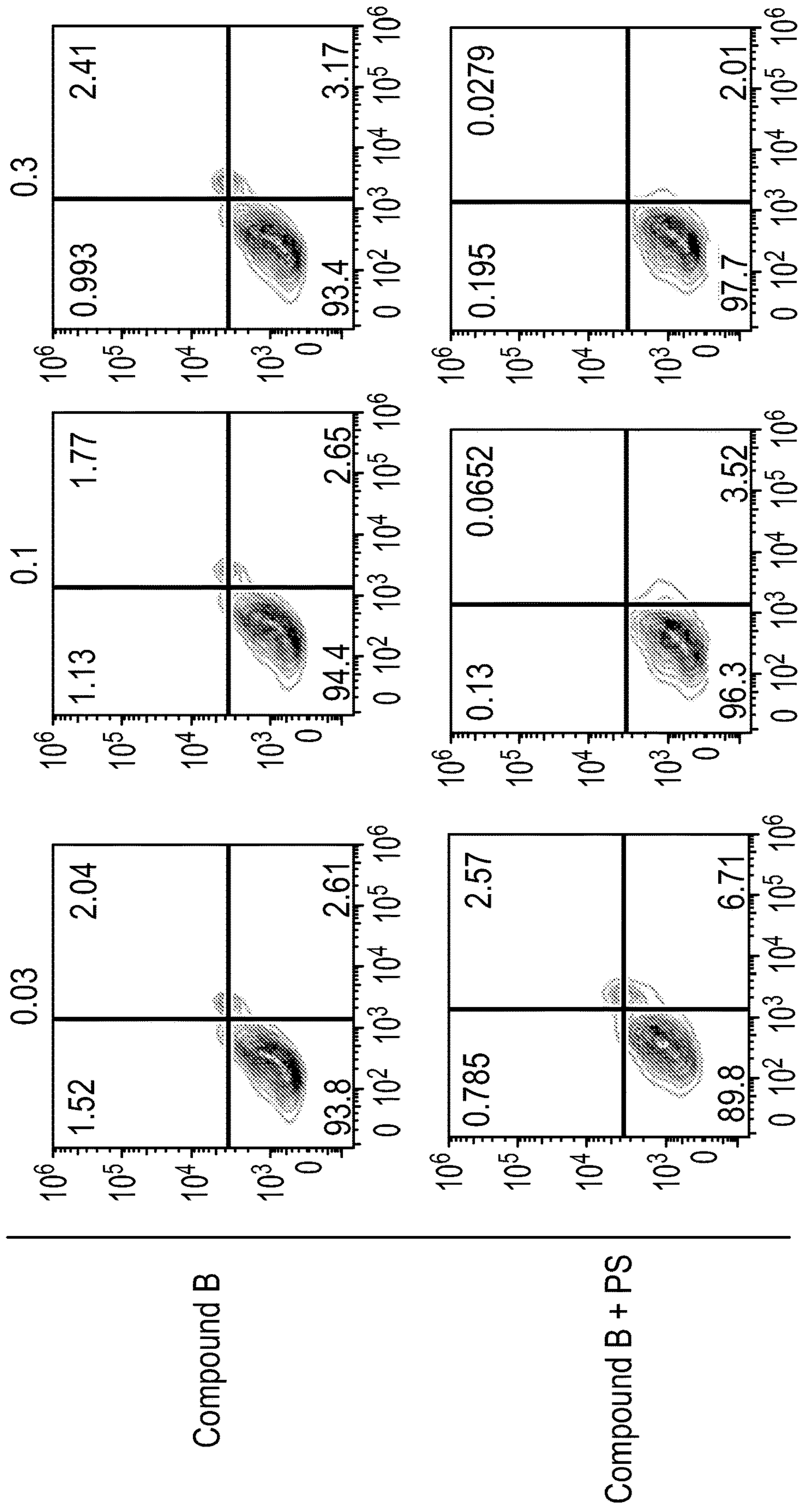
Figure 3K:
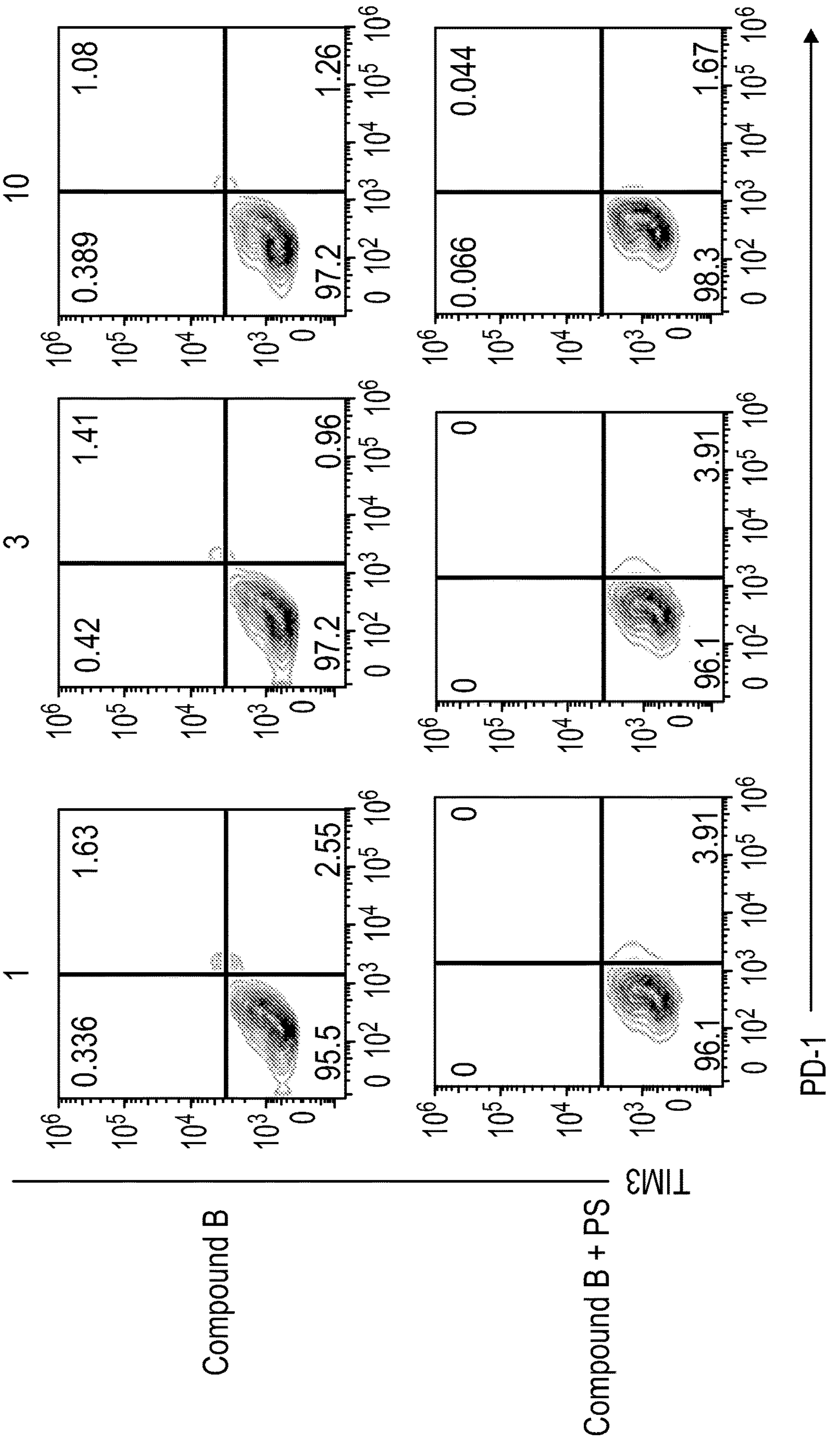

Results of treatment groups: Cells treated with low dose ConA (10 g/ml) and increasing doses of compound B in the absence of PS liposomes showed a reduction in TIM3+/PD-1+ double-positive CD8+ T-cells when compared to CTL control (FIG. 3K, upper panel versus FIG. 3J, CTL panel). This reduction in TIM3+/PD-1+ double-positive CD8+ T-cells seemed to be independent of dose.

In the presence of 0.1 mM PS liposomes TIM3+/PD-1+ double-positive CD8+ T-cell count increased with low dose ConA (10 g/ml) and low dose compound B (0.001 mM). As doses of compound B increased, TIM3+/PD-1+ double-positive CD8+ T-cell count decreased to values observed in T-cells treated with compound B in the absence of PS (FIG. 3K, lower panel).

The fold change from baseline of TIM3+/PD-1+ double-positive CD8+ T-cells as a function of increasing doses of compound B was calculated using equation 1, where Responsecontrol was TIM3+/PD-1+ double-positive CD8+ T-cells in cells treated with IL-2 alone and Responsetreatment was TIM3+/PD-1+ double-positive CD8+ T-cells at each dose of compound B. The baseline PS response was calculated using the same equation with Responsetreatment as the TIM3+/PD-1+ double-positive CD8+ T-cells treated with 0.1 mM PS.

Figure 3L:
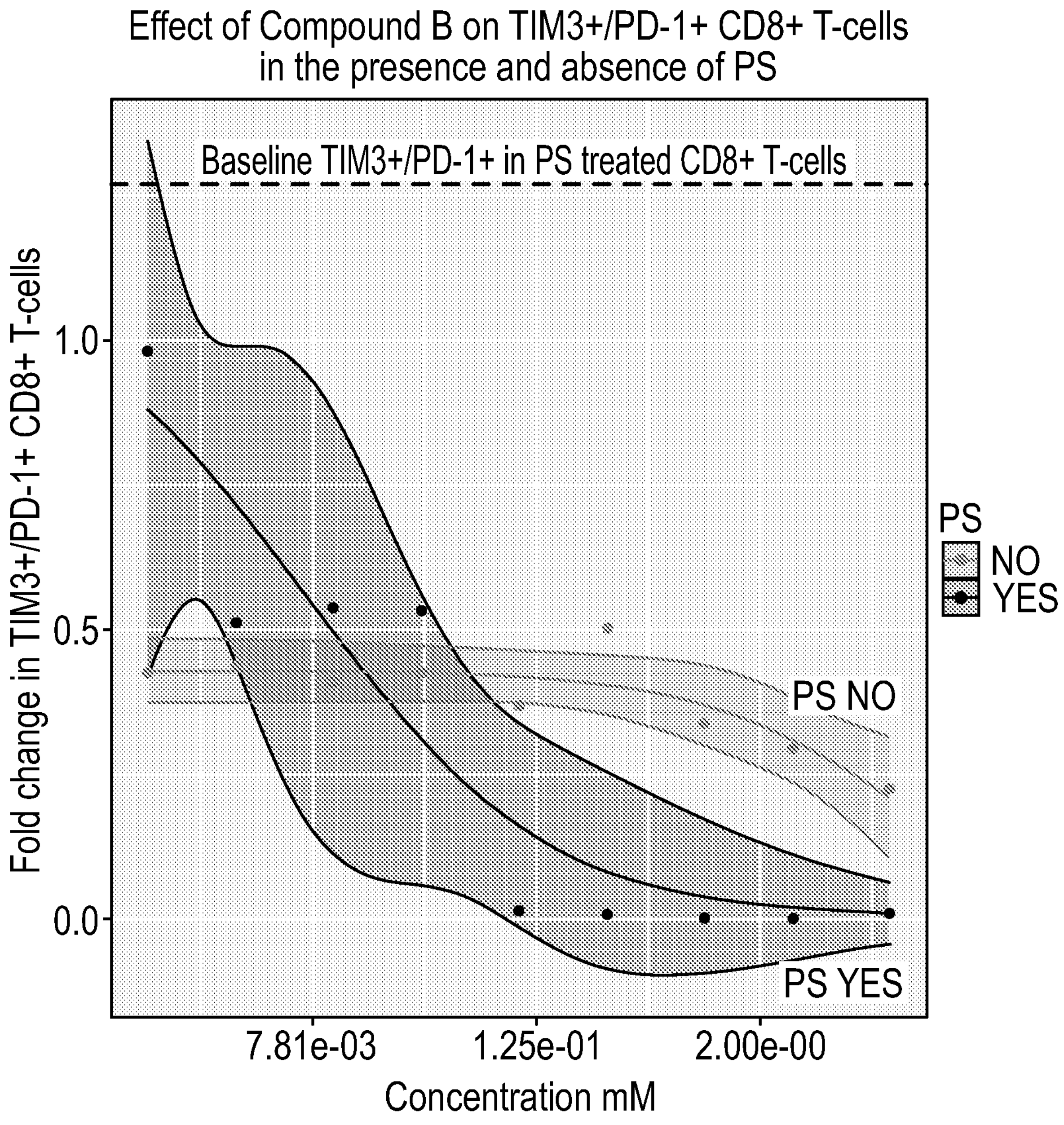
FIG. 3L shows concentration-response analysis of Compound B in the presence and absence of 0.1 mM PS (TIM3+/PD-1+).

PS increased the TIM3+/PD-1+ double-positive CD8+ T-cells by 1.27-fold compared to the negative control (dashed line in FIG. 3L). Treatment with increasing doses of compound B in the absence of PS resulted in a reduction in TIM3+/PD-1+ double-positive CD8+ T-cells in a dose-independent manner. The average reduction was about ⅗ lower than the negative control and about ⅔ less than 0.1 mM PS treated cells (flatter curve in FIG. 3L).

In the presence of 0.1 mM PS, compound B doses greater than 0.001 mM seemed to reverse the stimulatory effects of PS on TIM3+/PD-1+ double-positive CD8+ T-cells in a dose-independent manner as well (steeper curve in FIG. 3L). Further reduction in TIM3+/PD-1+ double-positive CD8+ T-cells at doses greater than 0.1 mM may be an artifact of activation-induced T-cell death similar to that observed in GzmB+/IFN-γ+ staining.

Figure 3M:
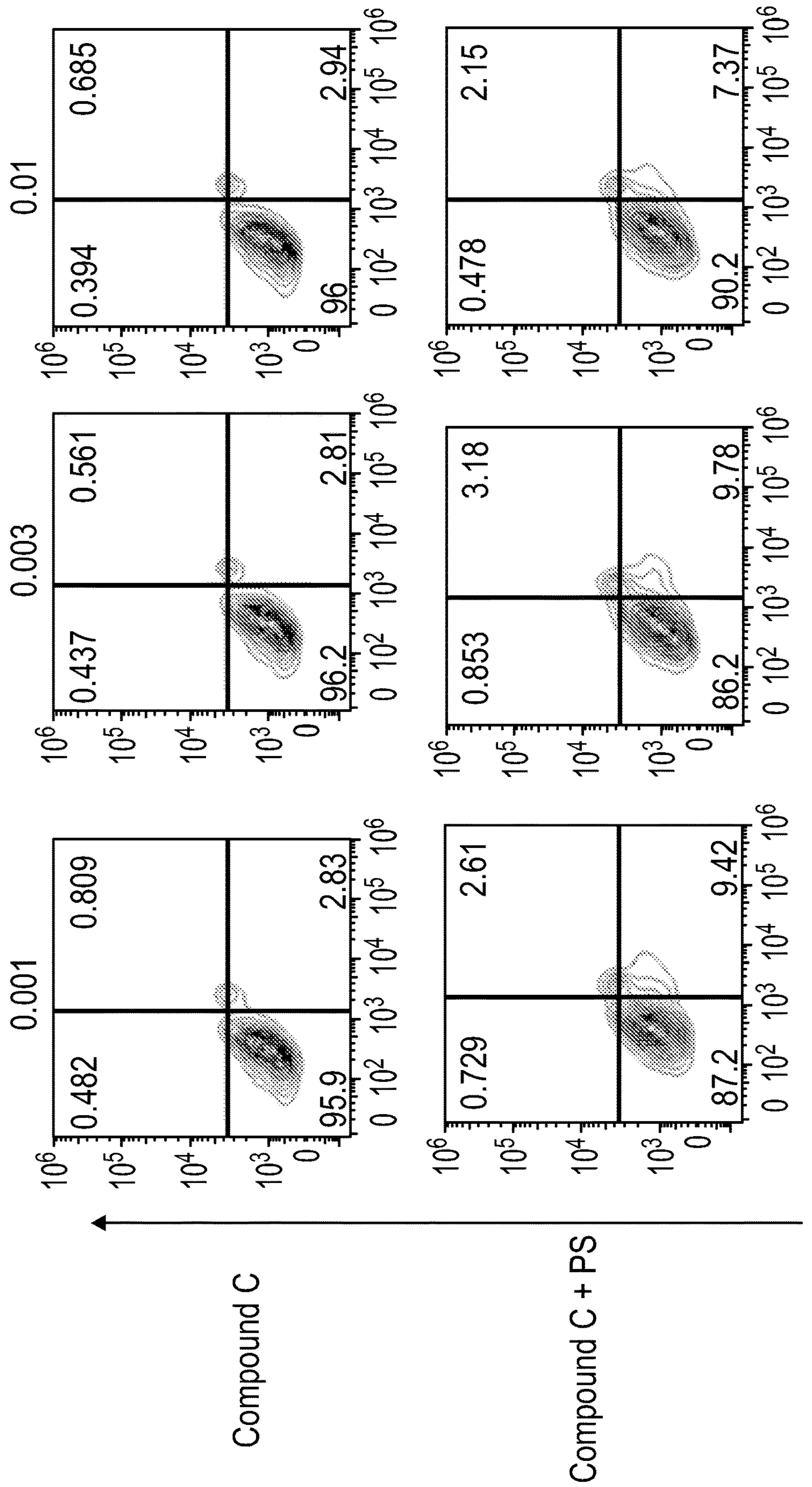
FIG. 3M shows TIM3+/PD-1+ in Compound C-treated cells in the presence and absence of PS.
Figure 3M:
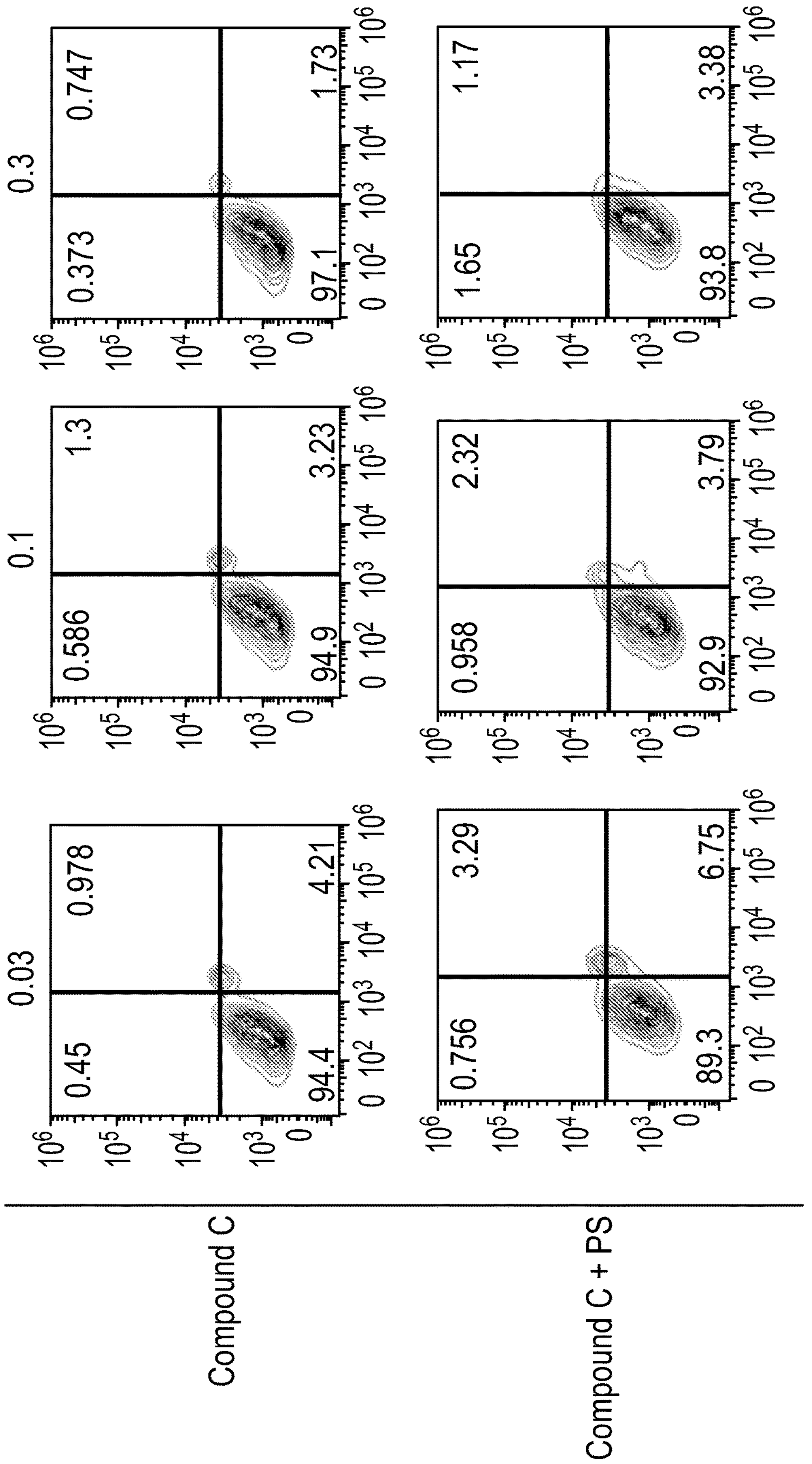
Figure 3M:
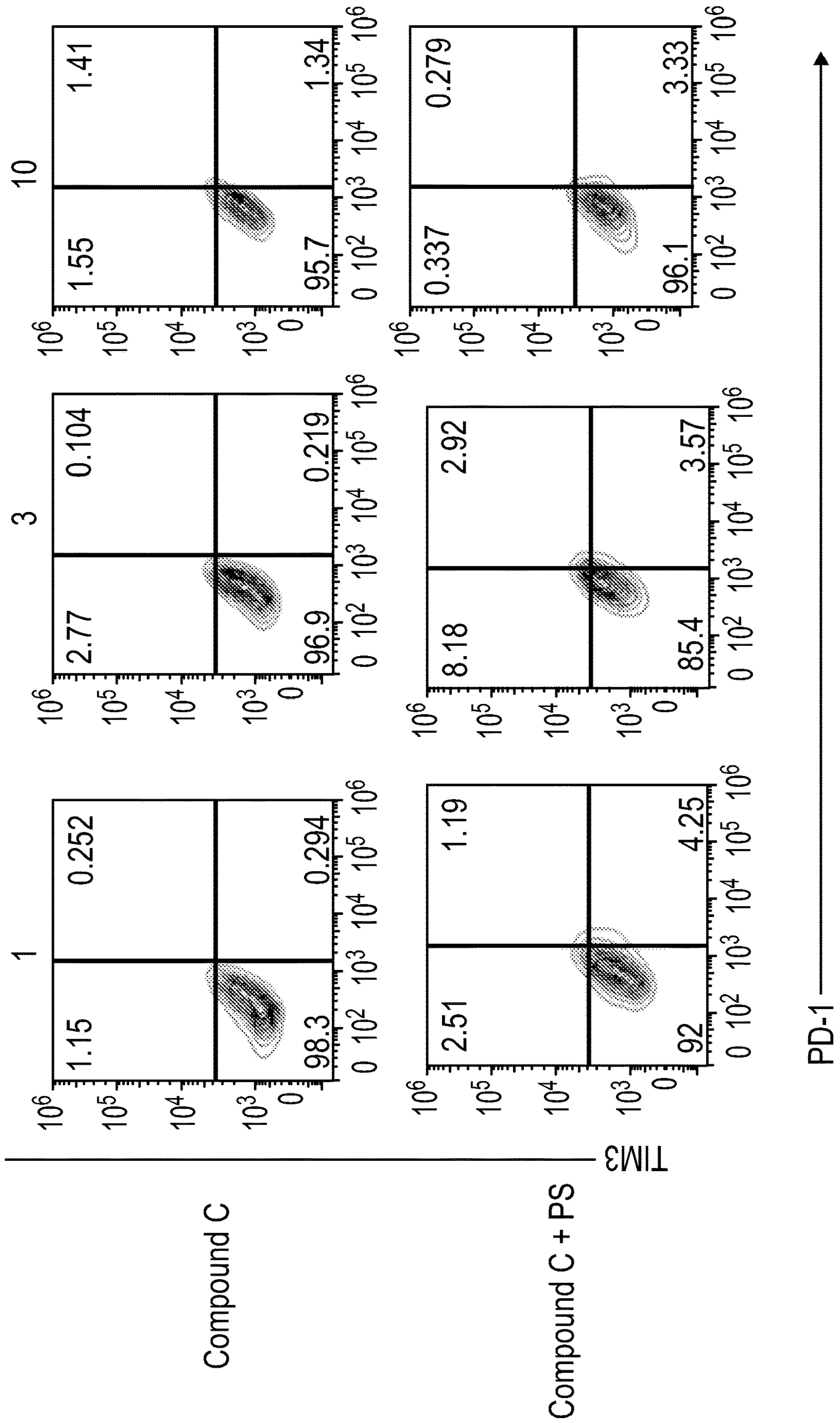

Cells treated with low dose ConA (10 g/ml) and increasing doses of compound C in the absence of PS liposomes showed a reduction in TIM3+/PD-1+ double-positive CD8+ T-cells when compared to control (FIG. 3M, upper panel versus FIG. 3J, CTL panel). This reduction in TIM3+/PD-1+ double-positive CD8+ T-cells seemed to be independent of dose.

In the presence of 0.1 mM PS liposomes, TMI3+/PD-1+ double-positive CD8+ T-cell count increased with low dose ConA (10 g/ml) and compound C compared to compound C treatment alone. However, the increase in TMI3+/PD-1+ double-positive CD8+ T-cell count was lower than both negative control and PS treated T-cells, suggesting compound C can reverse the stimulatory effect of PS on TMI3+/PD-1+ double-positive CD8+ T-cell count (FIG. 3M, lower panel).

Figure 3N:
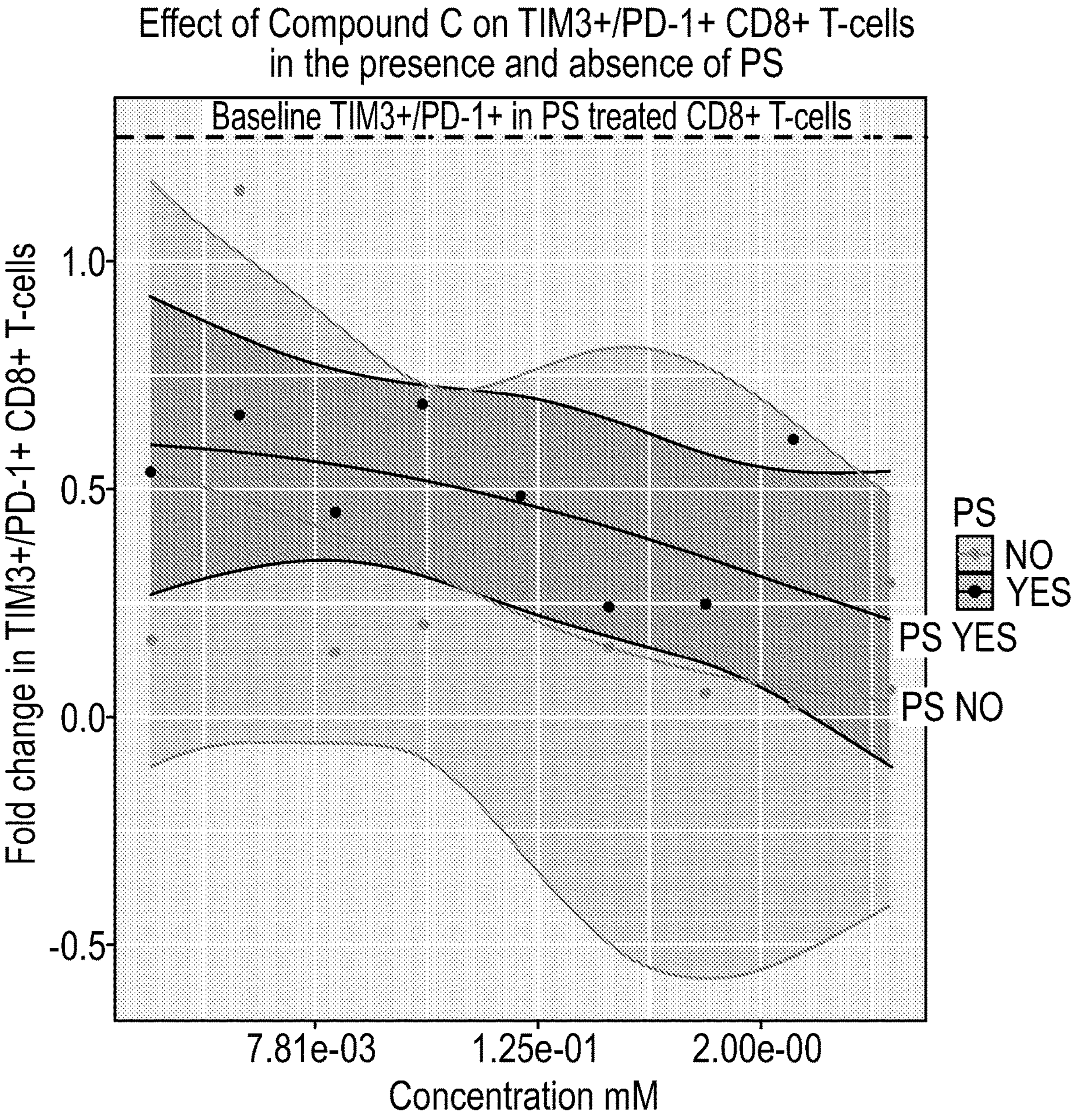
FIG. 3N shows concentration-response analysis of Compound C in the presence and absence of 0.1 mM PS (TIM3+/PD-1+).

The fold change from baseline TIM3+/PD-1+ double-positive CD8+ T-cells as a function of increasing doses of compound C was calculated as described for compound B. PS increased the TIM3+/PD-1+ double-positive CD8+ T-cells by 1.27-fold compared to the negative control (dashed line in FIG. 3N). Treatment with increasing doses of compound C in the absence of PS resulted in a reduction in TIM3+/PD-1+ double-positive CD8+ T-cells in a dose-independent manner. The average reduction was about ⅔ lower than the negative control and about ⅘ less than 0.1 mM PS treated cells (left-shifted curve in FIG. 3N).

Discussion: Overall data presented in this example support the notion that compounds B and C can counteract the effect of PS on T-cells in vitro. PS is the natural ligand of TIM3 and TIM4, and is also a known inhibitor of T-cell activation. Both compounds B and C restored T-cell proliferation in cells treated with 0.1 mM PS in a dose-dependent manner.

Beyond T-cell proliferation, the functionality of T-cells was also assessed. The cytotoxic serum protease Granzyme B (GzmB) and IFN-γ, which is primarily secreted by activated T cells, were assessed after treatment with compound B or C. In the absence of PS, both compounds B and C produced a robust increase in GzmB+/IFN-γ+ double-positive T-cells count. Furthermore, both compounds B and C reversed the inhibitory effects of PS on GzmB and IFN-γ in a dose-dependent manner up to 0.1 mM; beyond 0.1 mM the production and GzmB and IFN-γ were reduced. This could be due to activation-induced cell death often observed when immune cells are hyper-stimulated. In potent stimulation conditions, T cells can exponentially proliferate and secrete a huge amount of cytokines in the environment. Since this is an in vitro experiment, this can lead to death for T cells themselves. The tested compounds could be potent enough that, at low doses, T-cells proliferate and maintain their anti-tumor function with minimal exhaustion, while at higher doses, they proliferate and induce self-death. Thus, this finding does not contradict the findings of the proliferation assay. T-cells could proliferate and then undergo activation-induced cell death.

Finally, two checkpoints were evaluated in this study: TIM3 and PD-1. A reduction in both checkpoints at almost all tested dose levels was observed. TIM3+/PD-1+ double-positive CD8+ T-cells counts were consistently lower in compound B- or compound C-treated cells compared to unactivated cells (negative control) and cells treated with 0.1 mM PS. The lack of dose-response (or the very shallow slopes observed) could be an indication of a binary type of response, or more likely the doses tested were on asymptote indicating a maximal response. It is noteworthy that reduction in TIM3 and PD-1 at doses higher than 0.1 mM (although used in model fitting) is expected to be an artifact of activation-induced cell death discussed before.

Conclusions: Based on the analysis in this study, a target concentration of 0.1 mM will be considered an effective dose for compound B. Data from compound C was less conclusive, however, future studies will target 0.1 mM and will continue to seek to refine the dose for compound C.

Example 8. FoxP3/KLRG-1 Expression in CD4+/CD8+ T-Cells Isolated from Compound D-Treated Animals Animals were treated with 2.5 mg of compound D IV daily for seven days. Upon completion of the treatment period, T-cells isolated from spleens of the animals were analyzed by flow cytometry. Animals treated with compound D had 58% reduction in FoxP3+ CD4+ T-cells compared to control animals (130.1% to 5.42%). Animals treated with compound D also had 80% reduction in KLRG-1+/CD8+ T-cells (from 25.8% to 5.11%), and 27% reduction in CTA4+/CD8+ T-cells (from 0.37% to 0.27%).

Example 9. Dose-Response Analysis of Compounds B-E in Murine T-Cells

A dose-response analysis of compounds B-E in murine CD8+ T-cells was conducted to evaluate the effect of dose on GranzymeB/IFN-γ double positivity.

Compound B was dissolved in PBS to the desired concentration and pH was adjusted as needed to pH approximately 7.5. Compound C, D and E were first dissolved in a small volume of DMSO before diluting to the final desired concentration. DMSO did not exceed 15% v/v. pH was adjusted as needed to approximately 7.5.

Splenocytes from naïve C57BL/6 mice were stained with CFSE, prepared, cultured, and dosed. Cells were seeded at $2\times10^5$ cells/well. Negative control was dosed with 10 ng/ml IL-2. After ConA stimulation (10 μg/ml), cells were dosed with log 3 dilution of each compound from $3\times10^{-9}$ to 30 M in triplicates. All wells were dosed with 10 ng/ml of IL-2.

Flow cytometer analysis was performed to assess percent CD8+ T-cells and percent activation by double staining for Granzyme B (GzmB) and IFN-γ as described in Example 7. Concentration versus response curve was fitted to a 4- or 5-parameter log-logistic model using the "dre" package in "R". Both $EC_{50}$ and $EC_{90}$ were obtained by model fitting.

Cells were observed via a microscope at the end of the incubation period. Controls looked healthy and were selected for flow analysis. T cell clusters were observed throughout the incubation period. Cluster formation, a sign of proliferation, was observed in all treatment groups. Generally, all cells looked healthy and suitable for flow cytometry analysis.

Visual inspection of the model fit suggested that a 5-parameter dose-response model captured the data from compounds B-E, especially capturing the plateau for compounds C and E better than a 4-parameter model (data not shown). Table 3 summarizes the $EC_{50}$ and $EC_{90}$ values obtained by model fitting.

TABLE 3

Summary of $EC_{50}$ and $EC_{90}$ Values by Model Parameters and Treatment

| Model | EC50, μM | | EC90, μM | |
|---|---|---|---|---|
| Parameter | 4 | 5 | 4 | 5 |
| Compound B | 9.8E−03 | 1.1E−02 | 9.5E−01 | 3.0E+00 |
| Compound D | 4.1E−03 | 3.5E−03 | 5.0E−02 | 3.9E−02 |
| Compound E | 9.3E−02 | 2.3E−02 | 1.2E+02 | 6.0E−01 |
| Compound C | 4.3E−02 | 4.2E−02 | 2.9E+01 | 2.8E+01 |

Figure 4:
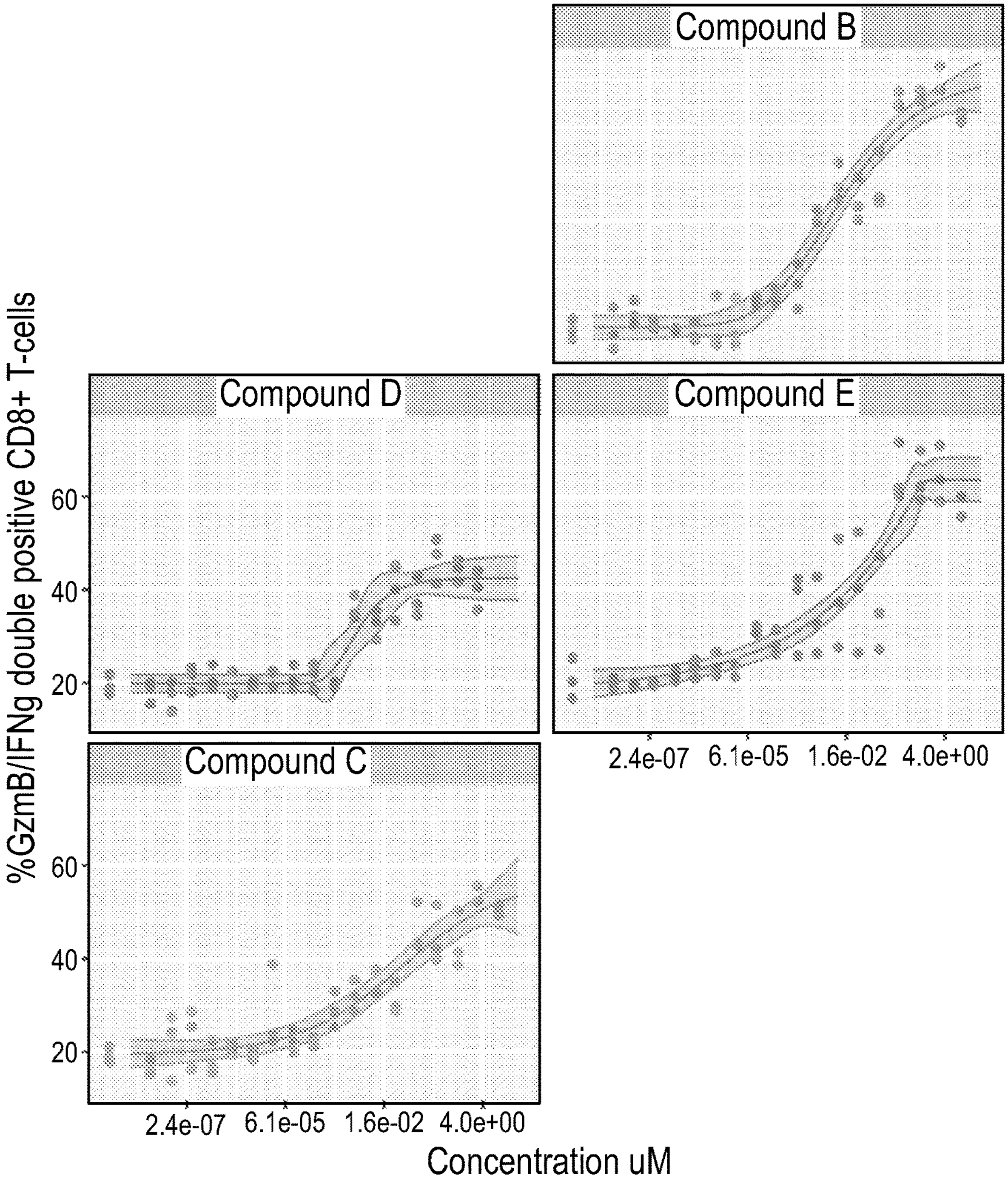
FIG. 4 shows in vitro dose-response data fitted to a 5-parameter model in R.

Raw data, as well as model fitting, suggested that maximal response to Compounds B, C and E was greater than that to Compound D. FIG. 4 shows that maximal response for Compounds B, C and E approached or exceeded 60% versus 40% for Compound D.

Example 10. Dose-Pharmacodynamics of Compound B in Melanoma Murine Model

The pharmacodynamic (PD) effects of a single IV dose of Compound B in a melanoma murine model were evaluated. B16F10 melanoma cells were grown in RPMI 1640 media supplemented with 10% FBS and antibiotics (penicillin/streptomycin) using T75 flasks. When cells reached 70-80% confluency, they were treated with 3 ml of 0.25% Trypsin/EDTA. Afterward, detached cells were harvested. A single-cell suspension was prepared in PBS. An IV injection of $10^5$ cells in mice marked day −3 of the experiment.

In a prior study, Compound B was dosed at 4 mg PO QD for seven days. At this dose, Compound B showed efficacy for overall survival, delay in tumor progression and changes in PD markers KLRG-1, CTLA-4, TIM3 and PD-1. Compound B has an oral bioavailability of approximately 30% (data not shown).

Animals were housed four per cage, and had access to food and water ad libitum. Three days after IV injection of melanoma cells, animals were dosed as per their group assignment, as shown in Table 4. Compound B was dissolved in sterile PBS, and pH was adjusted to approximately 7.5. Sterile PBS served as control.

TABLE 4

| Dosing Groups | | |
|---|---|---|
| Group | Dose mg/mouse (route) | n |
| Baseline | NA | 3 |
| Control | 0 (IV) | 9 |
| Compound B | 0.7 (IV) | 9 |
| | 0.14 (IV) | 9 |
| | 1.4 (IV) | 9 |

Figure 5A:
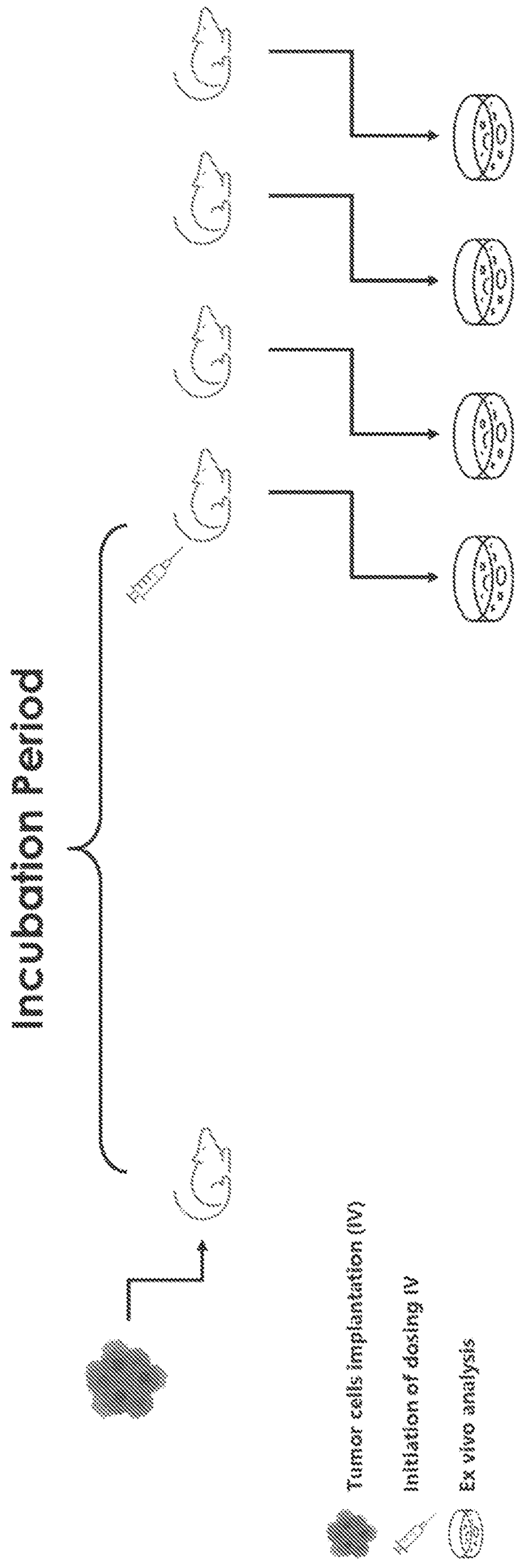
FIG. 5A is a diagram showing the design of the melanoma murine model described in Example 10.

Three days after the IV injection of melanoma cells, animals in the baseline group (n=3) were sacrificed and their spleens were collected for KLRG-1, CTLA-4, and PD-1 analysis. At each predetermined time-point (24, 48, and 120 hours after dosing) three animals from each group were sacrificed for splenocyte analysis of KLRG-1, CTLA-4, and PD-1 expression levels, and expression levels were compared to baseline. FIG. 5A shows a schematic diagram of the study design.

Spleens collected for splenocyte analysis were prepared into a single-cell suspension for cellular phenotyping by flow cytometry. Cells were stained and gated for CD8. Percent KLRG-1+, CTLA-4+, and PD-1+ CD8+ T-cells were evaluated using flow cytometry.

Figure 5B:
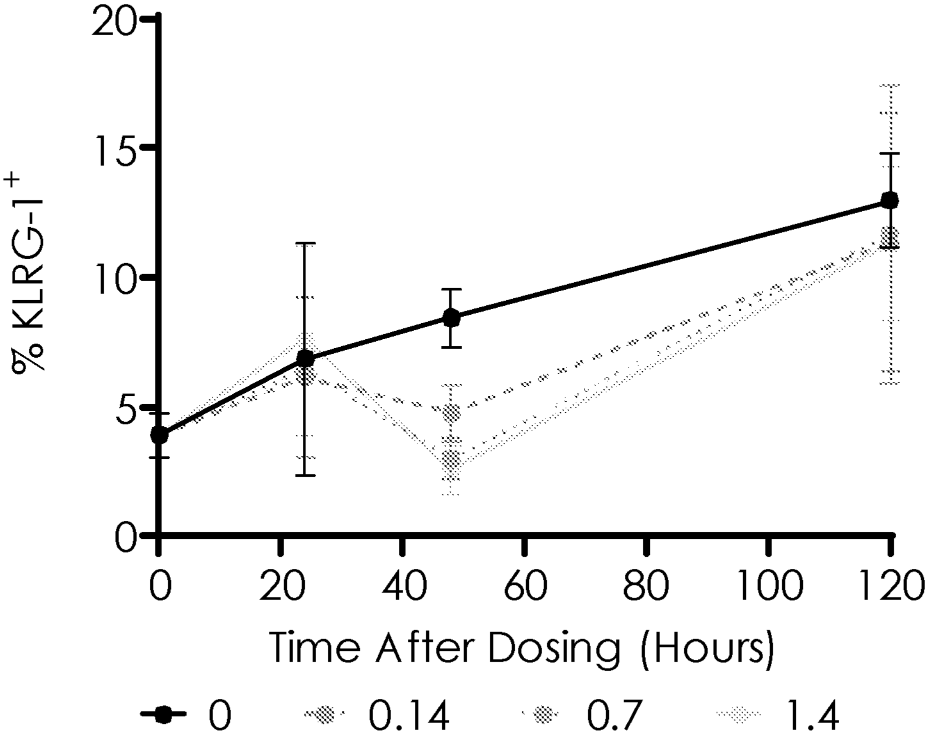
FIG. 5B shows change in percent KLRG-$1^+$/$CD8^+$ T-cells over time in the melanoma murine model described in Example 10 by treatment group after a single dose of Compound B.

The percent of KLRG-1+/CD8+ T-cells increased in the untreated group from a baseline value of 3.9% (0.8) 3 days after IV injection of melanoma cells to 13.0% (1.8) by end of the study (mean (SD)), representing a 232% increase. In contrast, KLRG-1+/CD8+ T-cells decreased in all treatment groups in a dose-independent manner by 48 hours post-treatment before increasing again parallel to the control group. Percent KLRG-$1^+$/CD8+ T-cells at 48 hours was 4.8% (1.1), 3.0 (0.8), 2.5% (0.9) (mean (SD)) for 0.14 mg, 0.7 mg, 1.4 mg IV groups, respectively, versus 8.4% (1.1) (mean (SD)) for the control group (Table 5). This represents a 23% to 36% decrease in KLRG-1+/CD8+ T-cells from baseline after a single 0.7 or 1.4 mg IV dose of Compound B. Compared to the same time point in the control group, a single IV injection with Compound B resulted in a 42% to 70% reduction in KLRG-1+/CD8+ T-cell for the 0.14 mg and the 1.4 mg doses, respectively. FIG. 5B shows the pharmacodynamic changes in percent KLRG-1+/CD8+ T-cell in response to a single Compound B dose by treatment group.

TABLE 5

| Summary statistics of KLRG-1+/CD8+ T-cells | | | | | | | | | | | | |
|---|---|---|---|---|---|---|---|---|---|---|---|---|
| Group | 0 | | | 0.14 | | | 0.7 | | | 1.4 | | |
| Time | mean | sd | n | mean | sd | n | mean | sd | n | mean | sd | n |
| 0 | 3.9 | 0.8 | 3.0 | 3.9 | 0.8 | 3.0 | 3.9 | 0.8 | 3.0 | 3.9 | 0.8 | 3.0 |
| 24 | 6.9 | 4.5 | 3.0 | 6.2 | 3.1 | 3.0 | 6.5 | 0.4 | 3.0 | 7.6 | 3.7 | 3.0 |
| 48 | 8.4 | 1.1 | 3.0 | 4.8 | 1.1 | 3.0 | 3.0 | 0.8 | 3.0 | 2.5 | 0.9 | 3.0 |
| 120 | 13.0 | 1.8 | 3.0 | 11.4 | 5.0 | 3.0 | 11.7 | 5.8 | 3.0 | 11.3 | 3.0 | 3.0 |

Figure 5C:
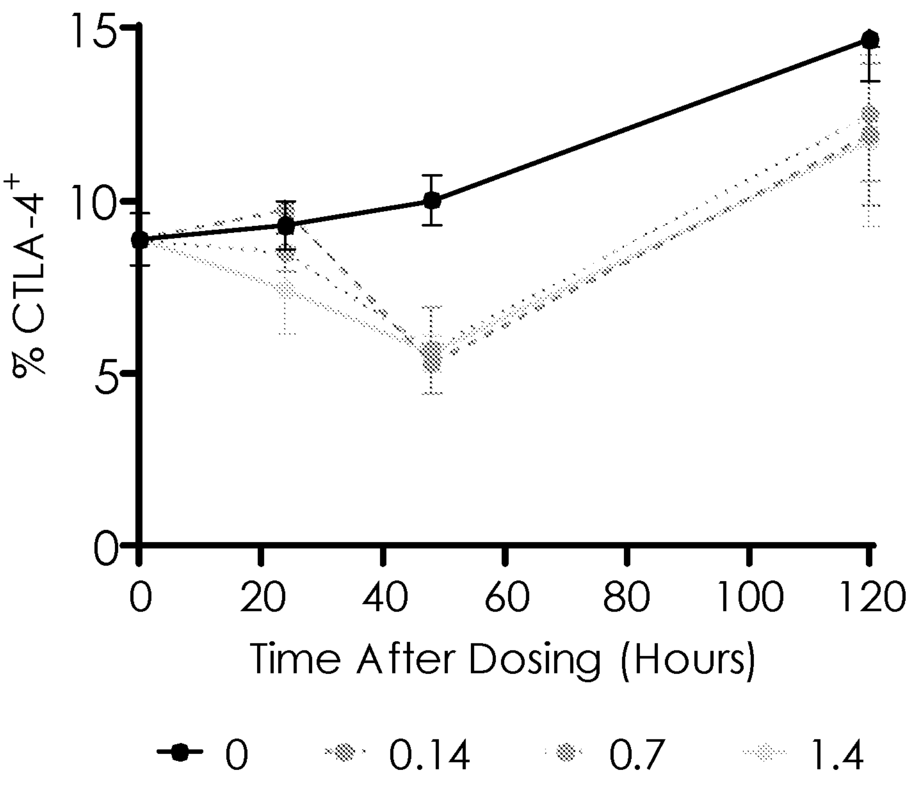
FIG. 5C shows change in percent CTLA-$4^+$/$CD8^+$ T-cells over time in the melanoma murine model described in Example 10 by treatment group after a single dose of Compound B.

The percent of CTLA-4+/CD8+ T-cells increased in the untreated group from a baseline value of 8.9% (0.8) 3 days after IV injection of melanoma cells to 14.7% (1.2) by end of the study (mean (SD)), representing a 65% increase. In contrast, CTLA-4+/CD8+ T-cells decreased at 48 hours post IV dosing with Compound B in all groups. Percent CTLA-4+/CD8+ T-cells increased after 48 hours parallel to the control group, however, values remained lower than the control group for the duration of the study. Percent CTLA-4+/CD8+ T-cells at 48 hours post-treatment was 5.3% (0.2), 5.7% (1.3), and 5.6% (0.5) (mean (SD)) for 0.14 mg, 0.7 mg, 1.4 mg IV groups, respectively (Table 6). This represents an approximately 35% decrease from baseline in CTLA-4+/CD8+ T-cells after a single dose of Compound B. Compared to the same time point in the control group, a single IV injection with Compound B resulted in an approximately 38% reduction in CTLA-4+/CD8+ T-cells. FIG. 5C shows the pharmacodynamic changes in percent CTLA-$4^+$/CD8+ T-cells in response to a single Compound B dose by treatment group.

TABLE 6

| Summary statistics of CTLA-4+/CD8+ T-cells | | | | | | | | | | | | |
|---|---|---|---|---|---|---|---|---|---|---|---|---|
| Group | 0 | | | 0.14 | | | 0.7 | | | 1.4 | | |
| Time | mean | sd | n | mean | sd | n | mean | sd | n | mean | sd | n |
| 0 | 8.9 | 0.8 | 3 | 8.9 | 0.8 | 3 | 8.9 | 0.8 | 3 | 8.9 | 0.8 | 3 |
| 24 | 9.3 | 0.7 | 3 | 9.8 | 0.2 | 3 | 8.5 | 0.5 | 3 | 7.4 | 1.3 | 3 |
| 48 | 10.0 | 0.7 | 3 | 5.3 | 0.2 | 3 | 5.7 | 1.3 | 3 | 5.6 | 0.5 | 3 |
| 120 | 14.7 | 1.2 | 3 | 11.9 | 2.1 | 3 | 12.5 | 1.9 | 3 | 11.7 | 2.5 | 3 |

Figure 5D:
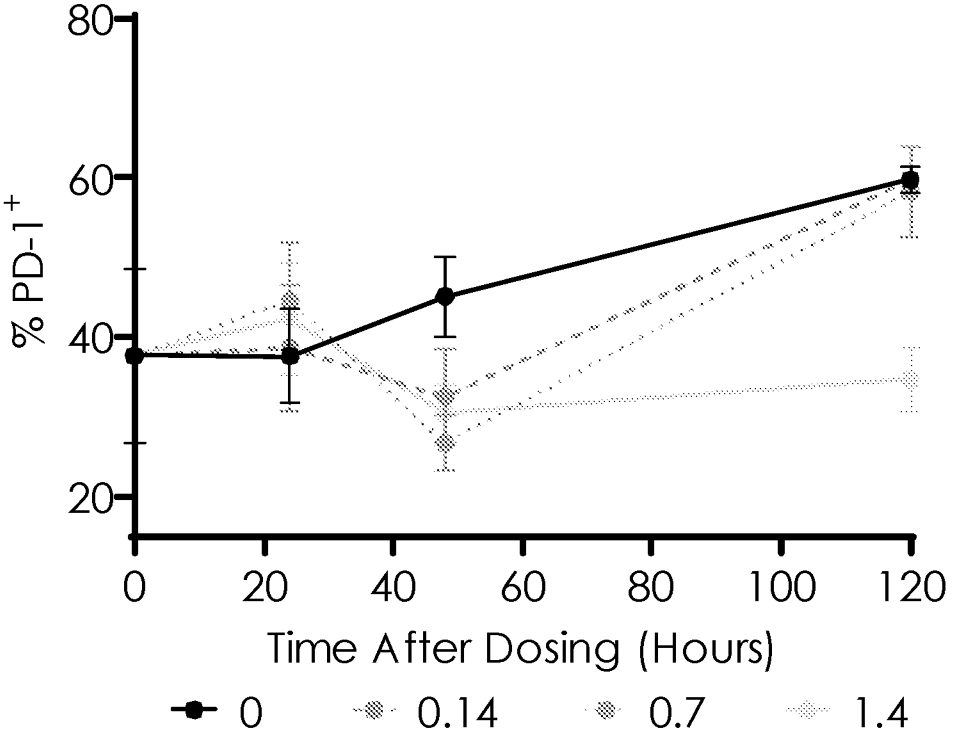
FIG. 5D shows change in percent PD-$1^+$/$CD8^+$ T-cells over time in the melanoma murine model described in Example 10 by treatment group after a single dose of Compound B.

The percent of PD-1+/CD8+ T-cells increased in the untreated group from a baseline value of 37.6% (11) 3 days after IV injection of melanoma cells to 59.7% (1.7) by end of the study (mean (SD)), representing a 58% increase. In contrast, PD-1+/CD8+ T-cells decreased at 48 hours post IV dosing with Compound B in all groups. Percent PD-1+/CD8+ T-cells at 48 hours post-treatment was 32.5% (6.1), 26.7% (3.5), and 30.4% (3.7) (mean (SD)) for 0.14 mg, 0.7 mg, and 1.4 mg IV groups, respectively (Table 7). This represents between 130.5% and 28.9% decrease from baseline in PD-1+/CD8+ T-cell after a single dose of Compound B. Compared to the same time point in the control group, a single IV injection with Compound B resulted in a 27.9% to 40.7% reduction in PD-1+/CD8+ T-cells in the treated groups (Table 7). The high dose group showed a sustained reduction in PD-1+/CD8+ T-cell compared to baseline and the other two treatment groups. By day 5, the 1.2 mg group showed a 41.8% reduction in PD-1+/CD8+ T-cell compared to control and the 0.14- and 0.7-mg treated mice. FIG. 5D shows the pharmacodynamic changes in percent PD-1+/CD8+ T-cell in response to a single Compound B dose by treatment group.

TABLE 7

| Summary statistics of PD-1+/CD8+ T-cells | | | | | | | | | | | | |
|---|---|---|---|---|---|---|---|---|---|---|---|---|
| Group | 0 | | | 0.14 | | | 0.7 | | | 1.4 | | |
| Time | mean | sd | n | mean | sd | n | mean | sd | n | mean | sd | n |
| 0 | 37.6 | 11.0 | 3 | 37.6 | 11.0 | 3 | 37.6 | 11.0 | 3 | 37.6 | 11.0 | 3 |
| 24 | 37.6 | 5.9 | 3 | 38.6 | 7.9 | 3 | 44.5 | 7.3 | 3 | 42.3 | 7.1 | 3 |
| 48 | 45.1 | 5.0 | 3 | 32.5 | 6.1 | 3 | 26.7 | 3.5 | 3 | 30.4 | 3.7 | 3 |
| 120 | 59.7 | 1.7 | 3 | 59.7 | 1.7 | 3 | 58.2 | 5.7 | 3 | 34.7 | 4.1 | 3 |

Data from this study support Compound B's ability to down-regulate early and late exhaustion markers KLRG-1, CTLA-4, and PD-1 after a single IV dose. This is in line with earlier findings after oral dosing with Compound B. Down-regulation of exhaustion markers is a key factor in the anti-tumor effects of this class of TIM antagonists. Interestingly, the nadir was seen 48 hours after dosing, almost two days after Compound B was expected to wash out based on the half-life of Compound B after IV dosing in mice. This temporal delay in PD is in line with observations made with antibody-based immunooncology (I/O) therapies.

Example 11. Dose-Pharmacodynamics of Compound C in Melanoma Murine Model

The PD effects of a single IV dose of Compound C were evaluated in a melanoma murine model conducted as described in Example 10. A prior study showed that Compound C was not orally bioavailable. This study also evaluated whether Compound C was pharmacodynamically active orally.

In a prior study, Compound C was dosed at 1 mg IV QD for seven days. At this dose, Compound C showed efficacy for overall survival, delay in tumor progression and changes in PD markers KLRG-1, CTLA-4, TIM3 and PD-1. In this study, Compound C was dosed as shown in Table 8. A single PO dose was chosen to confirm oral activity of Compound C. Compound C was dissolved in DMSO, and then diluted in sterile PBS. pH was adjusted to approximately 7.5. DMSO in the final formulation did not exceed 15% v/v.

TABLE 8

| Dosing Groups | | |
|---|---|---|
| Group | Dose mg/mouse (route) | n |
| Baseline | NA | 3 |
| Control | 0 (IV) | 9 |
| | 0.025 (IV) | 9 |
| | 0.1 (IV) | 9 |
| Compound C | 0.25 (IV) | 9 |
| | 1.0 (IV) | 9 |
| | 2.5 (PO) | 9 |

Figure 6A:
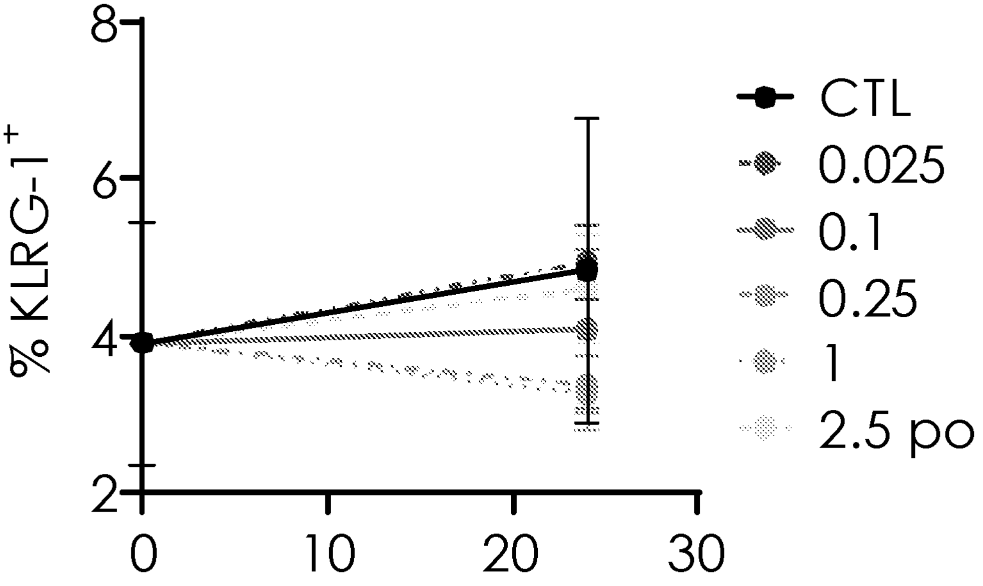
FIG. 6A shows change in percent KLRG-$1^+$/$CD8^+$ T-cells over time in the melanoma murine model described in Example 11 by treatment group after a single dose of Compound C.

The percent of KLRG-1+/CD8+ T-cells increased in the untreated group from a baseline value of 3.9% (1.8) 3 days after IV injection of melanoma cells to 4.8% (1.9) by end of the study (mean (SD)), representing a 23% increase. In contrast, the 0.25- and 1-mg IV groups showed an approximately 15% decrease in KLRG-1+/CD8+ T-cells compared to baseline and an approximately 31% decrease in KLRG-$1^+$/CD8+ T-cells compared to time match control (Table 9 and FIG. 6A). No meaningful changes were observed for the remaining groups compared to baseline or control.

TABLE 9

| Summary statistics of KLRG-1+/CD8+ T-cells (mean = mn) | | | | | | | | | |
|---|---|---|---|---|---|---|---|---|---|
| Group | 0 | | | 0.025 | | | 0.1 | | |
| Time | mn | sd | n | mn | sd | n | mn | sd | n |
| 0 | 3.9 | 1.5 | 3 | 3.9 | 1.5 | 3 | 3.9 | 1.5 | 3 |
| 24 | 4.8 | 1.9 | 3 | 4.9 | 0.5 | 3 | 4.1 | 1.0 | 3 |
| Group | 0.25 | | | 1 | | | 2.5 po | | |
| Time | mn | sd | n | mn | sd | n | mn | sd | n |
| 0 | 3.9 | 1.5 | 3 | 3.9 | 1.5 | 3 | 3.9 | 1.5 | 3 |
| 24 | 3.4 | 0.4 | 3 | 3.3 | 0.5 | 3 | 4.6 | 0.7 | 3 |

Figure 6B:
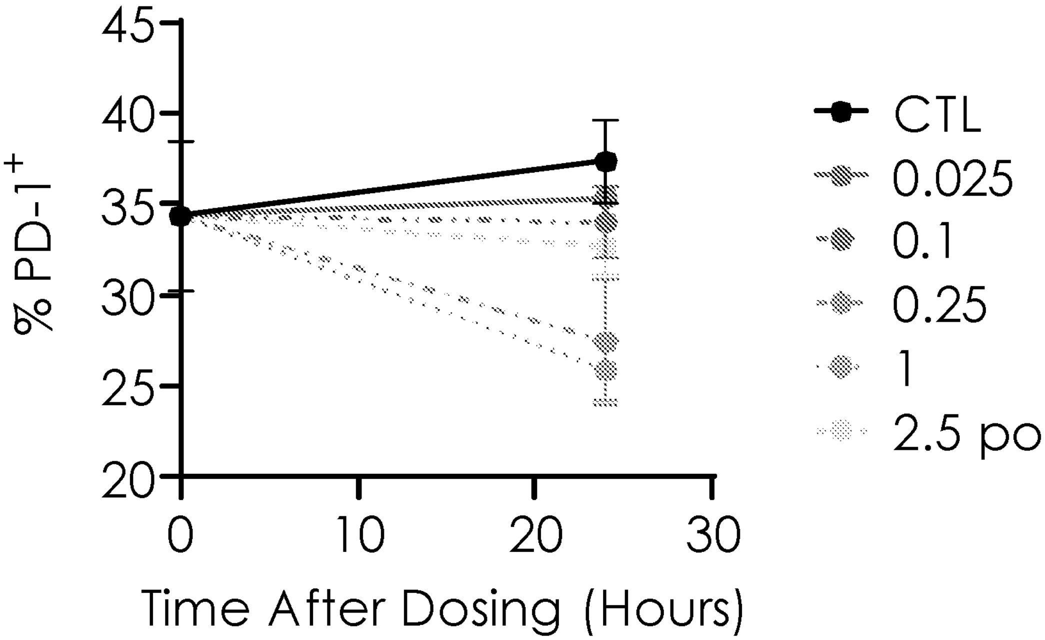
FIG. 6B shows change in percent PD-$1^+$/$CD8^+$ T-cells over time in the melanoma murine model described in Example 11 by treatment group after a single dose of Compound C.

The percent of PD-1+/CD8+ T-cells increased in the untreated group from a baseline value of 34.3% (4.2) 3 days after IV injection of melanoma cells to 37.3% (2.3) by end of the study (mean (SD)), representing an 8.7% increase. In contrast, the 0.25- and 1-mg IV groups showed an approximately 20% decrease in PD-1+/CD8+ T-cells compared to baseline and an approximately 30% decrease in PD-1+/CD8+ T-cells compared to time match control (Table 10 and FIG. 6B). No meaningful changes were observed for the remaining groups compared to baseline or control.

TABLE 10

| Summary statistics for PD-1+/CD8+ T-cells | | | | | | | | | |
|---|---|---|---|---|---|---|---|---|---|
| Group | 0 | | | 0.025 | | | 0.1 | | |
| Time (h) | mean | sd | n | mean | sd | n | mean | sd | n |
| 0 | 34 | 4.2 | 3 | 34 | 4.2 | 3 | 34 | 4.2 | 3 |
| 24 | 37 | 2.3 | 3 | 35 | 0.6 | 3 | 34 | 2.0 | 3 |
| Group | 0.25 | | | 1 | | | 2.5 po | | |
| Time (h) | mean | sd | n | mean | sd | n | mean | sd | n |
| 0 | 34 | 4.2 | 3 | 34 | 4.2 | 3 | 34 | 4.2 | 3 |
| 24 | 27 | 3.5 | 3 | 26 | 1.6 | 3 | 33 | 1.5 | 3 |

Data from this study confirmed that Compound C was not orally effective at the tested dose, which was 3.3-fold higher than the dose used previously. Although Compound C did show efficacy at 0.25 and 1 mg, the lack of oral bioavailability makes it a better candidate for use as a tool compound, for example, in vitro to compare against new molecules for efficacy and/or SAR studies.

Example 12. Dose-Pharmacodynamics of Compound E in Melanoma Murine Model

The oral and intravenous PD effects of a single dose of Compound E were evaluated in a melanoma murine model conducted as described in Example 10.

In this study, Compound E was dosed as shown in Table 11. Compound E was dissolved in DMSO, and then diluted in sterile PBS. pH was adjusted to approximately 7.5.

TABLE 11

| Dosing groups | | |
|---|---|---|
| Group | Dose mg/mouse (route) | n |
| Baseline | NA | 3 |
| Control | 0 (IV) | 9 |

TABLE 11-continued

| Dosing groups | | |
|---|---|---|
| Group | Dose mg/mouse (route) | n |
| Compound E | 0.1 (IV) | 9 |
| | 0.25 (IV) | 9 |
| | 1 (IV) | 9 |
| | 2.5 (PO) | 9 |

Figure 7A:
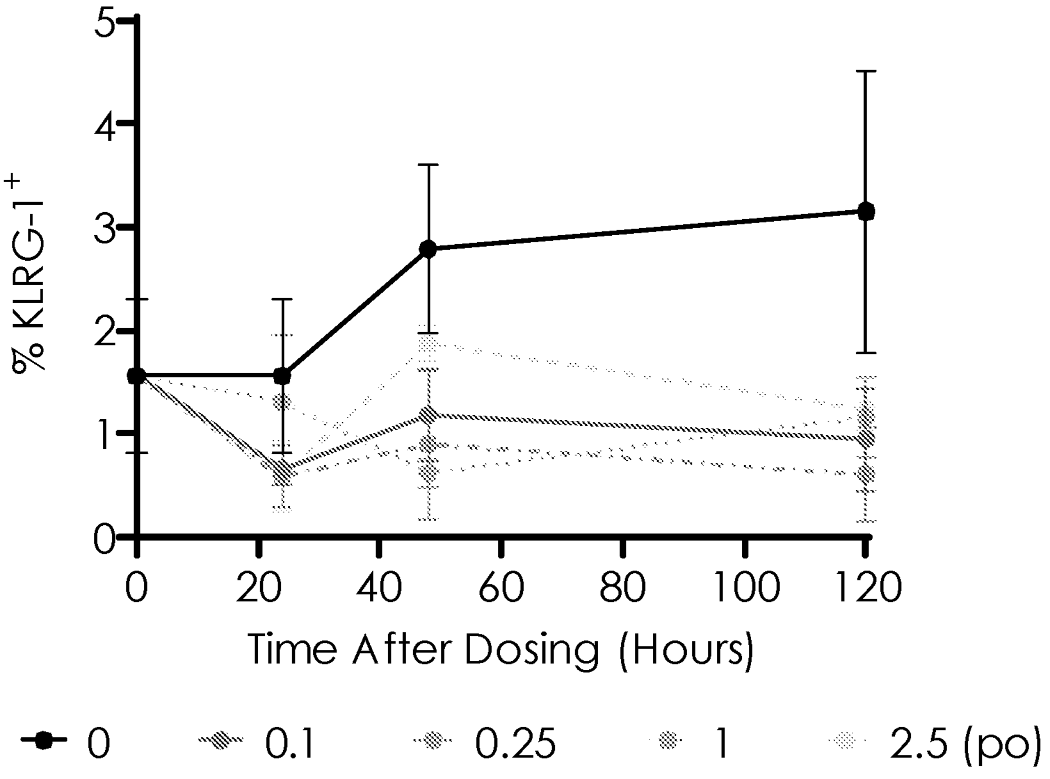
FIG. 7A shows change in percent KLRG-$1^+$/$CD8^+$ T-cells over time in the melanoma murine model described in Example 12 by treatment group after a single dose of Compound E.

The percent of KLRG-1+/CD8+ T-cells increased in the untreated group from a baseline value of 1.6% (0.8) 3 days after IV injection of melanoma cells to 3.2% (1.4) by end of the study (mean (SD)), representing a 102% increase. In contrast, KLRG-1+/CD8+ T-cells decreased in all treatment groups in a dose-independent manner by 24-hours post-treatment and maintained the decrease over the duration of the study. Percent KLRG-1+/CD8+ T-cells at end of the study was 1.0% (0.5), 0.6 (0.5), 1.2% (0.4) and 1.2% (0.2) (mean (SD)) for 0.1 mg, 0.25 mg, 1 mg IV and 2.5 mg PO groups, respectively (Table 12). This represents a 21% to 61% decrease in KLRG-1+/CD8+ T-cell after a single dose of Compound E. FIG. 7A shows the pharmacodynamic changes in percent KLRG-1+/CD8+ T-cell in response to a single Compound E dose by treatment group.

TABLE 12

Summary statistics of KLRG-1+/CD8+ T-cells

| Group | 0 | | | 0.1 | | | 0.25 | |
|---|---|---|---|---|---|---|---|---|
| Time | mean | sd | n | mean | sd | n | mean | sd |
| 0 | 1.6 | 0.8 | 3 | 1.6 | 0.8 | 3 | 1.6 | 0.8 |
| 24 | 1.6 | 0.8 | 3 | 0.7 | 0.2 | 3 | 0.6 | 0.3 |
| 48 | 2.8 | 0.8 | 3 | 1.2 | 0.5 | 2 | 0.9 | 0.7 |
| 120 | 3.2 | 1.4 | 3 | 1.0 | 0.5 | 2 | 0.6 | 0.5 |

| Group | 0.25 | 1 | | | 2.5 (po) | | |
|---|---|---|---|---|---|---|---|
| Time | n | mean | sd | n | mean | sd | n |
| 0 | 3 | 1.6 | 0.8 | 3 | 1.6 | 0.8 | 3 |
| 24 | 3 | 1.3 | 0.7 | 3 | 0.6 | 0.3 | 3 |
| 48 | 3 | 0.6 | 0.1 | 3 | 1.9 | 0.2 | 3 |
| 120 | 3 | 1.2 | 0.4 | 3 | 1.2 | 0.2 | 3 |

Figure 7B:
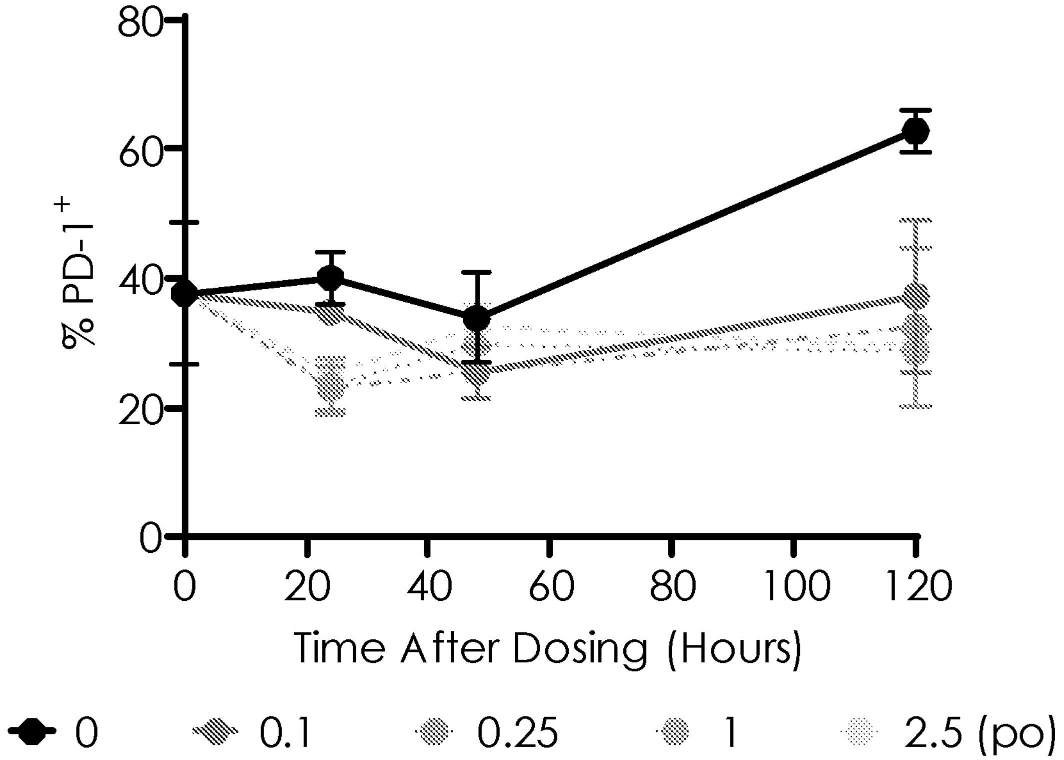
FIG. 7B shows change in percent PD-$1^+$/$CD8^+$ T-cells over time in the melanoma murine model described in Example 12 by treatment group after a single dose of Compound E.

The percent of PD-1+/CD8+ T-cells increased in the untreated group from a baseline value of 38% (11) 3 days after IV injection of melanoma cells to 63% (3) by end of the study (mean (SD)), representing a 65% increase. In contrast, PD-1+/CD8+ T-cells decreased at 24 hours post IV or PO dosing with Compound E in groups treated with 0.25 mg Compound E or higher, and those levels were maintained until the end of the study. Percent PD-1+/CD8+ T-cells at 24 hours post-treatment was 35% (2), 23% (3), 23% (4) and 25% (2) (mean (SD)) for 0.1 mg, 0.25 mg, 1 mg IV and 2.5 mg PO groups, respectively (Table 13). This represents an approximately 39% decrease from baseline in PD-1+/CD8+ T-cell after a single dose of Compound E. FIG. 7B shows the pharmacodynamic changes in percent PD-1+/CD8+ T-cell in response to a single Compound E dose by treatment group.

TABLE 13

Summary statistics of PD-1+/CD8+ T-cells

| Group | 0 | | | 0.1 | | | 0.25 | |
|---|---|---|---|---|---|---|---|---|
| Time | mean | sd | n | mean | sd | n | mean | sd |
| 0 | 38 | 11 | 3 | 38 | 11 | 3 | 38 | 11 |
| 24 | 40 | 4 | 3 | 35 | 2 | 3 | 23 | 3 |
| 48 | 34 | 7 | 3 | 26 | 4 | 2 | 26 | 4 |
| 120 | 63 | 3 | 3 | 37 | 12 | 3 | 32 | 12 |

| Group | 0.25 | 1 | | | 2.5 (po) | | |
|---|---|---|---|---|---|---|---|
| Time | n | mean | sd | n | mean | sd | n |
| 0 | 3 | 38 | 11 | 3 | 38 | 11 | 3 |
| 24 | 3 | 23 | 4 | 3 | 25 | 2 | 3 |
| 48 | 2 | 30 | 4 | 3 | 32 | 4 | 3 |
| 120 | 3 | 29 | 3 | 2 | 30 | 2 | 3 |

Data from this study support Compound E's ability to down-regulate early and late exhaustion markers KLRG-1 and PD-1, respectively. This downregulation of exhaustion markers is a key factor in the anti-tumor effects of this class of TIM antagonist. Interestingly, the nadir was seen 24 hours after dosing, a whole day earlier than with Compound B, and was maintained until the end of the study. The study was not long enough to observe a return slope as seen with Compound B. Furthermore, unlike Compound C, Compound E is effective after oral administration. It showed comparable changes in PD-1 24 hours after dosing as Compound C in vivo, and similar $EC_{50}$ to Compound C in vitro.

While Compound E's oral bioavailability has not been evaluated in a PK study, the data suggest that it would be at least 10% or higher based on the observation that a 2.5 mg oral dose was as efficacious as a 0.25 mg IV dose. It is important to note that since the response was saturated, it is not possible to differentiate between doses, and bioavailability could be much higher than 10%. Compound E seems to maintain the efficacy of Compound C while potentially being orally bioavailable. The ester to amide switch did not have a negative impact on the compound's efficacy, and may have improved its oral availability and bioavailability.

Example 13. Tumor Growth Inhibition, Overall Survival and Ex Vivo Pharmacodynamic Analysis in Murine Melanoma Model T-cell immunoglobulin mucin protein receptors (TIM) have been identified as phosphatidylserine (PS)-binding receptors. TIM receptors mediate the phagocytosis of apoptotic cells and play a role in maintaining tolerance towards self. This pathway can be hijacked by the tumor microenvironment, which leads to immune suppression in the tumor microenvironment.

Figure 8A:
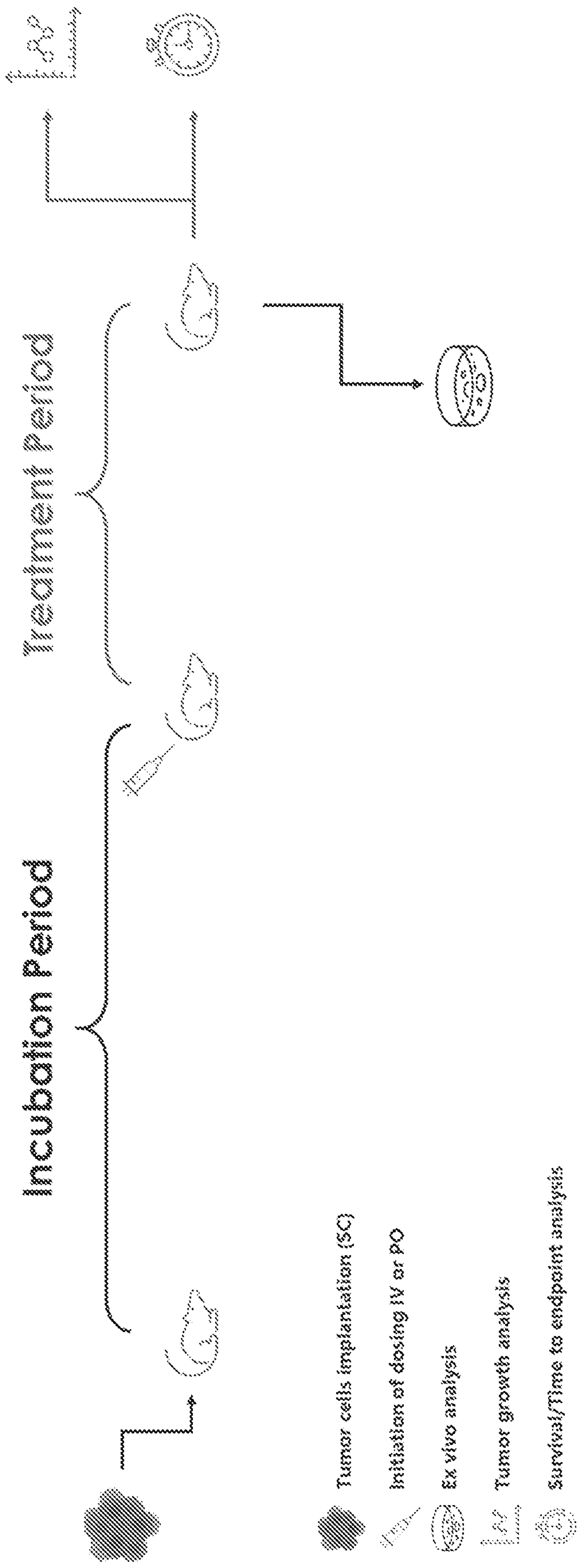
FIG. 8A is a diagram showing the design of the melanoma murine model described in Example 13.

This study was designed to evaluate the effects of Compound B and Compound C on tumor growth and the overall survival of animals implanted SC with $10^5$ melanoma cells. Furthermore, ex vivo analysis of splenocytes at the end of dosing was used to evaluate change in the T-cell population and function. FIG. 8A is a diagram of the study design.

Animals were housed four per cage and had access to food and water ad libitum. Compound B was dissolved in sterile PBS, and pH was adjusted to approximately 7.5. Compound C was first dissolved in DMSO before diluting in sterile PBS. Sterile PBS was used as a control. Compound B was dosed at 4 mg/mouse PO QD. This dose was expected to result in an exposure equivalent to a 1 mg/mouse IV dose. Compound C was dosed at 2.5 mg/mouse IV.

B16F10 melanoma cells were grown in RPMI 1640 media supplemented with 10% FBS and antibiotics (penicillin/streptomycin) using T75 flasks. When cells reached 70-80% confluency, they were treated with 3 ml of 0.25% trypsin/EDTA. Detached cells were harvested. A single-cell suspension was prepared in PBS. A dorsal SC injection of $10^5$ cells in mice marked day 0 of the experiment. Animals were monitored daily, and tumors were measured twice a week.

For tumor growth inhibition, animals were divided into 3 groups. The control group received an IV injection of PBS to match the start time, dosing volume, and dosing frequency of the Compound C treatment group. The treatment group received 100 μl of 4 mg/mouse PO QD of Compound B for 7 days starting at day 7 after tumor implantation, or 2.5 mg/mouse IV QD of Compound C. The endpoint was reached when the tumor reached 1 $cm^3$. Tumor volume was calculated using the following formula:

$$\text{Tumor volume} = \text{length} \times \text{width} \times \frac{1}{2}\text{width}$$

The mice were also monitored for survival, and were euthanized when the tumor size reached the predefined endpoint of 1 $cm^3$.

On day 14, one mouse from each group was sacrificed for ex vivo analysis. One animal with an average tumor size was selected from the control group and the Compound B treatment group. Since no animals in the Compound C treatment group had any visible tumors by day 14, one mouse was selected at random from the Compound C treatment group.

Spleens were collected and a single-cell suspension was prepared for cellular phenotyping by flow cytometry. Cells were stained and gated for CD8. IFNγ, Granzyme B (GzmB), KLRG-1, CTLA-4, TIM-3, and PD-1 expression was evaluated. Cells gated for CD4 were evaluated for FoxP3 expression.

Figure 8B:
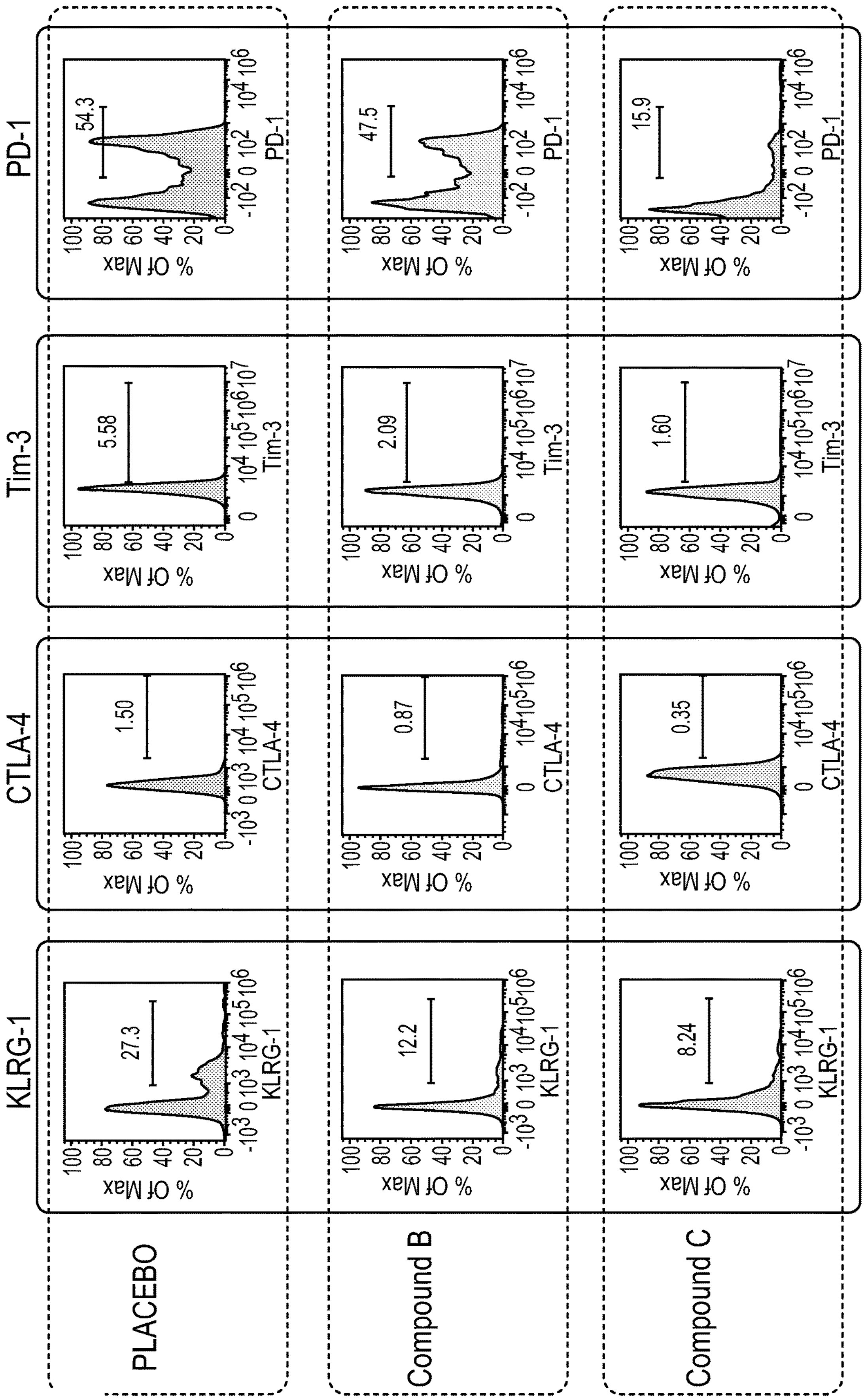
FIG. 8B shows down-regulation of KLRG-1, CTLA-4, TIM3, and PD-1 exhaustion markers in splenocytes isolated from mice in the melanoma murine model described in Example 13 treated with Compound B (PO) or Compound C (IV) versus placebo.

Flow cytometry analysis of splenocytes isolated from one mouse in each treatment group after 7 doses of Compound B or Compound C showed a reduction in all exhaustion markers compared to placebo. FIG. 8B shows that treatment with Compound B or Compound C inhibited KLGR-1 by 55% and 70%, respectively, CTLA-4 by 42% and 77%, respectively, TIM-3 by 63% and 71%, respectively, and PD-1 by 13% and 70%, respectively, as compared to control.

Figure 8C:
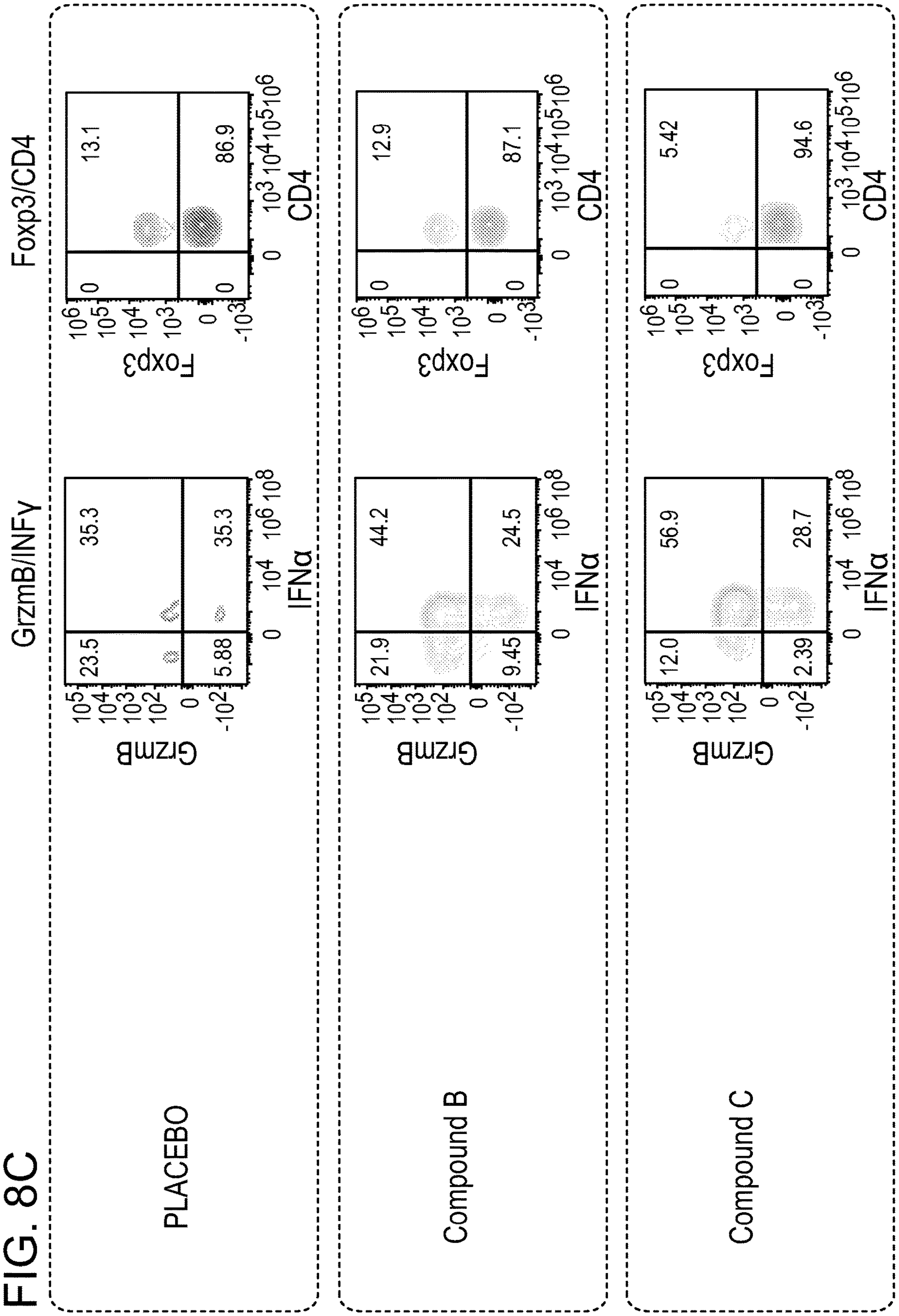
FIG. 8C shows increased anti-tumor activity and down-regulation of anti-tumor suppresser marker in splenocytes isolated from mice in the melanoma murine model described in Example 13 treated with Compound B (PO) or Compound C (IV) versus placebo.

Treatment with Compound B or Compound C stimulated anti-tumor CD8+ T-cell activity, as evident from the increase in GrzmB/INFγ double-positive CD8+ T-cells. FIG. 8C shows that after seven doses of Compound B or Compound C, GrzmB/INFγ double-positive CD8+ T-cells increased by 25% and 62%, respectively, compared to placebo.

Treatment with Compound B or Compound C also inhibited the tumor-induced up-regulation of tolerogenic marker FoxP3 on CD4+ T-cells. FIG. 8C shows that after seven doses of Compound B or Compound C, FoxP3 positive CD4+ T-cells decreased by 1.5% and 59%, respectively, compared to placebo.

By day 14, 5/7 animals in the placebo group showed tumor growth. In the Compound B treatment group, only 3/7 showed any tumor growth, and 0/8 animals in the Compound C treatment group showed any tumor growth. By day 16, all animals in the placebo group showed measurable tumors, versus 3 and 0 in the Compound B and Compound C treatment groups, respectively.

Figure 8D:
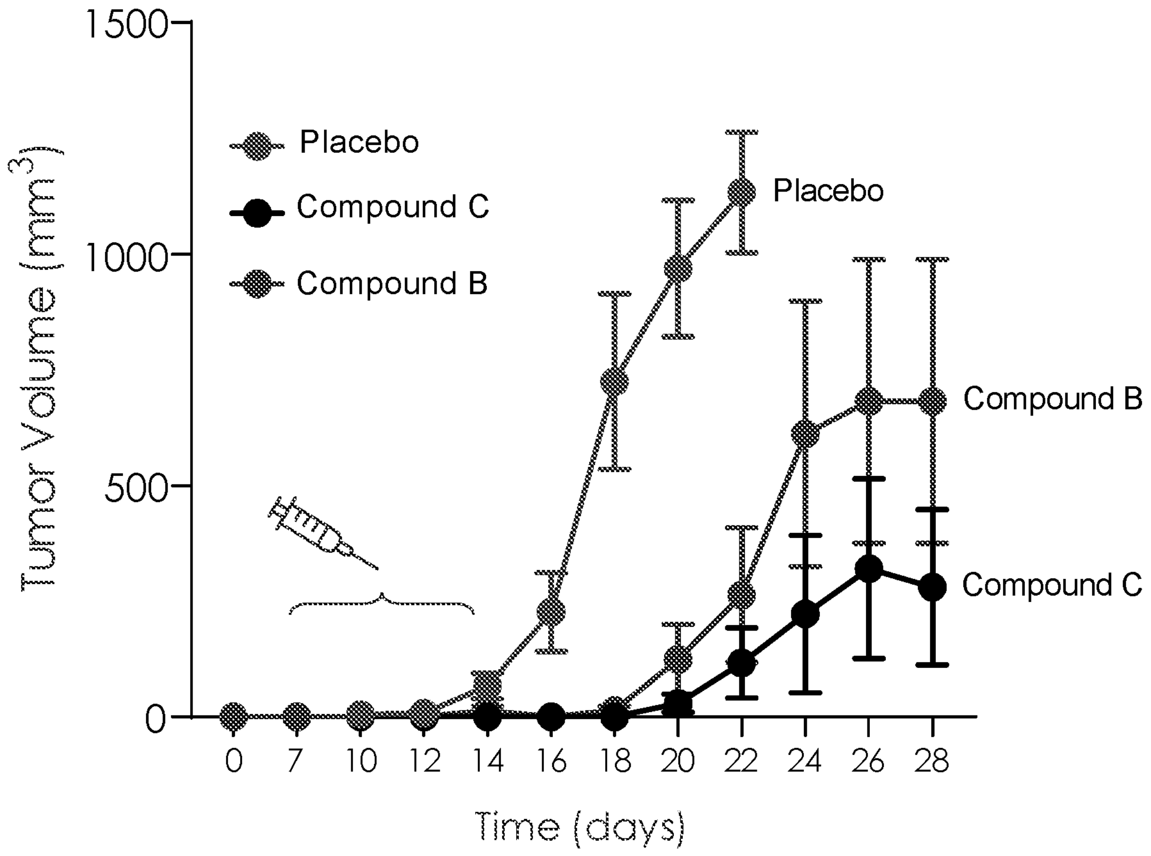
FIG. 8D shows tumor growth inhibition in mice in the melanoma murine model described in Example 13 treated with Compound B (PO) or Compound C (IV) versus placebo.

Tumor growth in the control group progressed as expected, while tumor growth in the Compound B- and Compound C-treated animals lagged. FIG. 8D shows that tumor volume remained statistically lower in the Compound B and Compound C treatment groups than the placebo group for the duration of the study.

Figure 8E:
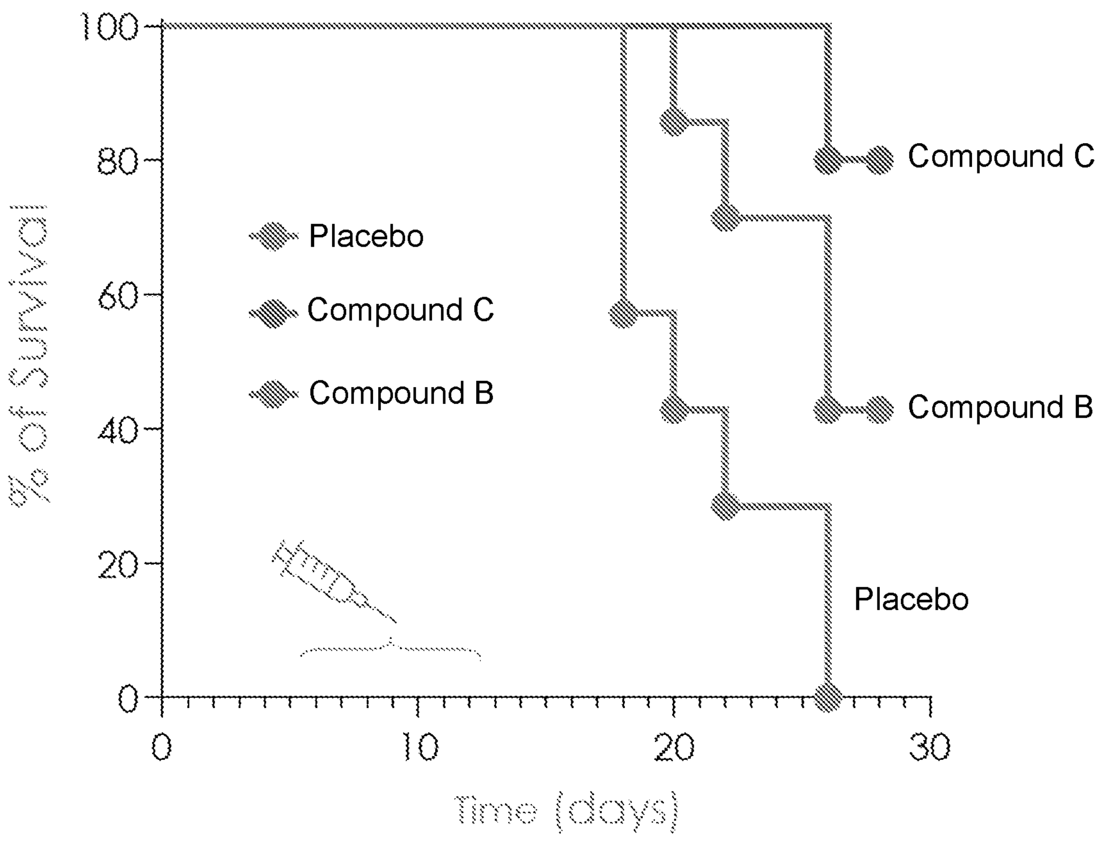
FIG. 8E shows overall survival of mice in the melanoma murine model described in Example 13 treated with Compound B (PO) or Compound C (IV) versus placebo.

FIG. 8E shows that survival in the Compound B and Compound C treatment groups was 40% and 80%, respectively. In the Compound B group, 3/7 animals survived tumor-free for the duration of the study, 1/7 animals survived with a tumor (to day 28) and 3/7 animals did not survive the study. In the Compound C group, 5/8 animals survived tumor-free for the duration of the study, 1/8 animals survived with a tumor (to day 28) and 2/8 animals did not survive the study. No animal in the placebo group survived the study.

Figure 8F:
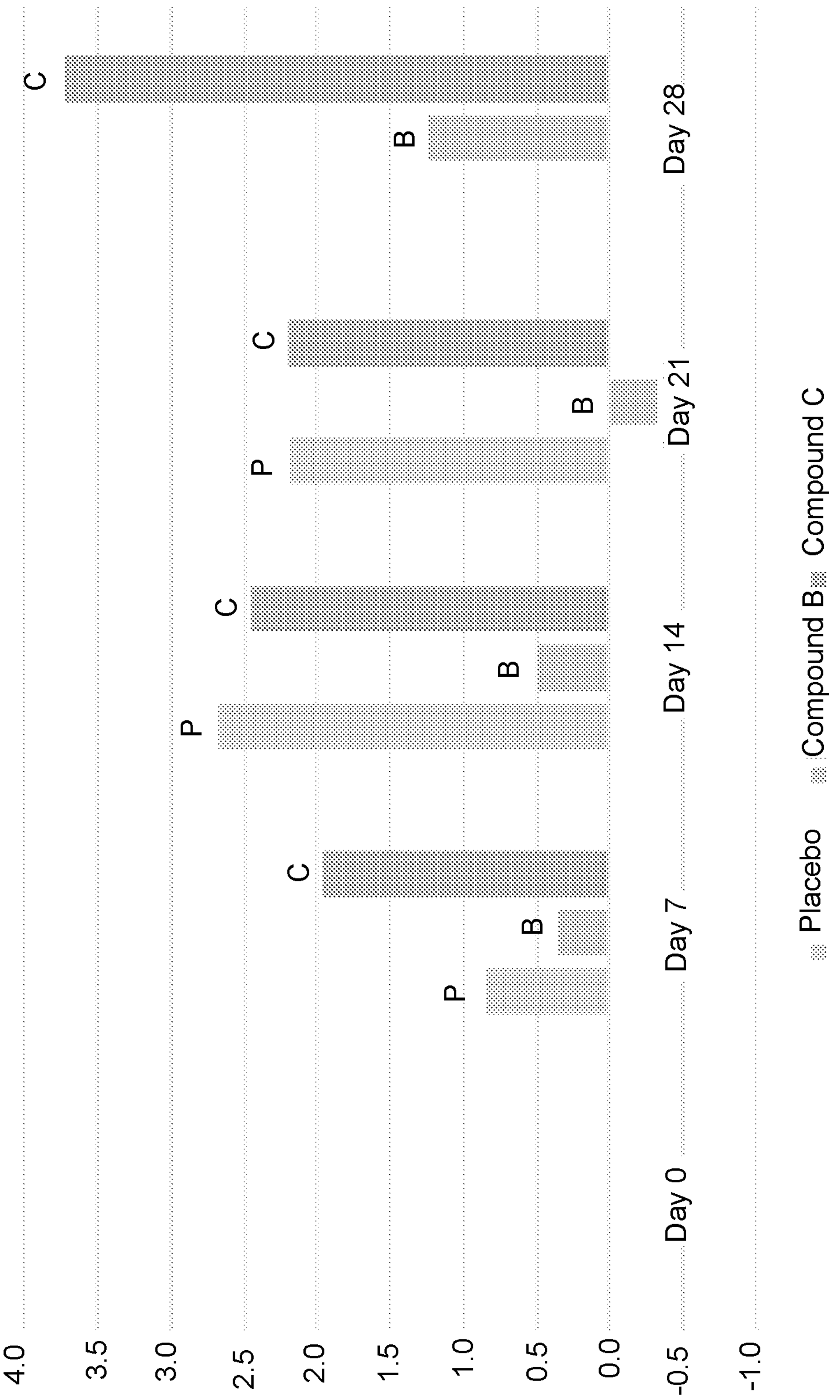
FIG. 8F shows percent change in body weight per treatment group in mice in the melanoma murine model described in Example 13.

FIG. 8F shows that, on average, all animals in all groups gained weight during the study except for the Compound B treatment group on day 21. The greatest measured weight loss in the Compound B treatment group was 3%, and in the Compound C treatment group was 1.5%, versus 1.6% in the placebo group. Fluctuation in weight in all groups was considered within normal weight fluctuation.

In this study, the effect of treatment with Compound B or Compound C on tumor growth inhibition and overall survival was evaluated in a melanoma mouse model. Furthermore, the pharmacological effects of Compound B and Compound C on T-cell phenotype were evaluated ex vivo.

The analysis of splenocytes isolated from Compound B- and Compound C-treated mice confirmed the proposed mechanism of action of Compound B and Compound C. An increase in IFNγ/GzmB double-positive CD8+ and NK cells compared to control was observed. Treatment with Compound B or Compound C also led to a reduction in exhaustion markers KLRG-1, CTLA-4, TIM-3, and PD-1, as well as a reduction in the tolerogenic marker FoxP3 in T-cells. Taken together, these data suggest that Compound B and Compound C have the ability to counteract the immunosuppressive effect of tumors.

A two-way ANOVA analysis of the tumor growth inhibition (TGI) data showed they were statistically significant for both treatment and time. Overall survival was also statistically significant for both Compound B and Compound C treatment groups.

One particularly interesting observation is that 3/7 and 5/8 animals in the Compound B and Compound C treatment groups, respectively, survived the study tumor-free, after receiving just seven doses. It could be possible to increase these numbers if treatment was administered for longer.

Example 14. Tumor Growth Inhibition and Overall Survival in Murine Melanoma Model This study was designed to evaluate the effects of two different doses of Compound B on tumor growth and the overall survival of animals implanted SC with $10^5$ melanoma cells. The study was carried out in accordance with the study described in Example 13, except that mice received either placebo, 0.4 mg/mouse PO QD of Compound B for seven days starting at day 7 after tumor implantation, or 4 mg/mouse PO QD of Compound B for seven days starting at day 7 after tumor implantation.

Figure 9A:
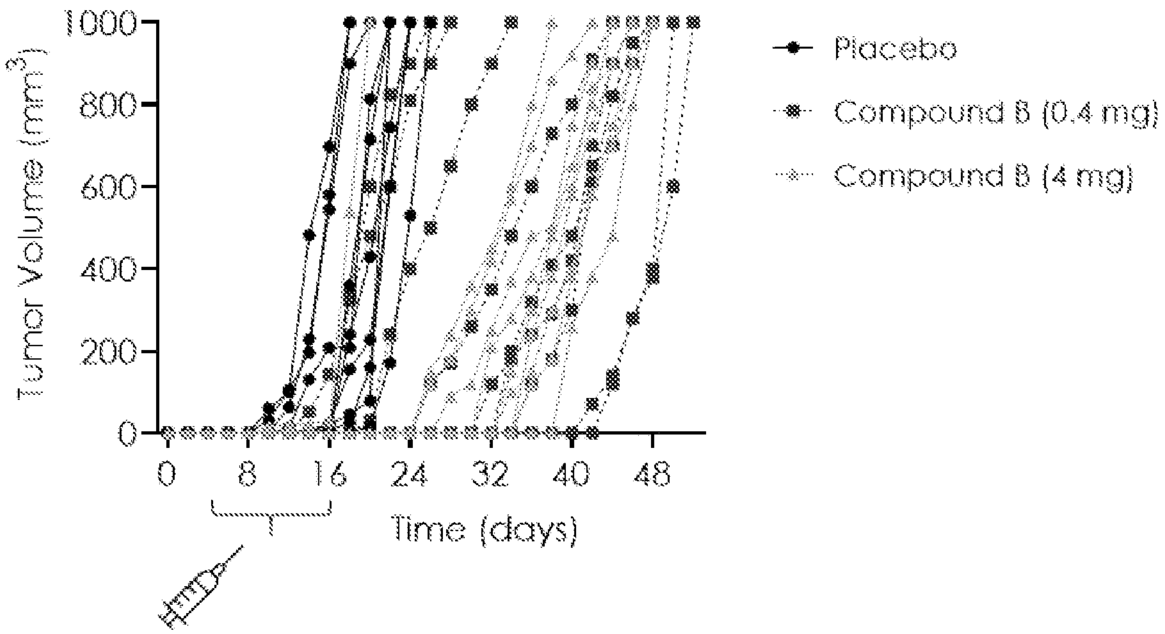
FIG. 9A shows tumor volume in mice treated with 0.4 mg Compound B or 4 mg Compound B versus placebo in the melanoma murine model described in Example 14.
Figure 9B:
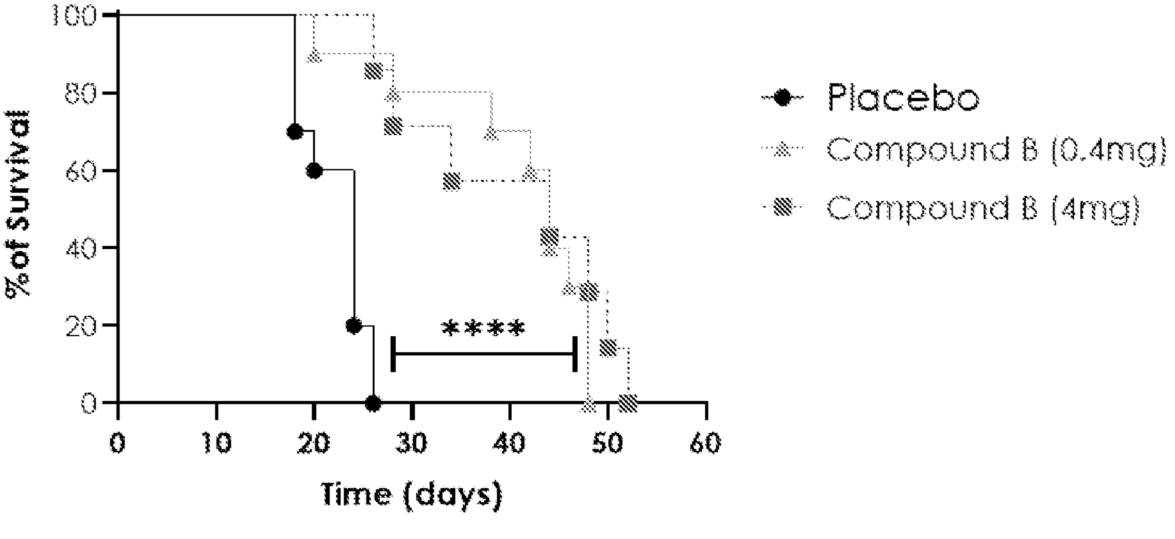
FIG. 9B shows overall survival of mice treated with 0.4 mg Compound B or 4 mg Compound B versus placebo in the melanoma murine model described in Example 14.

FIG. 9A shows that 90% of mice that received 4 mg of Compound B and 70% of mice that received 0.4 mg of Compound B stayed tumor-free for at least 10 days after treatment stopped. FIG. 9B shows there was also a significant increase in survival in both Compound B-treated groups. Taken together, these data show that oral administration of Compound B controlled tumor growth in a dose-dependent manner, with the low dose of Compound B (0.4 mg) showing 70% efficacy of the high-dose (4 mg) treatment.

Example 15. Dose-Dependent Tumor Regression in a Melanoma Murine Model Using Compound B C57BL6 mice received $10^5$ B16F10 melanoma cells via SC injection at day 0. Tumor growth was monitored until tumor size reached 200 to 300 $mm^3$, at which time the mouse was randomized into one of the treatment groups or the control group. Mice were dosed orally until the end of the study.

Figure 10:
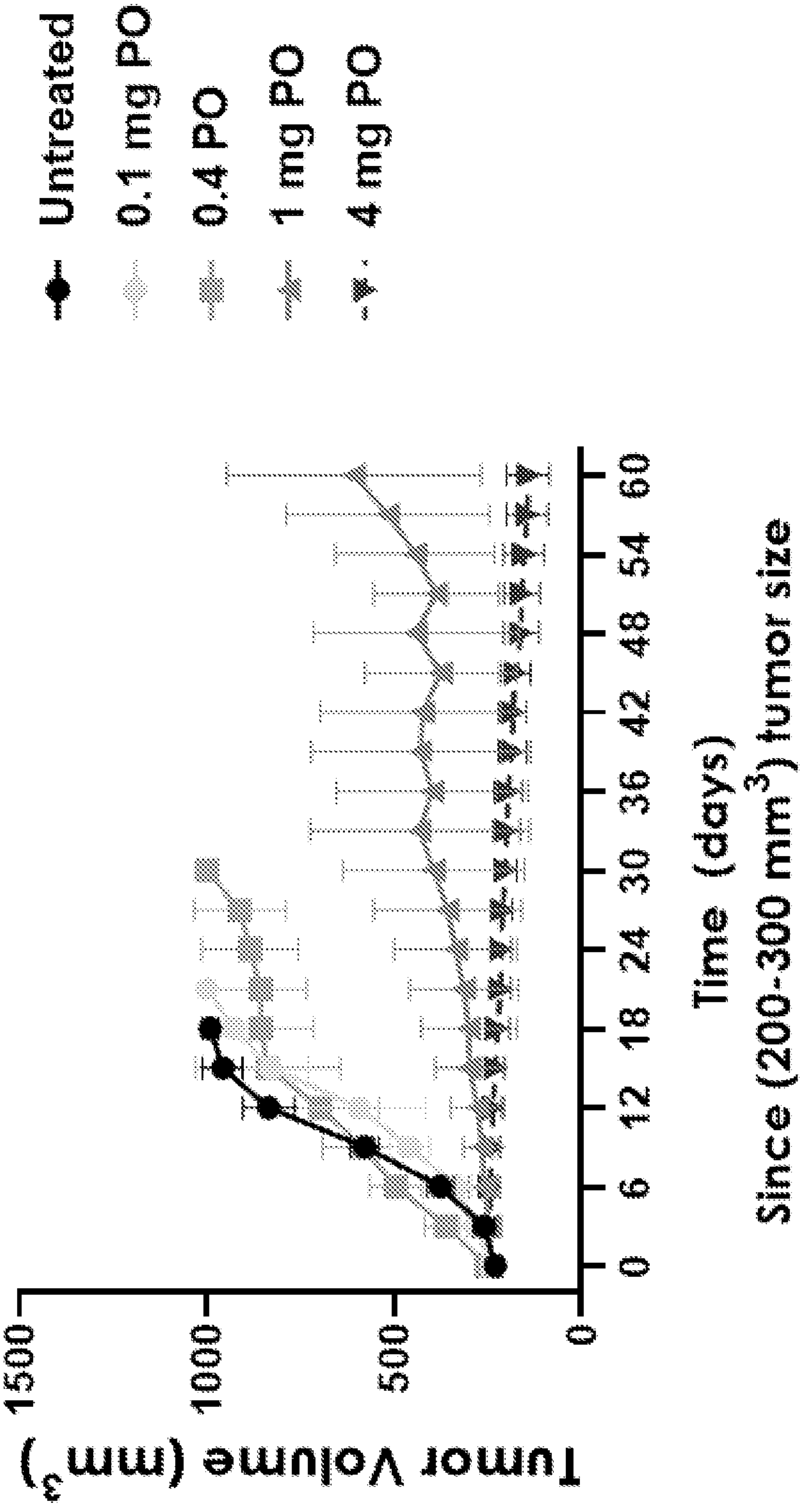
FIG. 10 shows tumor volume in untreated mice and mice treated with the indicated dose of Compound B in the melanoma murine model described in Example 15.

FIG. 10 shows the results of this study. Untreated animals and animals in the low-dose group (who received 0.1 mg Compound B, PO) all died of disease by day 20. Animals in the 0.4-mg Compound B, PO group progressed more slowly than animals in the low-dose group and the untreated mice. Animals in the 0.4-mg Compound B, PO group died by day 30. Tumor growth control was observed early on in the 1-mg Compound B, PO group. Tumor regression was observed in the high-dose group, which received 4 mg Compound B, PO.

These data indicate that Compound B can cause tumor regression as a monotherapy.

Example 16. Compound B Controls Metastasis and Improves Survival in a Melanoma Murine Model C57BL6 mice received $10^5$ B16F10 melanoma cells via IV injection at day 0. At day 7, mice were randomized into one of two groups (n=6 per group): an untreated group and a group treated orally with Compound B at 4 mg/mouse daily for two weeks.

Figure 11A:
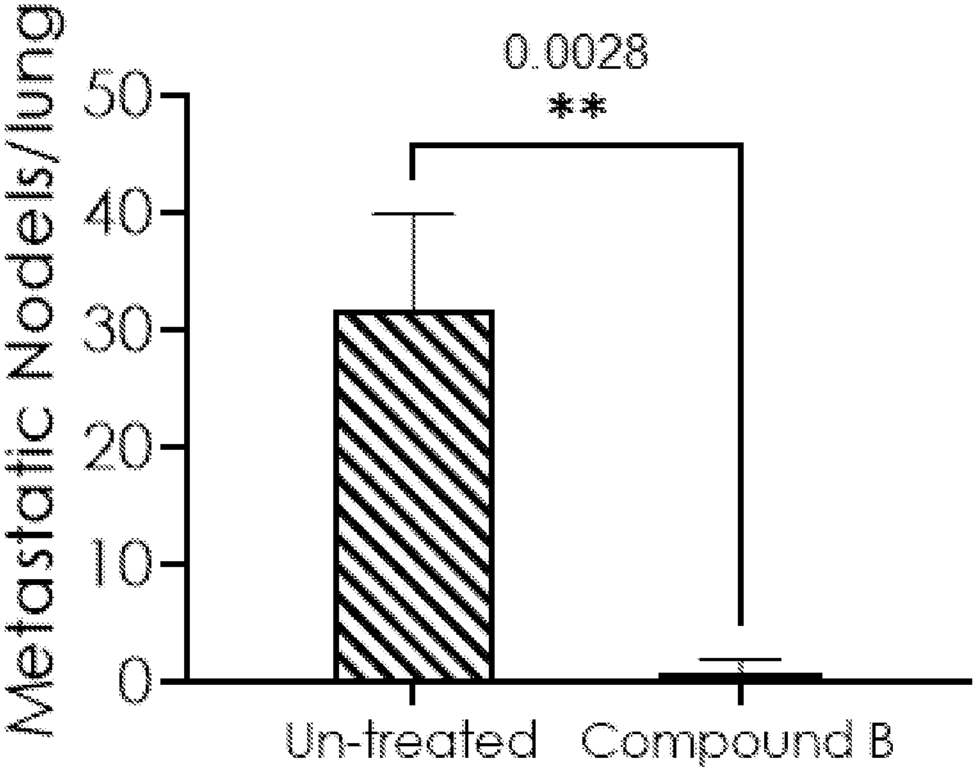
FIG. 11A shows number of metastatic nodes/lung in untreated mice and mice treated with Compound B at 4 mg/mouse daily for one week in the melanoma murine model described in Example 16.

At the end of the first week of treatment (14 days after tumor injection), three mice from each group were euthanized, and lung metastasis was counted (FIG. 11A). By the end of the second week of treatment (21 days after tumor injection), two out of the three remaining control mice had died. The remaining control mouse and the three remaining Compound B-treated mice were euthanized, and lung metastasis assessed (FIG. 11B).

Figure 11B:
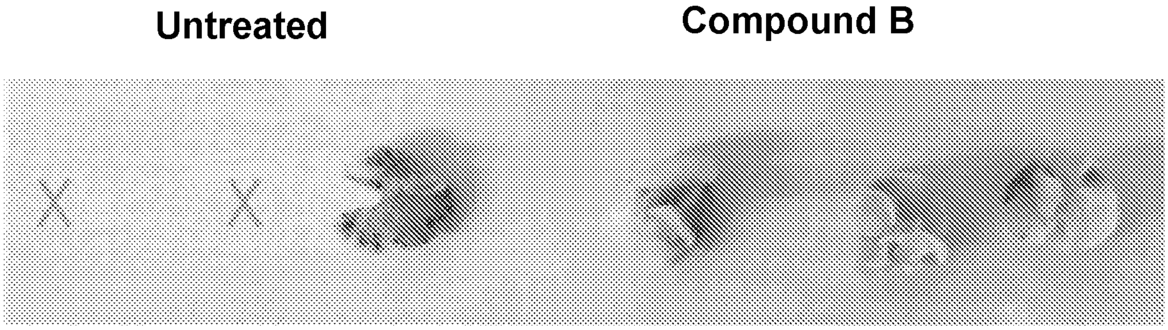
FIG. 11B shows lungs of untreated mice and mice treated with Compound B at 4 mg/mouse daily for two weeks in the melanoma murine model described in Example 16.

FIGS. 11A and 11B show that treatment with Compound B controlled (e.g., prevented) metastasis and improved survival of treated mice compared to untreated mice.

Example 17. Effect of Compound E on Immune Checkpoints KLRG1 and PD1 in C57BL6 Mice Injected with Melanoma Cancer Cells Melanoma B16F10 cells were injected IV into C57BL6 mice on Day 0. On Day 7, mice were administered a single dose of 0.1 mg, 0.25 mg, or 1 mg of Compound E IV or 2.5 mg Compound E PO. One group was left untreated. Three mice at each time point were sacrificed, and their spleens were extracted. Percent KLRG1+ and $PD\text{-}1^+$ T-cells were quantified. Briefly, single-cell suspensions prepared from the extracted spleens were prepared and stained for KLRG1, PD-1 and CD8, and analyzed by flow cytometry.

Figure 12A:
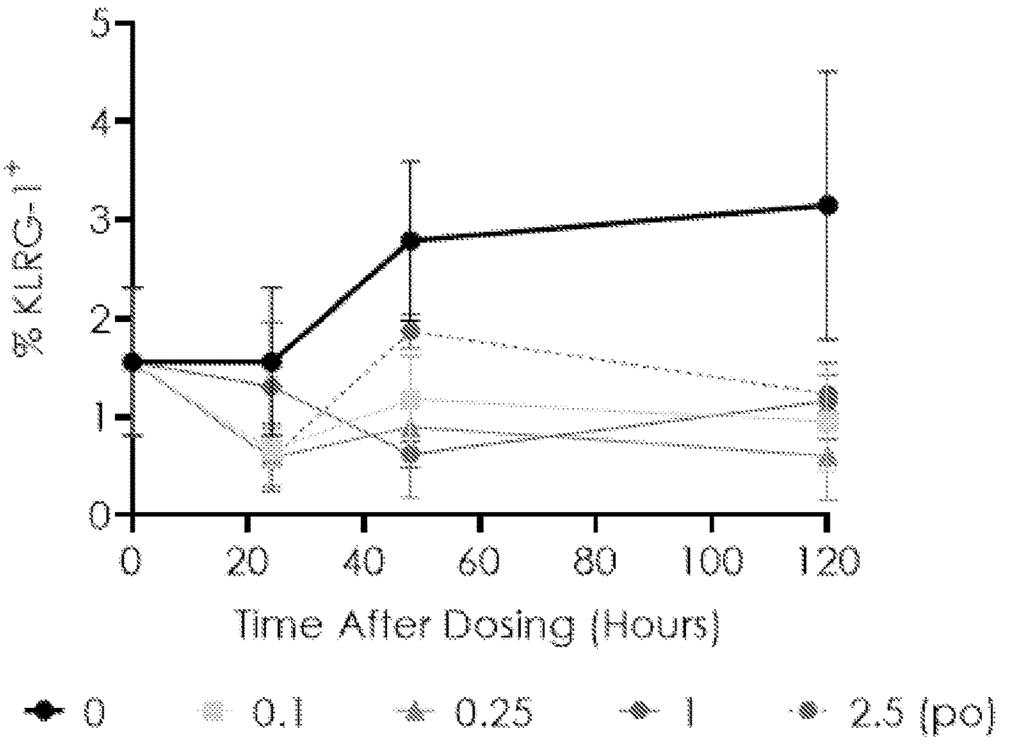
FIG. 12A shows percent KLRG-$1^+$ T-cells in spleens of untreated mice and mice treated with the indicated dose of Compound E in the study described in Example 17.
Figure 12B:
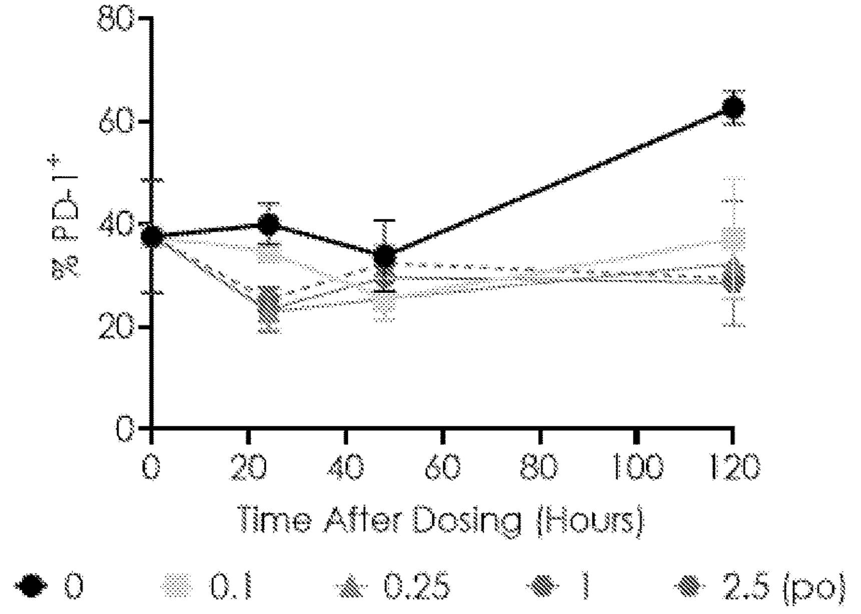
FIG. 12B shows percent PD-$1^+$ T-cells in spleens of untreated mice and mice treated with the indicated dose of Compound E in the study described in Example 17.

FIGS. 12A and 12B show the results of this study. A reduction in both percent KLRG1+ and percent PD1+ T-cells in all groups was observed at all doses of Compound E compared to untreated animals. The data show Compound E to be effective after oral administration.

Example 18. Tumor Growth Inhibition Using Compound E

C57BL/6 mice received $10^5$ B16 F10 melanoma cells via SC injection on day 0. At day 7, mice were treated orally with Compound E at 0.3 or 3 mg daily for seven days. Tumor growth inhibition was monitored until all untreated animals reached end point, defined as death by disease (found dead in the cage) or tumor size of 1,000 $mm^3$ or greater.

Figure 13:
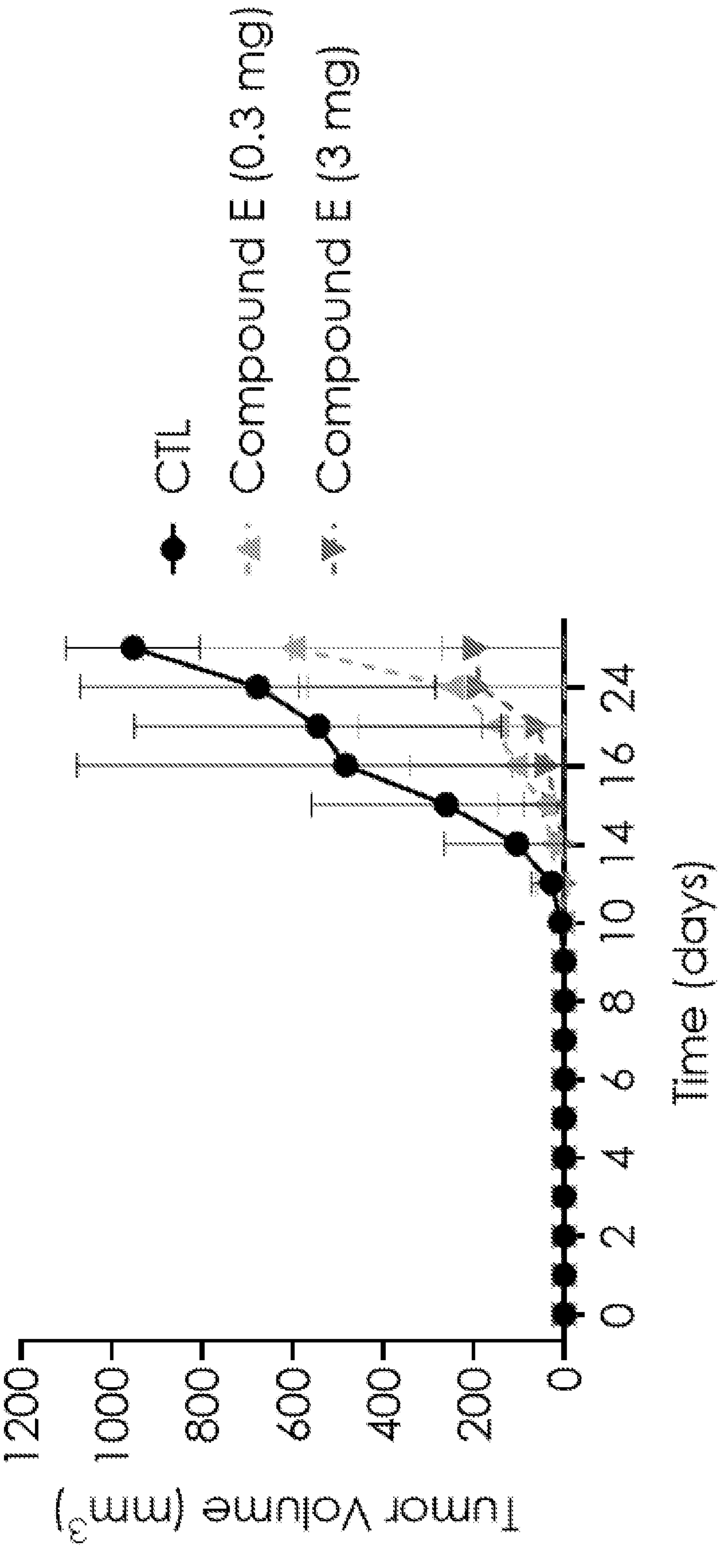
FIG. 13 shows tumor volume in untreated mice and mice treated with 0.3 mg or 3 mg Compound E orally daily for seven days in the melanoma murine model described in Example 18.

FIG. 13 shows dose-dependent inhibition of tumor growth by Compound E.

Example 19. Effect of Compound F on Immune Checkpoints KLRG1 and PD1 in C57BL6 Mice Injected with Melanoma Cancer Cells Melanoma B16F10 cells were injected IV into C57BL6 mice on Day 0. On Day 7, mice were administered a single dose of 0.03 mg, 0.1 mg, 0.3 mg or 1 mg Compound F IV or 1 mg Compound F PO. One group was left untreated. Three mice at each time point were sacrificed, and their spleens were extracted. Percent KLRG1+ and $PD\text{-}1^+$ T-cells were quantified. Briefly, single-cell suspensions prepared from the extracted spleens were prepared and stained for KLRG1, PD-1 and CD8, and analyzed by flow cytometry.

Figure 14A:
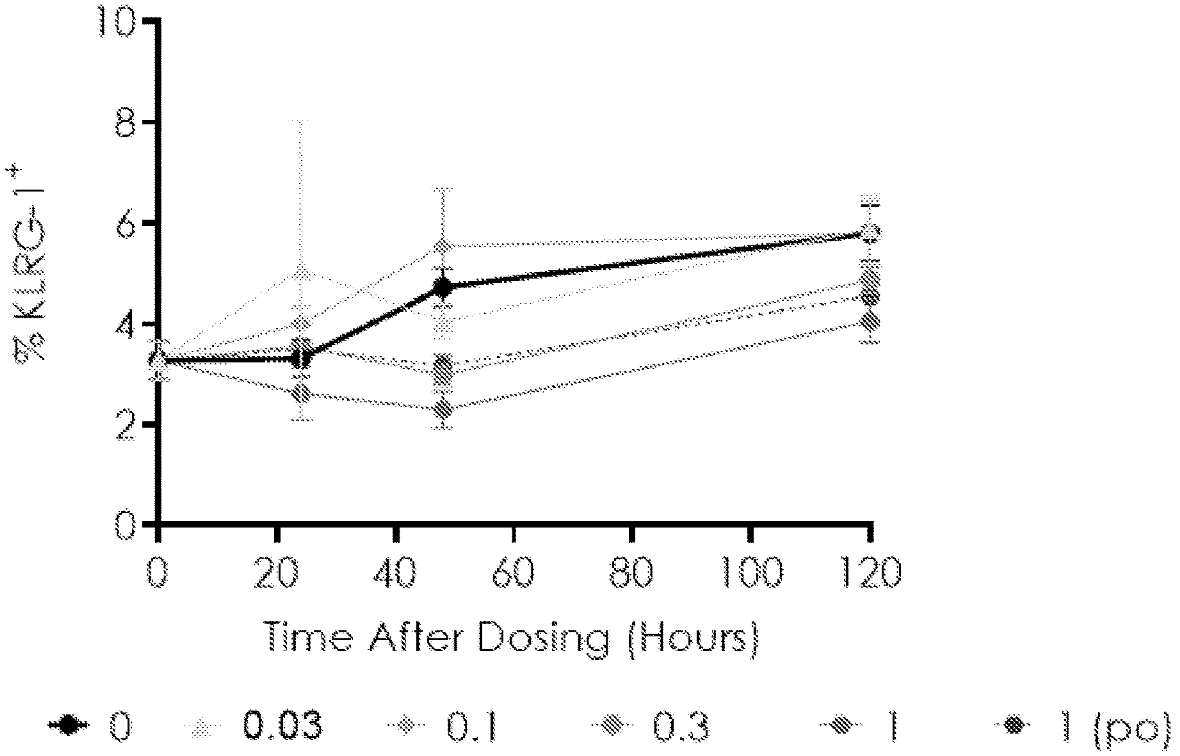
FIG. 14A shows percent KLRG-$1^+$ T-cells in spleens of untreated mice and mice treated with the indicated dose of Compound F in the study described in Example 19.
Figure 14B:
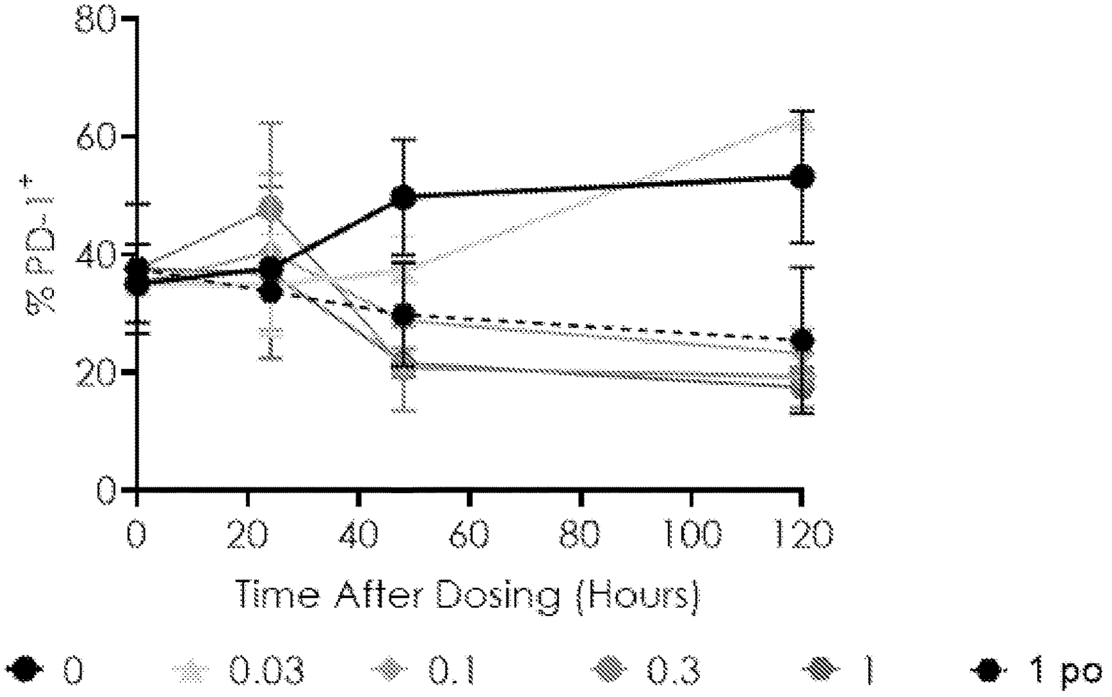
FIG. 14B shows percent PD-$1^+$ T-cells in spleens of untreated mice and mice treated with the indicated dose of Compound F in the study described in Example 19.

FIGS. 14A and 14B show the results of this study. A dose-dependent reduction in both percent KLRG1+ and percent $PD1^+$ T-cells was observed. The data show Compound F to be effective after oral administration.

Example 20. Effect of Compound G on Immune Checkpoints KLRG1 and PD1 in C57BL6 Mice Injected with Melanoma Cancer Cells Melanoma B16F10 cells were injected IV into C57BL6 mice on Day 0. On Day 7, mice were administered a single dose of 0.1 mg, 0.4 mg, or 1 mg Compound G IV or 1 mg Compound G PO. One group was left untreated. Three mice at each time point were sacrificed, and their spleens were extracted. Percent KLRG1+ and $PD\text{-}1^+$ T-cells were quantified. Briefly, single-cell suspensions prepared from the extracted spleens were prepared and stained for KLRG1, PD-1 and CD8, and analyzed by flow cytometry.

Figure 15A:
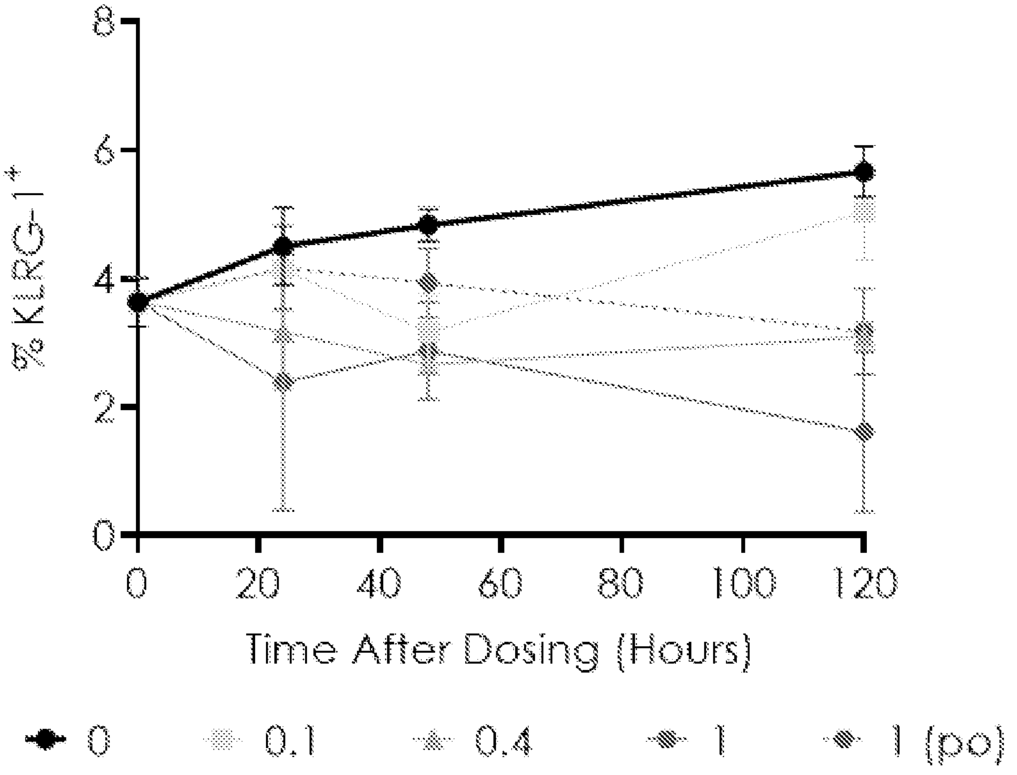
FIG. 15A shows percent KLRG-$1^+$ T-cells in spleens of untreated mice and mice treated with the indicated dose of Compound G in the study described in Example 20.
Figure 15B:
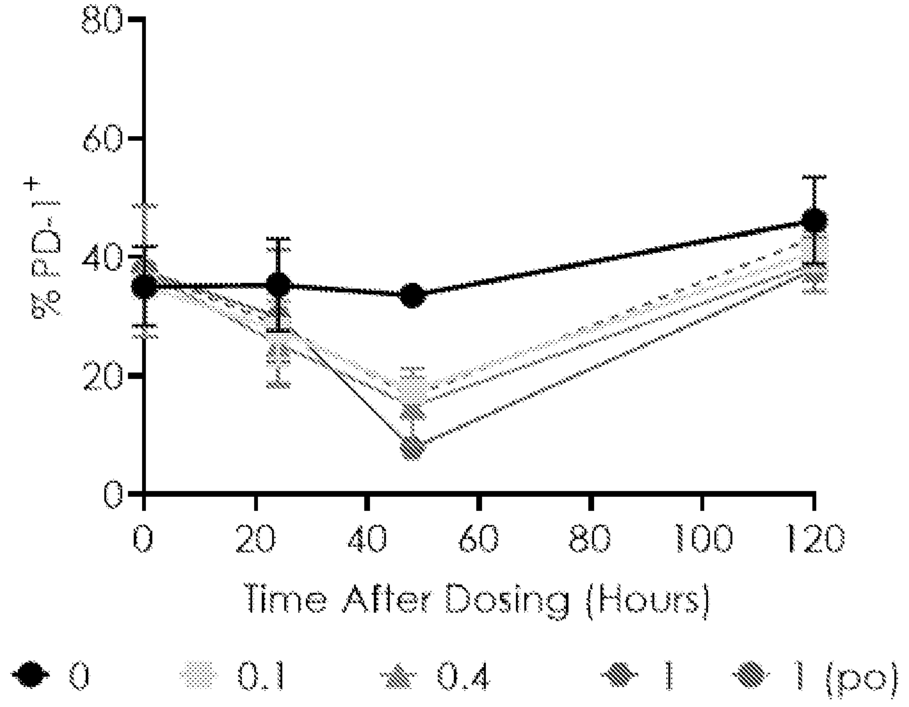
FIG. 15B shows percent PD-$1^+$ T-cells in spleens of untreated mice and mice treated with the indicated dose of Compound G in the study described in Example 20.

FIGS. 15A and 15B show the results of this study. A dose-dependent reduction in both percent KLRG1+ and percent $PD1^+$ T-cells was observed. The data show Compound G to be effective after oral administration.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound represented by the following structural formula:

(I)

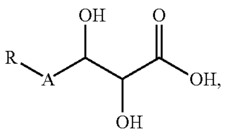

or a pharmaceutically acceptable salt thereof, wherein:

A is *—OC(O)— or *—O($CH_2$)—;

* indicates the point of attachment of A to R;

R is ($C_2$-$C_8$)alkyl or ($C_2$-$C_8$)alkenyl substituted with one or more groups independently selected from ($C_6$-$C_{15}$) aryl or ($C_5$-$C_{15}$)heteroaryl; and wherein each alkyl and alkenyl is optionally and independently further substituted with one or more fluoro, and each aryl and heteroaryl is optionally and independently substituted with one or more $R^2$ independently selected from halo, ($C_1$-$C_3$)alkoxy, ($C_1$-$C_3$)haloalkoxy, ($C_1$-$C_3$)alkyl or ($C_1$-$C_3$)haloalkyl.

2. The compound of claim 1, represented by the following structural formula:

(Ia)

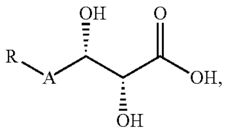

or a pharmaceutically acceptable salt thereof.

3. The compound of claim 1, represented by the following structural formula:

(Ia')

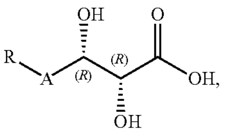

or a pharmaceutically acceptable salt thereof.

4. The compound of claim 1, or a pharmaceutically acceptable salt thereof, wherein A is *—OC(O)—.

5. The compound of claim 1, or a pharmaceutically acceptable salt thereof, wherein A is *—O($CH_2$)—.

6. The compound of claim 1, or a pharmaceutically acceptable salt thereof, wherein R is ($C_2$-$C_5$)alkyl or ($C_2$-$C_5$)alkenyl substituted with one or more groups independently selected from ($C_6$-$C_{15}$)aryl or ($C_5$-$C_{15}$)heteroaryl.

7. The compound of claim 6, or a pharmaceutically acceptable salt thereof, wherein R is ($C_2$-$C_5$)alkyl substituted with one or two groups independently selected from ($C_6$-$C_{15}$)aryl or ($C_5$-$C_{15}$)heteroaryl.

8. The compound of claim 6, or a pharmaceutically acceptable salt thereof, wherein R is ($C_2$-$C_3$)alkyl substituted with one or two groups independently selected from ($C_6$-$C_{15}$)aryl or ($C_5$-$C_{15}$)heteroaryl.

9. The compound of claim 1, or a pharmaceutically acceptable salt thereof, wherein each ($C_6$-$C_{15}$)aryl is independently selected from phenyl or fluorenyl.

10. The compound of claim 1, or a pharmaceutically acceptable salt thereof, wherein each ($C_5$-$C_{15}$)heteroaryl is independently selected from pyridinyl, pyrimidinyl or carbazolyl.

11. The compound of claim 1, or a pharmaceutically acceptable salt thereof, wherein each aryl and heteroaryl is optionally and independently substituted with one or more $R^2$ independently selected from halo, ($C_1$-$C_3$)alkoxy, ($C_1$-$C_3$)fluoroalkoxy, ($C_1$-$C_3$)alkyl or ($C_1$-$C_3$)fluoroalkyl.

12. The compound of claim 1, represented by one of the following structural formulas:

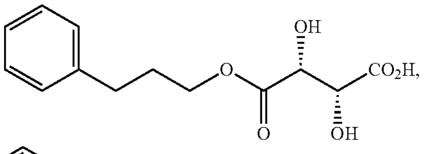

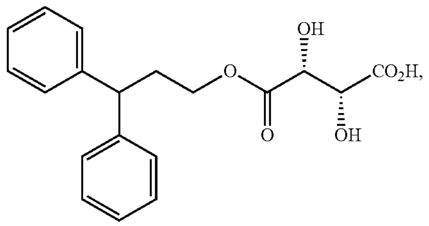

or

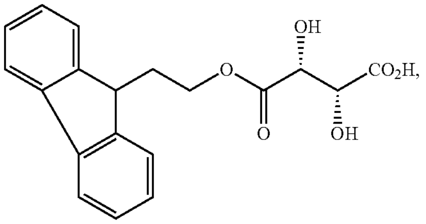

or a pharmaceutically acceptable salt of any of the foregoing.

13. The compound of claim 12, represented by the following structural formula:

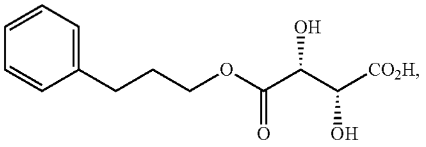 [SMILES: O=C(O)[C@H](O)[C@@H](O)C(=O)OCCCc1ccccc1]

or a pharmaceutically acceptable salt thereof.

14. The compound of claim 12, represented by the following structural formula:

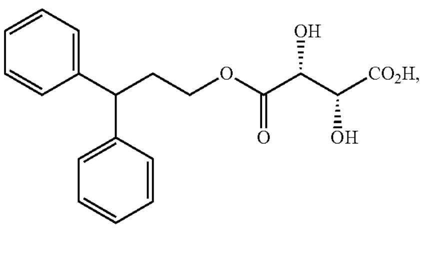 [SMILES: O=C(O)[C@H](O)[C@@H](O)C(=O)OCCC(c1ccccc1)c1ccccc1]

or a pharmaceutically acceptable salt thereof.

15. The compound of claim 12, represented by the following structural formula:

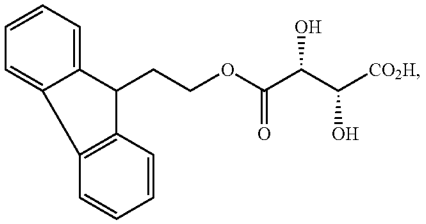 [SMILES: O=C(O)[C@H](O)[C@@H](O)C(=O)OCCC1c2ccccc2-c2ccccc21]
or a pharmaceutically acceptable salt thereof.
16. A pharmaceutical composition comprising the compound of claim 1, or a pharmaceutically acceptable salt thereof, and a pharmaceutically acceptable carrier.
* * * * *